United States Patent
Kim et al.

(10) Patent No.: US 6,660,192 B1
(45) Date of Patent: Dec. 9, 2003

(54) MOLDED WAVEGUIDES

(76) Inventors: Enoch Kim, 321 Dartmouth St., #7, Boston, MA (US) 02116; Younan Xia, 6200 Sand Point Way, NE., Apt. 303, Seattle, WA (US) 98115; Milan Mrksich, 155 N. Harbor Dr., Unit 4308, Chicago, IL (US) 60601; Rebecca J. Jackman, 38 Grove St. #2, Boston, MA (US) 02114; Xiao-Mei Zhao, 13700 Fairhill Rd., Apt. 401, Shaker Heights, OH (US) 44120; Stephen P. Smith, 266 Adams St., Newton, MA (US) 02458; Mara G. Prentiss, 4 Dinsmore Ct., Cambridge, MA (US) 02138; George M. Whitesides, 124 Grasmere St., Newton, MA (US) 02158; Christian Marzolin, 10 rue Saint-Anastase, 75003, Paris (FR)

( * ) Notice: Subject to any disclaimer, the term of this patent is extended or adjusted under 35 U.S.C. 154(b) by 332 days.

(21) Appl. No.: 09/634,201

(22) Filed: Aug. 9, 2000

Related U.S. Application Data

(60) Division of application No. 09/004,583, filed on Jan. 8, 1998, now Pat. No. 6,355,198, which is a continuation-in-part of application No. 08/616,929, filed on Mar. 15, 1996, now abandoned.
(60) Provisional application No. 60/046,689, filed on May 16, 1997.

(51) Int. Cl.$^7$ .......................... B29D 11/00; B29C 39/10; B29C 39/12
(52) U.S. Cl. ...................... 264/1.27; 264/496; 264/621; 264/260
(58) Field of Search ................................. 264/1.27, 1.1, 264/1.24, 1.7, 259, 260, 494, 496, 621, 299, 112, 330

(56) References Cited

U.S. PATENT DOCUMENTS 3,873,359 A 3/1975 Lando
3,873,360 A 3/1975 Lando (List continued on next page.)

FOREIGN PATENT DOCUMENTS

EP 0112721 7/1984

(List continued on next page.)

OTHER PUBLICATIONS

P.M. St. John et al., "Microcontact printing and pattern transfer using trichlorisilanes on oxide substrates," Applied Physics Letters, vol. 68, No. 7, pp. 1022–1024, Feb. 12, 1996.

(List continued on next page.)

*Primary Examiner*—Mathieu D. Vargot
(74) *Attorney, Agent, or Firm*—Wolf, Greenfield & Sacks, P.C.

(57) ABSTRACT

Chemically or biochemically active agents or other species are patterned on a substrate surface by providing a micromold having a contoured surface and forming, on a substrate surface, a chemically or biochemically active agent or fluid precursor of a structure. A chemically or biochemically active agent or fluid precursor also can be transferred from indentations in an applicator to a substrate surface. The substrate surface can be planar or non-planar. Fluid precursors of polymeric structures, inorganic ceramics and salts, and the like can be used to form patterned polymeric articles, inorganic salts and ceramics, reactive ion etch masks, etc. at the surface. The articles can be formed in a pattern including a portion having a lateral dimension of less than about 1 millimeter or smaller. The indentation pattern of the applicator can be used to transfer separate, distinct chemically or biochemically active agents or fluid precursors to separate, isolated regions of a substrate surface. Waveguide arrays, combinatorial chemical or biochemical libraris, etc. can be made. Differences in refractive index of waveguide and cladding can be created by subjecting the waveguide and cladding, made of indentical prepolymeric material, to different polymerization or cross-linking conditions. Interferometers are defined by coupling arrays of waveguides, where coupling can be controlled by altering the difference in refractive index between cladding and waveguide at any desired location of the array. Alteration and refractive index can be created photochemically, chemically, or the like. Sensors also are disclosed, including biochemical sensors.

19 Claims, 22 Drawing Sheets

U.S. PATENT DOCUMENTS

| | | | |
|---|---|---|---|
| 3,900,614 A | 8/1975 | Lando | |
| 4,098,922 A | 7/1978 | Dinella et al. | |
| 4,100,037 A | 7/1978 | Baron et al. | |
| 4,192,764 A | 3/1980 | Madsen | |
| 4,258,001 A | 3/1981 | Pierce et al. | |
| 4,322,457 A | 3/1982 | Baron et al. | |
| 4,472,458 A | 9/1984 | Sirinyan et al. | |
| 4,508,755 A | 4/1985 | Reintjes et al. | |
| 4,555,414 A | 11/1985 | Hoover et al. | |
| 4,637,904 A | 1/1987 | Rounds | |
| 4,690,715 A | 9/1987 | Allara et al. | |
| 4,710,401 A | 12/1987 | Warren, Jr. et al. | |
| 4,728,591 A | 3/1988 | Clark et al. | |
| 4,802,951 A | 2/1989 | Clark et al. | |
| 4,869,778 A | 9/1989 | Cote | |
| 4,959,252 A | 9/1990 | Bonnebat et al. | |
| 5,073,495 A | 12/1991 | Anderson | |
| 5,079,600 A | 1/1992 | Schnur et al. | |
| 5,087,510 A | 2/1992 | Tokas et al. | |
| 5,141,785 A | 8/1992 | Yoshinada et al. | |
| 5,170,461 A | 12/1992 | Yoon et al. | |
| 5,227,474 A | 7/1993 | Johnson | |
| 5,259,926 A | 11/1993 | Kuwabara et al. | |
| 5,345,869 A | 9/1994 | Treverton et al. | |
| 5,385,116 A | 1/1995 | Hattori et al. | |
| 5,439,829 A | 8/1995 | Anderson et al. | |
| 5,471,455 A | 11/1995 | Jabr | |
| 5,484,324 A | 1/1996 | Okabayashi et al. | |
| 5,512,131 A | 4/1996 | Kumar et al. | |
| 5,534,101 A * | 7/1996 | Keyworth et al. | 264/1.27 |
| 5,620,850 A | 4/1997 | Bamdad et al. | |
| 5,976,826 A | 11/1999 | Singhvi et al. | |

FOREIGN PATENT DOCUMENTS

| | | |
|---|---|---|
| EP | 0672765 A1 | 9/1995 |
| JP | 2165933 | 6/1990 |
| JP | 07237229 | 2/1994 |
| WO | WO 96/29629 | 9/1996 |
| WO | WO 97/07429 | 2/1997 |
| WO | WO 97/33737 | 9/1997 |

OTHER PUBLICATIONS

E. Kim et al., "Two–and Three–Dimensional Crystallization of Polymeric Microspheres by Micromolding in Capillaries," Advanced Materials, vol. 8, No. 3, pp. 245–247, Mar. 1, 1996.

E. Kim et al., "Combining Patterned Self–Assembled Monolayers of Alkanethiolates on Gold with Anisotropic Etching of Silicon to Generate Controlled Surface Morphologies," J. Electrochem. Soc., vol. 142, No. 2, pp. 628–633, Feb. 1995.

T.P. Moffat et al., "Patterned Metal Electrodeposition Using an Alkanethiolate Mask," J. Electorchm. Soc., vol. 142, No. 11, Nov. 1995.

E.A. Dobisz et al., "Self–Assembled Monolayer Films for Nanofabrication," Mat. Res. Soc. Symp. Proc., vol. 380, 1995.

J.K. Schoer et al., "Scanning Probe Lithography," Langmuir, vol. 10, No. 3, pp. 617–618, 1994.

H.C. Haverkorn van Rijsewijk, et al., "Manufacture of LaserVision Video Discs by a Photopolymerization Process," Phillips Technical Review, vol. 40, No. 10 (1982), pp. 287–297.

Michael Emmelius et al., "Materials for Optical Data Storage," Ignew. Chem. Int. Ed. Engl. 28, vol. 28, No. 11, (1989), pp. 1445–1600.

F. Lenzman et al., "Thin–Film Micropatterning Using Polymer Microspheres," Chem. Mater., vol. 6, (1994), pp. 156–159.

Stephen Y. Chou et al., "Imprint of sub–25 nm Vias and Trenches in Polymers," Appl. Phys. Lett. 67 (21), 1995, pp. 3114–3116.

C.D. Dushkin et al., "Colored Multilayers from Transparent Submicrometer Spheres," Langmuir, vol. 9 (1993), pp. 3695–3701.

Sadao Hayashi et al., "Imaging by Polystyrene Latex Particles," Journal of Colloid & Interface Science, vol. 144, No. 2 (1991), pp. 538–547.

Younan Xia et al., "Microcontact Printing of Octadecylsiloxane on the Surface of Silicon Dioxide and its Application in Microfabrication," J. Am. Chem. Soc., vol. 117, No. 37 (1995), pp. 9576–9577.

J.F. Dijksman, "Analysis of the Injection–Molding Process," Phillips Tech. Rev. 44, No. 7, (1989), pp. 212–217.

John E. Shaw, "Capillary fill encapsulation of ISFETs," Sensors and Actuators A, 37–38, (1993), pp. 74–76.

Jeffrey W. Jacobs et al., "Combinatorial chemistry—applications of light–directed chemical synthesis," Tibtech, vol. 12 (1994), pp. 19–26.

Steven J. Sundberg et al., "Spatially–Addressable Immobilization of Macromolecules on Solid Supports," J. Am. Chem. Soc., vol. 117 (1995), pp. 12050–12057.

Christopher B. Gorman et al., "Fabrication of Patterned, Electrically Conducting Polypyrrole Using a Self–Assembled Monolayer: A route to All–Organic Circuits," Chem. Matter 7, (1995), pp. 526–629.

James L. Wilbur et al., "Microfabrication by Microcontact Printing of Self–Assembled Monolayers," Adv. Mater. 6, No. 7/8, (1994), pp. 600–604.

Enoch Kim et al., "Polymer microstructures formed by moulding in capillaries," Nature, vol. 376, (1995) pp. 581–584.

Amit Kumar et al., "Patterning Self–Assembled Monolayers: Applications in Material Science," Langmuir, 10, (1994) pp. 1498–1511.

David John Pritchard et al., "Micro–Scale Patterning of Biological Molecules," Agnew, Chem. Int. Ed. Engl. 34, No. 1 (1995), pp. 91–93.

Stephen J. Potochnick et al., "Selective Copper Chemical Vapor Deposition Using Pd–Activated Organosilane Films," Langmuir, vol. 11, No. 6, (1995), pp. 1841–1845.

Walter J. Dressick et al., "Patterning of Self–Assembled Films Using Lithographic Exposure Tools," Jpn. J. Apl. Phys., vol. 32 (1993), pp. 5829–5839.

Genady S. Lazarov et al., "Formation of Two–Dimensional Structures from Colloidal Particles on Fluorinated Oil Substrate," J. Chem. Soc. Faraday Trans. 90 (14), (1994), pp. 2077–2083.

Patrick Hoyer et al., "Small quantum–sized CdS particles assembled to form a regularly nanostructured porous film," Appl. Phys. Lett. 66 (20) (1995), pp. 2700–2702.

Helmut Bonnemann et al., "Preparation and Catalytic Properties of NR+4–Stabilized Palladium Colloids," Applied Organometallic Chemistry, vol. 8 (1994), pp. 361–378.

Kuniaki Nagayami, "Fabrication of Two–Dimensional Colloidal Arrays," Phase Transitions, vol. 45, (1993), pp. 184–203.

Manafred T. Reetz et al., "Size–Selective Synthesis of Nanostructured Transition Metal Clusters," J. Am. Chem. Soc. 116 (1994), pp. 7401–7402.

Manafred T. Reetz et al., "Visualization of Surfactants on Nanostructured Palladium Clusters by a Combination of STM and High–Resolution TEM," Science, vol. 267 (1995), pp. 367–369.

Fiona C. Meldrum et al., "Formation of Thin Films of Platinum, Palladium, and Mixed Platinum: Palladium Nanocrystallites by the Langmuir Monolayer Technique," Chem. Mater. 7 (1995), pp. 1112–1116.

Terrence G. Vargo et al., "Adhesive Electroless Metallization of Fluoropolymeric Substrates," Science, vol. 262 (1993), pp. 1711–1712.

Jeffrey M. Calvert et al., "Deep ultraviolet patterning of monolayer films for high resolution lithography," J. Vac. Sci. Technol. B9 (6) (1991), pp. 3347–3450.

Jian Li et al., "Copper–Based Metallization for ULSI Applications," MRS Bulletin, (1993), pp. 18–21.

James S.H. Chou et al, "Electroless Cu for VLSI", MRS Bulletin (1993), pp. 31–37.

Andre M.T. van der Putten et al., "Electrochemistry of Colloidal Palladium," J. Electrochem. Soc., vol. 139, No. 12 (1992) pp. 3475–3480.

Chiu H. Ting et al., "Selective Electroless Metal Deposition of Integrated Circuit Fabrication," J. Electrochem. Socl., vol. 136, No. 2, (1989), pp. 456–462.

Robert L. Jackson, "PD+S/Poly(acrylic acid) Thin Films as Catalysts for Electroless Copper Deposition: Mechanism of Catalyst Formation," J. Electrochem. Soc., vol. 137, No. 1, (1190), pp. 95–101.

Andre M. T. van der Putten et al., "Anisotropic Deposition of Electroless Nickel," J. Electrochem. Soc., vol. 140, No. 8 (1993), pp. 2229–2235.

Andre M.T. van der Putten, "Controlled Mechanical Adhesion of Electroless Cu Patterns," J. Electrochem. Soc., vol. 140 No. 8, (1993), pp. 2376–2378.

Robert L. Jackson, "Initiation of Electroless Copper Plating Using Pd+2/Poly(acrylic acid) Films," J. Electrochem. Soc. (1998), pp. 3172–3173.

Cecilia Y. Mak, "Electroless Copper Deposition on Metals and Metal Silicides," MRS Bulletin, (1994), pp. 55–62.

Walter J. Dressick et al., "Photopatterning and Selective Electroless Metallization of Surface–Attached Ligands," J. Chem. Mater. 5, (1993), pp. 148–150.

S. Nakahara et al., "Microstructure and Mechanical Properties of Electroless Copper Deposits," Annu. Rev. Mater. Sci. 21, (1991), pp. 93–129.

Noo Li Jeon et al., "Patterned Self–Assembled Monolayers Formed by Microcontact Printing Direct Selective Metallization by Chemical Vapor Deposition on Planar and Nonplanar Substrates," Langmuir 11 (1995), pp. 3204–3206.

Valery M. Dubin, "Electroless Ni–P Deposition on Silicon with Pd Activation," J. Electrochem. Soc., vol. 139, No. 5, May, 1992, pps. 1289–1294.

* cited by examiner

10 μm

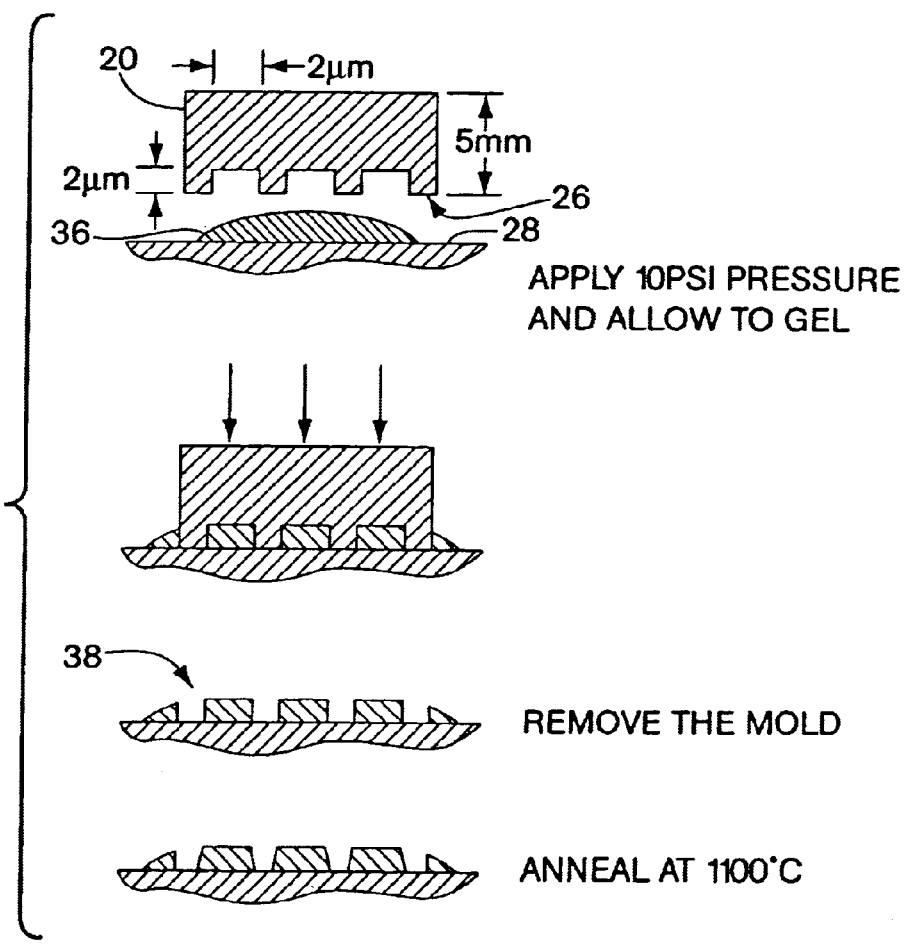

MOLDED WAVEGUIDES

RELATED APPLICATIONS

This application is a divisional of U.S. patent application Ser. No. 09/004,583, filed Jan. 8, 1998, now U.S. Pat. No. 6,355,198, which is a continuation-in-part of U.S. application Ser. No. 08/616,929, filed Mar. 15, 1996, now abandoned, and claims priority to U.S. provisional application Ser. No. 60/046,689, filed May 16, 1997, all of which are incorporated herein by reference.

STATEMENT AS TO POTENTIAL RIGHTS UNDER FEDERALLY SPONSORED RESEARCH AND DEVELOPMENT

Research leading to the invention disclosed and claimed herein was supported in part by the Office of Naval Research, ONR Contract No. N00014-93-I-0498, and by the National Science Foundation, NSF Grant No. PHY 9312572. The U.S. Government may have certain rights to the invention.

FIELD OF THE INVENTION

The present invention relates generally to microprocesses at surfaces, and more particularly to the formation of micro-patterned articles such as waveguides, sensors, and switches on substrates from fluid precursors, and mechanisms for micro-scale positioning of biologically active agents at predetermined regions of a surface.

BACKGROUND OF THE INVENTION

In the fields of chemistry, biology, materials science, microelectronics, and optics, the development of devices that are small relative to the state of the art and conveniently and relatively inexpensively reproduced is important.

A well-known method of production of devices, especially in the area of microelectronics, is photolithography. According to this technique, a negative or positive resist (photoresist) is coated onto an exposed surface of an article. The resist then is irradiated in a predetermined pattern, and portions of the resist that are irradiated (positive resist) or nonirradiated (negative resist) are removed from the surface to produce a predetermined pattern of resist on the surface. This is followed by one or more procedures. According to one, the resist may serve as a mask in an etching process in which areas of the material not covered by the resist are chemically removed, followed by removal of resist to expose a predetermined pattern of a conducting, insulating, or semiconducting material. According to another, the patterned surface is exposed to a plating medium or to metal deposition (for example under vacuum) followed by removal of resist, resulting in a predetermined plated pattern on the surface of the material. In addition to photolithography, x-ray and electron-beam lithography have found analogous use.

In an article entitled "Materials for Optical Data Storage", by Emmelius, et al., *Angewandte Chemie, Int. Ed.* (*English*), 28, 11, 1445–1600 (November, 1989), a review of methods of making CD/ROM, WORM, and EDRAW optical storage disks is presented. According to one method, photolithography is used to create a pattern of protrusions on a surface that can serve as a master for fabrication of articles that have a surface including a series of ridges and protrusions complementary to the photolithographically-produced master. These articles, including microridges and grooves at one surface, can be combined with other materials in a layered structure to form an optical storage device. An article in the Phillips Technical Review, volume 40, number 10 (1982), entitled "Manufacture of LaserVision Video Disks by a Photopolymerization Process", by Haverkorn, et al., discusses similar technology. U.S. Pat. Nos. 5,170,461 (Yoon, et al.), U.S. Pat. No. 4,959,252 (Bonnebat, et al.) and U.S. Pat. No. 5,141,785 (Yoshinada, et al.) describe optical elements such as waveguides and optical recording media. Yoshinada, et al. describe a process involving coating a substrate with a polymer or prepolymer, pressing a contoured stamp into the polymer or prepolymer to create a contoured pattern in a surface of the polymer or prepolymer complementary to the contoured surface of the stamp, removing the stamp, and adding a reflective layer to the contoured surface of the polymer or prepolymer for use as an optical device.

Photolithographic techniques for fabricating surfaces with positional control of chemical functionalities at submicron resolution is described in an article entitled "Patterning of Self-Assembled Films Using Lithographic Exposure Tools", by Dressick, et al., *Jpn. J. Appl. Phys.*, 32, 5829–5839 (December, 1993). The technique involves exposure of a self-assembled film to deep UV irradiation through a mask. According to one technique, photochemical cleavage of an organic group occurs in exposed regions followed by chemical reactivity selectively at those regions.

Photolithography has found application in the biological arena as well. Sundberg, et al. describe a method for patterning receptors, antibodies, and other macromolecules at precise locations on solid substrates using photolithographic techniques in combination with avidin or streptavidin/biotin interaction in an article entitled "Spatially-Addressable Immobilization of Macromolecules on Solid Supports", *J. Am. Chem. Soc.*, 117, 12050–12057 (1995).

Reactive ion etching is a process that is useful in the semiconductor industry and other arenas for forming very small structures having a very high aspect ratio (a very high height/width ratio of features). Reactive ion etching is a dry process in which a gas is accelerated towards a surface to effect etching, in contrast to wet etching processes in which a liquid is simply allowed to contact certain regions of a surface and to chemically react at those regions. In wet etching processes, etching typically takes place not only in a direction perpendicular to the surface, but horizontally, as well. That is, with wet etching it can be difficult to etch relatively precise, vertical channels in a surface. Instead, the sidewalls of the channel are etched horizontally also. Reactive ion etching provides an advantageous alternative for etching channels with good, near-vertical sidewalls.

Reactive ion etching masks should have certain characteristics such as good hardness, inertness to the etchent species, and in many cases electrical insulating properties. Thus, materials suitable for reactive ion etching masks are limited. Many metal masks, such as gold masks, are unsuitable since the metals can sputter easily. Polymeric masks typically degrade under reactive ion etching conditions. A typical prior art reactive ion etching mask is made of silica and is formed by creating a layer of silica on a surface and etching the layer selectively to create a silica mask, using photolithography. Such procedures can be costly. In an article entitled "Poly(siloxane)-based Chemically Amplified Resist Convertable into Silica Glass", by Ito, et al., *Jpn. J. Appl. Phys.*, 32, 6052–6058 (1993), a poly(siloxane)-based chemically amplified resist is reported. A polymeric glass precursor is converted into silicate glass through a lithographic procedure.

Waveguides are generally defined by a core, surrounded by a cladding, that acts as a guide of electromagnetic radiation. The waveguide can propagate radiation via total internal reflection of the radiation within the core. Waveguides have served as important components of sensors and switches, and have been fabricated from a variety of materials including inorganic materials such as glasses and organic materials such as polymers. Polymeric waveguides have been fabricated using reactive ion etching, ultraviolet (UV) laser and electron-beam writing, induced dopant diffusion during polymerization (photo-locking and selective polymerization), selective poling of electro-optically active molecules induced by an electric field, and polymerization of self-assembled prepolymers. One common technique for forming polymeric waveguides is injection molding. For example, voids in a cladding material (or substrate) can be filled, via injection molding, with a core material. However, problems associated with this technique include softening and deformation of the cladding or substrate under temperatures required for injection molding. Fabrication with precision is compromised, typically. In an additional prior art technique, a polymeric film is spun onto a substrate and portions of the film are subsequently exposed to light by a photolithographic process, thereby changing the refractive index of a polymeric film and creating a waveguide in the film. This technique requires expensive and complicated photolithographic systems for base formation of the waveguide array, and subsequent multi-step processing is required such as removal of the polymeric film from the substrate, lamination processing, curing processing, and other processing steps.

U.S. Pat. No. 5,136,678 (Yoshimura) describe fabrication of an optical waveguide array by providing a clad substrate having a number of grooves arranged in lines on a surface of the substrate, the substrate being resistant to a UV-curable resin. A UV-curable resin is used to fill the grooves in the substrate and is UV cured to form a core material, and a covering clad portion is formed over the structure of a material that is the same as or close to the material used as the substrate "cladding".

U.S. Pat. No. 5,313,545 (Kuo, et al.) describes a technique in which a two-part mold made of stainless steel, aluminum, ceramic, or the like is used to mold a polymeric waveguide core material via injection molding. The mold is opened via removal of the two portions, and the waveguide is placed in a second mold into which is injected a cladding material. Kuo, et al. report that a post-mold curing process is sometimes needed to maximize optical and physical qualities of core regions, support apparatus, and end portions.

U.S. Pat. No. 5,390,275 (Lebby, et al.) describe a method for manufacturing a molded waveguide. A first cladding layer is provided, and channels are formed in the first cladding layer. The channels in the first cladding layer are filled with an optically transparent polymer, and a second cladding layer is subsequently affixed over the channels thereby enclosing them.

U.S. Pat. No. 5,481,633 (Mayer) describes vertical coupling structures in which waveguide patterns include sections that lie in close proximity with other sections, for example one directly above another, such that the distance between coupling portions is very small and coupling between different guides can occur.

Biological and chemical interactions can be studied on the micro scale using combinatorial chemistry. This technique, as described in *Chemical & Engineering News*, 74, 7, 28–73 (Feb. 12, 1996), involves formation of different biological or chemical species in a grid pattern on a surface and used, for example, to screen compounds for potential biological or chemical activity. An article entitled "Combinatorial Chemistry—Applications of Light-Directed Chemical Synthesis", by Jacobs, et al., *Trends in Biotechnology*, 12, 19–26 (January, 1994) describes a photolithographic process used in a spatially-addressable synthesis technique for forming a combinatorial library involving photolithography. A surface is derivatized with amine linkers that are blocked by a photochemically cleavable protecting group. The surface is selectively irradiated to liberate free amines that can be coupled to photochemically blocked building blocks. The process is repeated with different regions of the surface being exposed to light and involved in synthesis until a desired array of different compounds, in a grid pattern on the surface, is prepared. Each of these compounds then is assayed simultaneously for binding or activity. Binding "hits" can be identified by the particular location at which binding on the surface occurs.

While the above techniques represent, in some cases, useful advances in the art, many of these techniques require relatively sophisticated apparatus, are expensive, and generally consume more reactants and produce more by-products in collateral fabrication steps than is optimal, and/or lack optimal versatility in application. It is an object of the present invention to provide a variety of techniques for modifying a surface chemically and/or biologically at the micro and nanoscale, and to form very small scale structures, including waveguides and masks for etching processes conveniently, inexpensively, and reproducibly.

SUMMARY OF THE INVENTION

The present invention provides techniques for derivatizing surfaces, biologically, chemically, or physically, according to predetermined patterns. The derivatized surfaces find a variety of uses in a variety of technical areas, or a structure formed on the surface can be removed from the surface and find utility separate from the surface. The invention involves, according to one technique, a method for creating a pattern of a species at a defined region proximate a substrate surface. The method involves providing an article having a contoured surface including at least one indentation defining a pattern and forming at a first region proximate the substrate surface, in a pattern corresponding to the indentation pattern, a fluid precursor of the species. The fluid precursor is allowed to harden at the first region of the substrate surface in a pattern corresponding to the indentation pattern and in an area including a portion having a lateral dimension of less than about 1 mm. A second region proximate the substrate surface, contiguous with the first region, remains free of the species.

The invention also provides a method of promoting a chemical reaction at a defined region proximate a substrate surface. The method involves positioning an article proximate a substrate surface and applying, to a first region proximate the substrate surface via capillary action involving the article, a chemically active agent. A chemical reaction involving the chemically active agent then is allowed to take place at the first region proximate the substrate surface.

The invention also provides a method of promoting a chemical reaction at a defined region proximate a substrate surface that involves providing an article having a contoured surface including at least one indentation defining a pattern, forming at a first region proximate the substrate surface, in a pattern corresponding to the indentation pattern, a chemically active agent, and allowing a chemical reaction to take place proximate the first region of the substrate surface. The chemical reaction takes place in a pattern corresponding to the indentation pattern and in an area including a portion having a lateral dimension of less than about 1 mm. A second region proximate the substrate surface, contiguous with the first region, remains free of the reaction.

The invention also provides a method of applying a biochemically active agent to a region proximate a substrate surface. An article having a contoured surface, as described above, is used to form, at a first region proximate the substrate surface and in a pattern corresponding to the indentation pattern, a pattern of the biochemically active agent. The method can further involve allowing a biochemical interaction involving the biochemically active agent to take place proximate the first region of the substrate surface in a pattern corresponding to the indentation pattern. The first region can be defined by an area having a lateral dimension of less than about 1 mm, and a second region proximate the substrate surface, contiguous with the first region, can be left free of the biochemical interaction. The biochemically active agent can be a biological binding partner that can be used in subsequent binding with other agents.

The invention also provides a method of creating a pattern of a species proximate a substrate surface that includes positioning a forming article proximate a substrate surface and applying, to a first region proximate the substrate surface via capillary action involving the article, a fluid precursor of the species. The fluid precursor is allowed to harden and the forming article is removed from the substrate surface.

The invention also provides a method of promoting a chemical reaction at a defined region proximate a substrate surface. The method involves transferring a chemically active agent from an applicator having a contoured surface including at least one indentation defining an application pattern to a first region proximate a substrate surface in a pattern corresponding to the indentation pattern. A second region proximate the surface, contiguous with the first region, is allowed to remain free of the chemically active agent. A chemical reaction involving the chemically active agent can take place at the first region.

The invention also provides a method of promoting a biochemical interaction at a defined region proximate a substrate surface that involves transferring a biochemically active agent from an applicator having a contoured surface including at least one indentation defining an application pattern to a first region proximate a substrate surface in a pattern corresponding to the application pattern. A second region proximate the surface, contiguous with the first region, can remain free of the biochemically active agent. A biochemical interaction involving the biochemically active agent can be allowed to take place at the first region.

The invention also provides a method of applying to a substrate surface a biochemically active agent that involves positioning an article proximate a substrate surface and applying, to a first region proximate the substrate surface via capillary action involving the article, a biochemically active agent. A biochemical interaction involving the biochemically active agent is allowed to take place at the first region.

The invention also provides a method for applying essentially instantaneously to a first and a second region proximate a substrate surface separated from each other by an intervening region, distinct first and second chemically active agents, respectively. The intervening region is left essentially free of the chemically active agent. The method can involve allowing a chemical reaction involving at least one chemically active agent to subsequently take place proximate the first or second region. The method also can involve applying essentially instantaneously to the first and second regions distinct first and second biochemically active agents while leaving the intervening region free of the biochemically active agent.

The invention also provides a method involving applying essentially instantaneously to a first and a second region proximate a substrate surface distinct first and second biochemically active agents, respectively. The first and second regions are separated from each other by an intervening region that remains free of biochemically active agent. The method can be carried out as well with first and second biochemically active agents that are the same.

The invention also provides a method involving applying a first reactant to a first region proximate a surface and allowing a first reaction to take place at the first region. A second reactant then is applied to a second region proximate the surface that is different from the first region but that includes a portion intersecting the first region. The first region is blocked except at the intersecting region during this step, thereby preventing the first reactant from contacting the first region except at the intersecting portion. A second reaction is allowed to take place at the second region, thereby creating a first chemical characteristic at the first region except at the intersecting portion, a second chemical characteristic at the second region except at the intersecting portion, and a third chemical characteristic at the intersecting portion.

The invention also provides a method of establishing a first chemical functionality at a first region proximate a substrate surface and a different chemical functionality at a second region proximate the substrate surface contiguous with the first region. The method involves applying to the first region proximate the substrate surface a deprotecting species to chemically deprotect the first region of the substrate surface and thereby render it chemically reactive, while leaving the second region free of deprotection. Alternatively, the technique can involve transferring to the second region of the substrate surface a chemical protecting species. The method further involves exposing the substrate surface to a chemically or biochemically reactive species that reacts at the first region proximate the substrate surface and does not react at the second region. The technique can be used to create a combinatorial library via a series of deprotecting/reacting, re-protecting steps or protecting/reacting/deprotecting steps. Transfer of protecting or deprotecting species to the surface can take place essentially instantaneously.

The invention also provides a method of creating, on a substrate surface, a patterned, self-assembled monolayer, involving transferring a self-assembled monolayer-forming species from an applicator having a contoured surface including at least one indentation defining an application pattern to a first region proximate the substrate surface. A self-assembled monolayer proximate the first region is thereby formed corresponding to the indentation pattern. A second region proximate the surface, contiguous with the first region, remains free of the self-assembled monolayer.

The invention also provides a method involving providing a surface carrying a plurality of chelating agents distributed evenly thereacross and applying to two discrete regions of the surface a metal ion that is coordinated by the chelating agent, while leaving a region intervening the two discrete regions free of the metal ion, thereby creating two discrete regions carrying chelating agents coordinating metal ions.

The invention also provides a method involving providing a surface carrying an essentially even distribution thereacross of chelating agents coordinating metal ions, and applying to two discrete regions at the surface a biologically active agent, while leaving a region intervening the two discrete regions free of the biologically active agent.

The invention also provides an article defined by a substrate having a surface and a self-assembled monolayer on the surface. The monolayer is formed of at least a first species having a formula X—R—Ch—M, wherein X represents a functional group and R represents a spacer moiety that, together, are able to promote formation at the surface of a self-assembled monolayer. Ch represents a chelating agent that coordinates a metal ion. M represents a metal ion coordinated to the chelating agent. The article further includes a pattern of biological agent coordinated to metal ion at a first region proximate the surface. A second region proximate the surface, contiguous with the first region, remains free of biological agent coordinated to metal ion.

The invention also provides a method of creating a patterned, self-assembled monolayer on a substrate surface. The method involves transferring a self-assembled monolayer-forming species from an applicator having a contoured surface including at least one indentation defining an application pattern to a first region proximate a substrate surface. A self-assembled monolayer is thereby formed proximate the first region of the substrate surface corresponding to the indentation pattern. A second region proximate the surface, contiguous with the first region, is left free of self-assembled monolayer. The self-assembled monolayer can be transferred essentially instantaneously to the first region proximate the substrate surface in this manner.

The invention also provides a method for providing a surface carrying a plurality of chelating agents distributed evenly thereacross and applying to two discrete regions at the surface a metal ion that is coordinated by the chelating agent. A region intervening the two discrete regions is left free of metal ion.

The invention also provides a method involving providing a surface that carries, essentially evenly distributed thereacross, chelating agents coordinating metal ions. A biochemically active agent is applied to two discrete regions at the surface and a region intervening the two discrete regions remains free of the biochemically active agent.

The invention also provides an article including a surface and a pathway proximate the surface delineating a pattern at a first region proximate the surface. The pattern includes at least one region defining a continuous essentially linear portion of product formed proximate the surface. The product is formed in this manner via reaction involving a chemically active agent promoting the reaction that had been transferred proximate the surface from an applicator. The linear portion of the product has a dimension parallel to the surface of less than about one millimeter.

The invention also provides an article as described above, where the pattern is defined by a plurality of microbeads assembled at the surface. Any patterns formed in this manner can have at least one section having a dimension parallel to the surface of less than about one millimeter.

The fluid precursors, chemically active agents, biochemically active agents, and carriers can be any of a variety of species including prepolymeric species, biological binding partners, inorganic salts, ceramics, metals, catalysts, colloidal activating agents, and the like.

A variety of combinations of the above-described inventive methods can be carried out, for example formation of a pattern can be carried out via capillary action, instantaneous transfer can take place to form a pattern on a surface having a lateral dimension of less than about 1 mm, and the like. Articles formed by the methods above, or by any combination of these methods, and articles formed by other methods are included. The methods can be carried out on essentially planar or non-planar surfaces.

BRIEF DESCRIPTION OF THE DRAWINGS

FIG. 1 illustrates schematically an arrangement for derivatizing a surface in a predetermined pattern according to one embodiment of the invention;

FIG. 2 is a schematic illustration of a technique for transferring a chemically or biochemically active agent or fluid precursor of an article from essentially linear indentations of an applicator defining an indentation pattern to a substrate surface in a pattern corresponding to the indentation pattern;

FIGS. 3*a*–3*d* are photocopies of scanning electron micrographs (SEMs) of patterned polymeric structures formed from hardenable fluid precursors in which the patterned structures remain at the surface (FIGS. 3*a–c*) or are removed from the surface to form a free-standing structure (FIG. 3*d*);

FIGS. 4*a*–4*h* are photocopies of SEM images of inorganic and organic microstructures patterned on surfaces in accordance with the invention;

FIG. 5 is a photocopy of an electron micrograph of microspheres assembled in a predetermined pattern proximate a substrate surface from a fluid precursor in accordance with the invention;

FIGS. 6*a*–6*c* are photocopies of SEM images of metallic microstructures formed proximate predetermined regions of a substrate surface in accordance with the invention;

FIGS. 7*a*–7*c* are photocopies of SEM images of a substrate surface derivatized in a pattern with resist followed by lithography to etch the substrate surface in a pattern complementary to the resist pattern;

FIG. 8 illustrates schematically the formation of a free-standing article from a fluid precursor, using a substrate surface and a forming article including a pattern of indentations in accordance with the invention;

FIGS. 9*a*–9*d* are photocopies of SEM images of a free-standing article prepared in accordance with the technique schematically illustrated in FIG. 8 and use of that article as a mask adjacent a substrate surface in vapor deposition of metal (FIG. 9*b*) or creation of a secondary resist formed by a self-assembled monolayer deposited in a pattern complementary to that of the mask, followed by removal of the mask and vapor deposition of metal in a pattern complementary to the secondary resist pattern (FIGS. 9*c–d*);

FIGS. 10*a*–10*c* illustrate schematically (FIG. 10*a*), and via photoreproduction of optical micrographs (FIGS. 10*b, c*), a process involving derivatizing a surface with resist via micromolding, a mask so produced, and a substrate surface etched selectively at regions not covered by the mask;

FIG. 11 illustrates schematically a technique for transfer of a chemically or biochemically active agent or a fluid precursor of an article from an applicator having a discontinuous indentation pattern to regions proximate a substrate surface in a pattern corresponding to the indentation pattern;

FIG. 12 illustrates schematically the transfer, from an article including an indentation pattern, of a chemically or biochemically active agent or other fluid species to a non-planar substrate surface in a pattern corresponding to the indentation pattern;

FIG. 13 illustrates schematically a multi-layered article formed using successive micromolding techniques of the invention that can serve as a waveguide, and is a cross-section through line a—a of FIG. 15;

FIG. 25 illustrates schematically another technique of the invention for forming a structure from a precursor, on a substrate surface;

DETAILED DESCRIPTION OF THE INVENTION

U.S. patent application Ser. No. 08/616,692, filed Mar. 15, 1996, Entitled "Microcontact Printing of Catalytic Colloids" by Hidber, et al., U.S. Provisional Patent Appln. S. No. 60/046,689, filed May 16, 1997, entitled "Molded Waveguides and Waveguide Couplers", by Kim, et al., and U.S. patent application Ser. No. 08/616,929, filed Mar. 15, 1996 by Kim, et al., entitled "Method of Forming Articles and Patterning Surfaces via Capillary Micromolding" both are incorporated herein by reference in their entirety.

The present invention provides, in one aspect, techniques for placement, at regions proximate a substrate surface, of chemically or biochemically active agents, fluid precursors of articles such as waveguides to be immobilized proximate a substrate surface, and/or other species desirably transferred to a region or regions proximate a substrate surface in a pattern. "Fluid precursor", as used herein, means a material that is fluid enough that it can be formed into a pattern using a forming article, using techniques described herein. The invention utilizes an applicator having a pattern of indentations that can be used to transfer such a species from the indentations to a region proximate the substrate surface or that can serve as a mold that when, positioned proximate a substrate surface, can define a region in which such a species is positioned. In one set of preferred embodiments the applicator is used to transfer a fluid precursor from the indentations to a region proximate a substrate surface where the precursor is hardened to the point it is self-supporting and the applicator can be removed. "Self-supporting, in this context, means that the precursor does not lose its form unacceptably upon removal of the forming article and can retain its form during a further hardening procedure. Alternatively, the applicator can be used to transfer a fluid precursor to a substrate surface and the applicator can be removed prior to hardening the fluid, but maintaining the fluid within channels defined between indentations in the contoured applicator surface and the substrate surface until the fluid is hardened is preferred, since the ultimate shape of features of the pattern on the substrate is thereby better-controlled.

Figure 1:
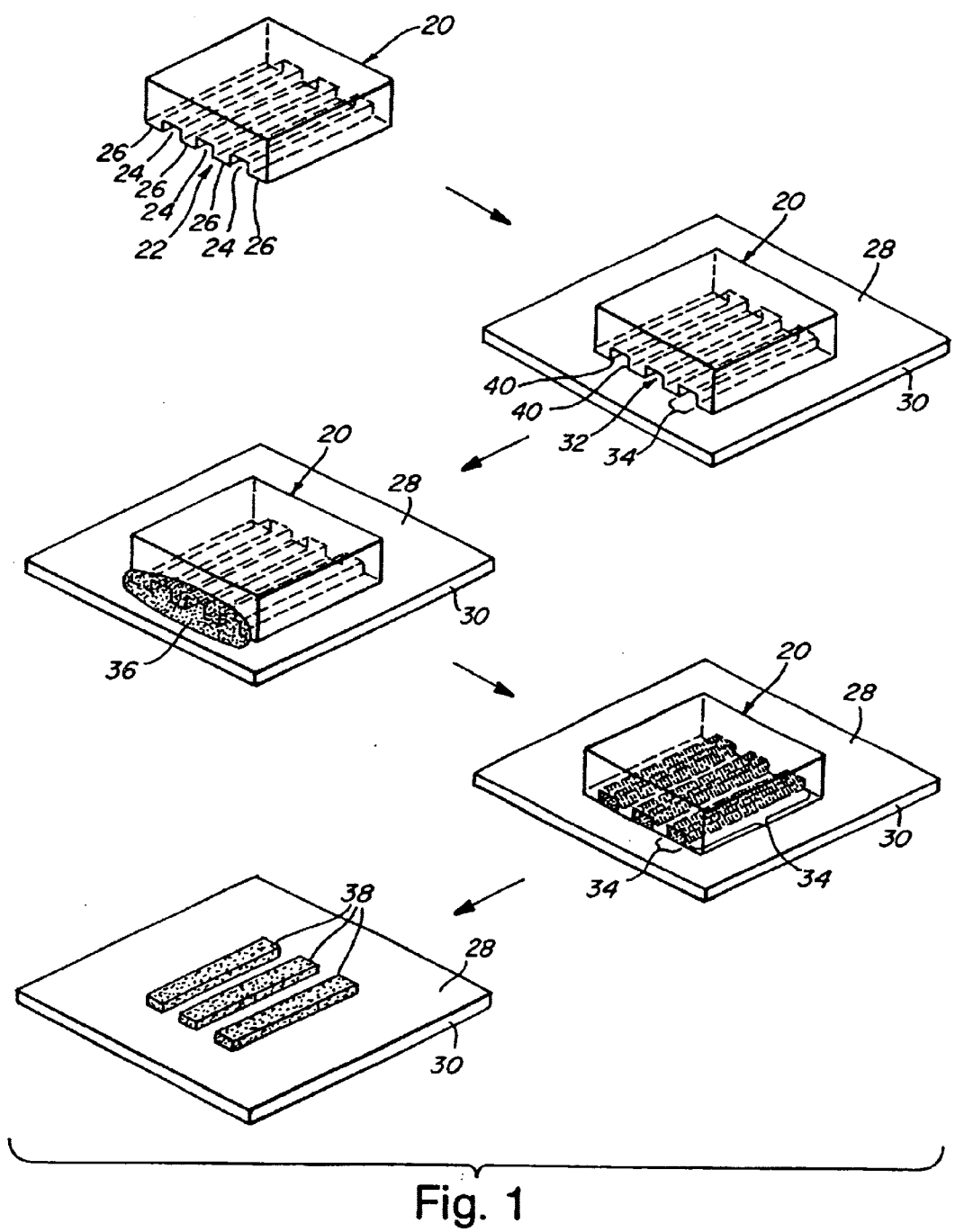

FIG. 1 illustrates schematically a technique for derivatizing a substrate surface according to a pattern of, for example, a polymeric article, a pattern of microbeads optionally carrying a chemical or biochemically active species, a catalyst or other activating agent for promoting a chemical reaction such as metal plating at the surface, a fluid carrying a dissolved or suspended species to be deposited or precipitated, or the like. For purposes of illustration, the procedure schematically illustrated in FIG. 1 will be described with respect to a hardenable prepolymeric fluid that is hardened at the surface to form a patterned polymeric article. An article 20 includes an application surface 22 having formed therein a plurality of indentations 24 that together define a linear, patterned array of indentations 24 that are contiguous with a contact surface 26. Article 20, according to one embodiment, is an applicator used to transfer a species, in a pattern, to a region or regions proximate the substrate surface, or a forming article or micromold placed proximate a substrate surface and used to guide a fluid species so as to position the species in a pattern at a predetermined region or regions proximate the substrate surface. As used herein, the term "proximate" is meant to define at a substrate surface, that is, in contact with a substrate surface, or at a position near a substrate surface and fixed relative to the substrate surface. For example, if a substrate surface carries an adhesion promoter, for example a self-assembled monolayer, activity at the surface of the self-assembled monolayer is intended to mean activity proximate the substrate surface. When forming article 20 is placed proximate a surface 28 of a substrate 30, contact surface 26 of the article seals portions of surface 28 that it contacts, thereby forming channels 32 defined by indentations 24 and portions 34 of substrate surface 28 not contacted by contact surface 26. In this manner a micromold is created, which is defined by article 20 and substrate surface 28.

A fluid 36 that, according to the embodiment illustrated, is a precursor of a patterned, polymeric structure (but can be one of a variety of species such as a carrier of a chemically or biochemically active agent, etc., as described herein) is placed adjacent one or more openings of channels 32 and introduced into the channels and allowed to flow adjacent portions 34 of substrate surface 28 in register with indentations 24. Fluid precursor 36 can be urged to flow via, for example, pressure applied to the fluid as it is positioned so as to enter the channels, or vacuum created within the channels by, for example, connection of the outlets of the channels to a source of vacuum. Alternatively, according to one aspect of the invention, the fluid can be allowed to flow into the mold via capillary action. Capillary filling of the mold is especially useful when the mold is of very small dimension (in particular in the micro scale) and is defined herein to mean that when a fluid precursor is positioned adjacent an opening or channel 32 formed by a portion 34 of the substrate surface and an indentation 24 of article 20, the fluid precursor will flow into at least a portion of the channel spontaneously.

Subsequent to introduction of the fluid precursor into the mold defined by channels 32, the fluid precursor can be hardened before or after removal of applicator 20 from substrate surface 28 (or where the fluid is a carrier of a species to be deposited or precipitated, the fluid can dissipate, i.e., evaporate, be absorbed into applicator 20, or the like). Where the fluid is viscous enough, or is allowed to reach a particular level of viscosity, the applicator can be removed and the precursor hardened at the surface without unacceptable loss of dimensional integrity. In particularly preferred embodiments, the fluid precursor is hardened to the extent that it is self-supporting (dimensionally-stable) prior to removal of Article 20 from the substrate surface.

According to one embodiment, the fluid precursor is a solution of monomer in a fluid carrier and is polymerized at the surface with article 20 in place. Article 20 then is removed. A structural article 38, in a pattern corresponding to the indentation or mold pattern 24 of article 20, results on substrate surface 28 from the described procedure. According to the description of the process illustrated in FIG. 1, structure 38 is a polymeric structure formed from a fluid prepolymeric precursor.

Where the structure 38 formed according to this embodiment is a polymeric structure, it can be thermally polymerized on substrate surface 28 via application of heat to the substrate and/or article 20 or, if article 20 is removed prior to polymerization, via convective or radiative heat; photopolymerized if substrate 30 and/or article 20 are transparent to radiation, or subsequent to removal of article 20. Free-radical polymerization can be carried out as well. These and other forms of polymerization are known to those of ordinary skill in the art and can be applied to the techniques of the present invention without undue experimentation. All types of polymerization, including cationic, anionic, copolymerization, chain copolymerization, cross-linking, and the like can be employed, and essentially any type of polymer or copolymer formable from a fluid precursor can be patterned on surface 28 in accordance with the invention. An exemplary, non-limiting list of polymers that are suitable include polyurethane, polyamides, polycarbonates, polyacetylenes and polydiacetylenes, polyphosphazenes, polysiloxanes, polyolefins, polyesters, polyethers, poly (ether ketones), poly(alkylene oxides), poly(ethylene terephthalate), poly(methyl methacrylate), polystyrene, and derivatives and block, random, radial, linear, or teleblock copolymers, cross-linkable materials such as proteinaceous material and/or blends of the above. Gels are suitable where dimensionally stable enough to maintain structural integrity upon removal of article 20 from substrate surface 28. Also suitable are polymers formed from monomeric alkyl acrylates, alkyl methacrylates, alpha-methylstyrene, vinyl chloride and other halogen-containing monomers, maleic anhydride, acrylic acid, acrylonitrile, specifically, methyl methacrylate, imides, carbonates, hexafluoroisopropyl methacrylate, acrylonitrile, bromophenyl acrylates or bromophenyl methacrylates, and the like. Monomers can be used alone, or mixtures of different monomers can be used to form homopolymers and copolymers. Non-linear and ferroelectric polymers can be advantageous. Gels are suitable where dimensionally stable enough to maintain structural integrity upon removal of article 20 from substrate surface 28. The particular polymer, copolymer, blend, or gel selected is not critical to the invention, and those of skill in the art can tailor a particular material for any of a wide variety of applications. The particular polymer, copolymer, blend, or gel selected is not critical to the invention, and those of skill in the art can tailor a particular material for any of a wide variety of applications.

According to one embodiment, a polymerizable or cross-linkable species (optionally in a fluid carrier) including an admixed biochemically active agent such as a protein can be made to form a pattern on substrate surface 28 according to the described technique. For example, carboxylated Dextran™ can carry admixed protein, be introduced into channels 34, and hardened to form articles 38. Where the Dextran™ carries admixed biologically active agent, the article can be exposed to a medium suspected of containing a biological binding partner of the biochemical agent, and any biochemical binding or other interaction detected via, for example, diffraction, or via a change in coupling between waveguide cores as described more fully below. Where article 38 defines diffraction grating, the degree of diffraction can be affected by biological binding between the biological agent compounded within article 38 and an analyte that is a biological binding partner of the compounded agent. Determination of a change in diffraction at surface 28 is indicative of the presence of analyte in the medium brought into contact with article 38. According to another embodiment, a species such as polymerizable or cross-linkable species can entirely coat surface 28, article 20 can be placed adjacent surface 28, a biological agent can be introduced into channels 34 and allowed to admix with the polymerizable or cross-linkable species, and prior to or subsequent to removal of article 20 species on surface 28 can be polymerized or cross-linked. In this manner, a surface having a pattern of biological agent compounded therein is produced, and can serve as a sensor for a biological binding partner of the biological agent via change in refraction or diffraction of light at the surface.

Where electrical conductivity is desired, an electrically-conductive polymer can be selected, and this can have significant application in the microelectronics industry, as would be recognized by one of ordinary skill in the art.

The invention is intended to encompass creation of a wide variety of structures or patterns of species on substrate surfaces from fluid precursors. The precursor can be any fluid that can flow into the mold defined by indentations 24 and portions 34 of substrate surface 28, and those of ordinary skill in the art can determine, without undue experimentation, which fluids will readily flow into such a mold based upon dimension of the mold and viscosity of the fluid. In most instances, the viscosity of the fluid can be adjusted, by for example diluting or concentrating the fluid, to achieve a level of viscosity suitable for flow into the mold at a desired rate. The polarity of the fluid can be tailored as well, with reference to the chemical characteristic of the substrate surface or micromold, to facilitate fluid carrier flow.

According to one embodiment of the invention, patterned article 38 is not a polymer or cross-linked organic species as described above, but is a non-polymerized organic species that is dissolved or dispersed in a fluid carrier to form fluid precursor 36 which is introduced into mold channels 32, whereupon the fluid carrier or solvent dissipates (e.g., is removed via evaporation from the mold channels and/or absorption into the substrate or applicator 20). According to yet another embodiment, patterned structure 38 is an inorganic structure, such as a salt or ceramic. A salt soluble in a fluid precursor can be prepared as a solution 36 defining a fluid precursor that is introduced into mold channels 32 and precipitated as a patterned salt structure 38 by removal of solvent via evaporation, adsorption, or other physical or chemical change to the surrounding environment. Inorganic salts or ceramics can be carried as a suspension in a fluid carrier, flowed into channels 32, and precipitated or deposited. Metals, such as those commonly deposited from pastes in accordance with thick-film silk-screening techniques, can be applied to defined regions of substrate surface 28 where a paste is sufficiently fluid, or the paste and/or metal can be carried in a fluid as a suspension or sol in fluid precursor 36. Those of ordinary skill in the art will recognize that a wide variety of non-electrically conductive, electrically semiconductive, and electrically-conductive structures can be patterned proximate a substrate surface according to the inventive technique. Fluid precursors of inorganic materials, such as solutions from which materials can be precipitated, or suspensions from which a fluid carrier can be removed by dissipation or evaporation, can be used to form structures, such as waveguides, from materials such as $TiO_2$, $TiO_2/SiO_2$, ZnO, $Nb_2O_5$, $Si_3N_4$, $Ta_2O_5$, $HfO_2$, $ZrO_2$, or the like. U.S. Pat. Nos. 5,009,483, 5,369,722, and 5,009,483, each incorporated herein by reference, describe many suitable precursor and waveguide materials. Dye-doped fluid precursors can be used, and are advantageous in many situations.

Another fluid precursor can be a sol-gel precursor, and sol-gel techniques known to those of skill in the art can be used to create the solid structures in patterns, according to the invention. Ferroelectric and electrooptic materials and sol-gel processing of a variety of precursors to form a variety of species is well known to those of ordinary skilled in the art and can be applied and exploited by the method of the invention. For example, materials such as $PbScTaO_3$, (Pb, La)$TiO_3$ (PLT), $LiNbO_3$, $KNbO_3$, $LiTaO_3$, potassium diphosphate, potassium triphosphate, $PbMoO_4$, $TeO_2$, $Ta_2O_5$ $BaTiO_3$, BBO crystals, $Ba_{1-x}Sr_xTiO_3$, Pb(Zr, Ti)$O_3$, $SrTiO_3$, bismuth strontium tantalate, and the like. Other examples of sol-gel precursors that can define fluid precursors of the invention include precursors of multicomponent glasses or ceramics containing at least one oxide, such as silicate glasses or ceramics containing the oxides of aluminum, boron, phosphorus, titanium, zirconium, sodium, etc. . . . Other sol-gel precursors appropriate for use are precursors of hybrid materials or organically modified ceramics, such as precursors of silicon oxycarbide or ORMOCERs. Other sol-gel precursors appropriate for use are described by Brinker and Scherer, in *Sol-Gel Science*; Academic Press, San Diego, 1990; Dislich, *Transformation of Organometallics into Common and Exotic Materials*; Nijhof, Dordrecht, 1998, volume 141; Pani, et al., *J. Am. Ceram. Assoc.*, 1994, 77, 1242; Ramamurthi, et al., *Mat. Res. Soc. Symp. Proc.*, 1992, 271, 351; Peiying, et al., *Sensors and Actuators*, 1995, A49, 187; Rao, *J. Electrochem. Soc.*, 1996, 143, 189; Li, et al., *Solar Energy Materials and Solar Cells*, 1995, 39, 179, each of which is incorporated herein by reference. Where a sol-gel precursor is used, a hydrolysis and polycondensation reaction takes place, preferably a two-step reaction. The working examples described herein use tetramethylorthosilicate as the main constituent in glasses formed according to this reaction. Other alkoxides react similarly. Sol-gel precursors that include mixtures of glasses or glasses that are mixtures of compounds. These structures can be deposited in any pattern that corresponds to an indentation pattern formable in an applicator or micromold 20 and can include dimensions through a wide range as described below.

The present invention, according to one aspect, involves the fabrication and use of reactive ion etch masks from sol-gel precursors. Dielectric materials such as aluminia, zirconia, and silica glasses and mixed glasses such as aluminosilicates can be fabricated simply, conveniently, and relatively inexpensively using the techniques of the invention. A sol-gel precursor can be formed into a pattern using any of the molding techniques as described herein, with reference for example to FIGS. 1, 2, 8, 10, 15, 16, and 25, and can be carried out directly on surface that is desirably etched via reactive ion etching. That is, an article is provided that is desirably etched via reactive ion etching, and a reactive ion etch mask is formed on a surface of the article via molding according to any of the techniques described herein from a precursor of a reactive ion etch mask. The reactive ion etch mask is formed from the precursor using the mold defined in part by the forming article of the invention on a first portion of the article surface, in a pattern, while leaving a second portion of the substrate surface free of the mask material. The surface of the article then is exposed to reactive ion etch conditions (known to those of ordinary skill in the art, e.g., $O_2$ plasma), and etching takes place at the second portion of the substrate surface. Typically, the first portion of the substrate surface will be a pattern of separated lines or portions that can be isolated or interconnected, and the second portion will be complementary to the first portion. The second portion is "free" of reactive ion etch mask when the second portion contains no reactive ion etch mask material or is covered by so little reactive ion etch mask material that exposure to reactive ion etching conditions causes reactive ion etching at the second portion.

Formation of dielectric, or ceramic materials in accordance with this aspect of the invention can find use not only in reactive ion etching masks but in integrated optics, non-linear optics and other microelectronic arenas as would be understood by those of ordinary skill in the art.

According to yet another embodiment, a biologically active agent can be dissolved or suspended in a fluid carrier as a fluid precursor 36 and introduced into channels 32 adjacent portions 34 of surface 28 and, prior or subsequent to removal of micromold 20, allowed to engage in a biochemical interaction proximate regions 34 of substrate surface 28. For example, a biochemical agent can include a biotin linker while substrate surface 28 carries immobilized avidin, and biochemical interaction can be allowed to take place at regions 34 of substrate surface 28 in this manner, linking the biochemical agent to the substrate surface at regions 34. Biochemical agents can be immobilized proximate regions 34 of the substrate surface according to other techniques as well. For example, where substrate surface 28 exposes a hydrophobic functionality, a biological agent such as a protein can be non-covalently immobilized at regions 34 of the substrate surface. To control orientation of a protein or other biochemical agent immobilized at a substrate surface via hydrophobic interaction, a hydrophobic chemical moiety can be coupled to the biochemical agent at a region of the agent remote from its active site. In this manner, the agent can be hydrophobically coupled to the surface and maintain exposure, away from the surface, of its biochemically active region. One of ordinary skill in the art can conduct a simple test to determine whether a biochemical agent is suitable for use with the described technique. The binding constant of a candidate biochemical agent for a target species can be determined using standard ELISA techniques. Then, the candidate biochemical agent can be hydrophobically immobilized (or immobilized in any other manner described herein or known to those of ordinary skill in the art, for example via a polyamino acid tag coupled to a metal ion immobilized at the surface by a chelating agent) at a variety of surfaces, and then assays can be performed to determine whether the agent has retained its ability to biologically bind to the target species or has been denatured and is unable to bind (this exemplary test is particularly useful in connection with biological agents that, in their native form only, bind target species, but when denatured do not bind the target species).

Biochemical recognition can be exploited in immobilization of a particular biochemical agent desirably patterned on substrate surface 28. For example, a first agent can be immobilized (for example using hydrophobic coupling) at regions 38 of the substrate surface, and a second agent (which is a biological binding partner of the first agent) then can be immobilized at regions 34. The second step in which the desired agent is immobilized at regions 34 can be carried out with or without micromold 20 proximate the substrate surface. Biochemical recognition involving partners also can be exploited to trap biological agents at regions 34 of the substrate surface using other biological agents that have been immobilized at regions 34. Biochemical recognition involving partners such as antibody/antigen, antibody/hapten, enzyme/substrate, enzyme/inhibitor, enzyme/cofactor, biotin/avidin, binding protein/substrate, carrier protein/substrate, lectin/carbohydrate, receptor/hormone, receptor/effector, complementary strands of nucleic acid, repressor/inducer, and the like can be exploited in connection with the technique. Those of ordinary skill will recognize a variety of uses for placement of such biochemically active agents at predetermined portions of a substrate surface in a pattern, for example as discussed below with reference to FIG. 14 and as disclosed in co-pending, commonly-owned U.S. Pat. No. 5,512,131 of Kumar, et al. and International Patent Application Publication No. WO 96/29629, both incorporated herein by reference.

According to embodiments in which the biochemical activity of a biologically active agent can be detrimentally affected by environmental factors, a fluid carrier of the biologically active agent should be selected so as not to detrimentally affect the biochemical activity of the agent. For example, if a protein is to be patterned on the surface and used in an interaction that cannot take place (or takes place at an unacceptably low level) when the protein is denatured, a fluid carrier should be selected that does not denature the protein or otherwise detrimentally affect the biological binding interaction of the protein that is to be exploited. Additionally, a micromold 20 should be selected and/or fabricated in a manner such that the surfaces of indentations 24 that can come into contact with a biologically active agent will not detrimentally affect the performance of the agent. For example, if micromold 20 is fabricated from a material that could denature a protein, then if used with the protein the interior surfaces of indentations 24 can be chemically altered, for example via grafting with polyethylene glycol, to render the surfaces non-destructive of the agent.

According to yet another embodiment, fluid precursor 36 carries a suspended or dissolved chemically active agent that is an activating agent as described in a co-pending, commonly owned U.S. application Ser. No. 08/616,692 of Hidber, et al. entitled "Microcontact Printing of Catalytic Colloids", referenced above. When a fluid carrier is used in this and other embodiments, it can form part of a species or article immobilized proximate the substrate surface or can dissipate, for example via evaporation or adsorption into the applicator or substrate surface, leaving the species carried in the fluid carrier immobilized at the surface.

A non-limiting list of chemically active agents that can be patterned on a surface in accordance with the invention includes agents as described by Lando (U.S. Pat. Nos. 3,873,359; 3,873,360; and 3,900,614) which can render a substrate surface amenable to metal plating, catalytic activating agents such as finely distributed metal particles and clusters such as conventional metal powders, substrate-fixed metal clusters or multimetallic clusters that are well known as valuable heterogeneous and homogeneous catalysts in organic chemistry, inorganic chemistry, and electrochemistry, etc. With reference to the application of Hidber, et al., such agents can include those capable of being carried by an applicator, transferred from the applicator to a surface in a form in which it can effect a chemical reaction (such as a metal deposition reaction), and immobilized at the surface with a degree of adhesion and for a period of time sufficient to participate in the desired chemical reaction. As such, one class of activating agents provided in accordance with the invention are distinguished from prior art agents applied with an applicator such as a stamp, for example as disclosed by Lando (U.S. Pat. Nos. 3,873,359, 3,873,360, and 3,900,614), in that the activating agent of the present invention is in a form suitable for effecting reaction such as metal plating or catalytic action when transferred to the surface. According to preferred embodiments, further chemical reaction at the surface to convert a precursor to a suitable agent, as necessitated in the referenced prior art methods, is not required. Metal deposition reactions contemplated include electrochemical deposition and electroless deposition, generally involving reduction of a metal cation to create the metal, facilitated in part by the lowering of the electrochemical potential involved in the deposition.

Activating agents that are finely distributed metal particles and clusters, such as conventional metal powders, including substrate-fixed metal clusters or multimetallic clusters are suitable for use as activating agents in accordance with the invention, and are well known as valuable heterogeneous and homogeneous catalysts in organic, inorganic, and electrochemistry. Exemplary activating agents include one or more metals of periodic table groups Ib, IIb, III, IV, V, VI, VIIb, VIII, lanthanides, and actinides, preferably copper and any metal more noble than copper, in particular Pd, Au, Ag, Pt, and Cu. Hydrogenation catalysts for example those effective in hydrogenating olefins or aromatics, as in the partial hydrogenation of benzene to form cyclohexene, with a substrate-fixed ruthenium activating agent or bimetallic activating agent (e.g. Ru/Sn) are contemplated. Zirconium and titanium catalysts, among others, are suitable for use in the invention that catalyze polymerization, such as polymerization of olefins such as ethylene, and these are intended to form part of the invention. Other examples of catalytic activating agents include those used in Heck reactions, e.g. in the Pd-catalyzed reaction of bromobenzene and styrene to form stilbene. Activating agents that are heterogeneous catalysts are also useful as electrocatalysts in fuel cells (in particular substrate-fixed Pt and Pt/Ru clusters). Activating agents prepared according to the invention can be homogeneous catalysts, such as those used in two phase systems (for instance $H_2O$/toluene), such as e.g. betaine-stabilized Pd clusters soluble in H$_2$O. Activating agents that are embedded in polymers can be used to prepare materials for electronic, optical and magnetic applications. Suitable embedding polymers include organic polymers, such as poly-p-phenylenevinylene, polymethyl methacrylate, polysilanes, and polystyrene, or inorganic polymers, such as zeolites, silicates, and metal oxides. The well-known sol-gel process can be used to incorporate metal clusters in amorphous metal oxide materials (e.g. SiO$_2$) as activating agents.

Soluble metal clusters that are activating-agents can also be surface-deposited to prepare novel materials for applications in optics and electronics, e.g. Pd on HOPG (highly oriented pyrolytic graphite).

Particulate activating agents having particle sizes on the order of nanometers are preferred, for example particulate matter having particle size of less than about 100 nm, preferably less than about 50 nm, more preferably less than about 25 nm, and most preferably from about 2 to about 20 nm. The size of the particles is not critical except to the extent that where excellent edge resolution of a structure deposited in a reaction involving the particle is desired, the upper limit in size of the particle is reduced.

Especially preferred as activating agents in accordance with the invention are colloidal activating agents. As used herein, colloidal activating agent is meant to define particulate matter capable of being involved in a desired chemical reaction, such as a catalytic reaction and including plating of metal at surfaces, that is carried or surrounded by molecules that prevent agglomeration of the individual particles and that render the particulate soluble in, or at least able to be carried in, an organic or aqueous liquid. Suitable colloid-forming species and colloids are described in European patent publication no. 672765 by Reetz et al., published Sep. 20, 1995, and incorporated herein by reference. According to one embodiment the activating agent comprises one or more metals of groups Ib, IIb, III, IV, V, VI, VIIb, VIII, lanthanides, and/or actinides of the periodic table prepared by cathodic reduction in the presence of a stabilizer. One method of preparation of such colloids is reduction, optionally with a supporting electrolyte, in organic solvents or in solvent mixtures of organic solvents and/or water within a temperature range of between about −78° C. and about 120° C. to form metal colloidal solutions or redispersible metal colloid powders, optionally in the presence of inert substrates and/or soluble metal salts of the respective metals. These colloids are soluble or redispersible in a suitable fluid that facilitates their application to an applicator such as a stamp. The following articles, incorporated herein by reference, describe as well exemplary activating agents suitable for use in connection with the invention. Vargo, et al., "Adhesive Electroless Metallization of Fluoropolymeric Substrates" *Science*, 262, 1711–1712 (Dec. 10, 1993); B önnemann, et al., "Preparation and Catalytic Properties of NR$_4^+$ Stabilized Palladium Colloids", *Applied Organometallic Chemistry* 8, 361–378 (1994); Reetz, et al., "Size-Selective Synthesis of Nanostructured Transition Metal Clusters" *J. Am. Chem. Soc.* 116, 7401–7402 (1994); Reetz, et al., "Visualization of Surfactants on Nanostructured Palladium Clusters by a Combination of STM and High-Resolution TEM", *Science*, 267, 367–369 (Jan. 20, 1995); and Meldrum, et al.,"Formation of Thin Films of Platinum, Palladium, and Mixed Platinum Palladium Nonocrystallites by the Langmuir Monolayer Technique" *Chem. Mater.*, 7, 111–116 (1995). Electrochemical methods are described in EP 672765, referenced above, for synthesis of soluble metal colloids by operating in an inert organic, aprotic solvent, with surface-active colloid stabilizers being added as the supporting electrolyte which will both prevent plating of the metal and protect, or stabilize, small metal nuclei in the cluster stage. A metal sheet serves as the anode to be dissolved and a metal or glassy carbon electrode serves as the cathode. After dissolution at the anode, the released metal salts are reduced again at the cathode, with tetraalkylammonium salts serving as stabilizers. Standard organic solvents can be employed.

Suitable exemplary stabilizers, or carriers, for the colloids, and at the same time as the supporting electrolyte, are quaternary ammonium or phosphonium salts R$^1$R$^2$R$^3$R$^4$N$^+$X$^-$ and R$^1$R$^2$R$^3$R$^4$P$^+$X$^-$, respectively. A wide variety of combinations of R$^1$, R$^2$, R$^3$ and R$^4$ are possible. Examples include the symmetrical tetraalkylammonium salts with R$^1$=R$^2$=R$^3$=R$^4$=n-butyl or n-octyl, mixed tetraalkylammonium salts with R$^1$=R$^2$=R$^3$=methyl and R$^4$=cetyl, or chiral tetraalkylammonium salts having four different residues. Aryltrialkylammonium salts may also be used. Suitable counter ions include various anions, e.g. halogenides (Cl$^-$, Br$^-$, I$^-$), hexafluorophosphate (PF$_6^-$), carboxylates R'CO$_2^-$(R'=alkyl, aryl), or sulfonates R''SO$_3^-$ (R''=alkyl, aryl). A similar variety of phosphonium salts may be used, including tetraarylphosphonium salts, such as tetraphenylphosphonium bromide. Preferably, tetrabutylammonium chloride, bromide or hexafluorophosphate, tetraoctylammonium bromide, or tributylhexadecylphosphonium bromide can be employed. As metals, any of those listed above, in particular transition metals such as Fe, Co, Ni, Pd, Pt, Ir, Rh, Cu, Ag, or Au, are suitable. Suitable solvents are aprotic organic solvents, such as tetrahydrofuran (THF), toluene, acetonitrile (ACN), or mixtures thereof. The temperature in the electrolytic cell may be in the range between −78° C. and +120° C., preferably 15–30° C. or room temperature.

A preferred activating agent is a colloidal catalyst that promotes deposition, for example electroless deposition, of a metal at region 34 of substrate surface 28 to which the colloidal catalyst is applied. For example, where fluid precursor 36 includes a suspension of a colloidal palladium catalyst, the fluid can be evaporated or adsorbed as described above, resulting in deposition of catalyst at regions 34 of substrate surface 28. Subsequently, an electroless copper plating bath can be introduced into channels 32 and deposition of copper allowed to take place at regions 34 of surface 28. Alternatively, micromold 20 can be removed from surface 28 and the entire surface 28 exposed to an electroless copper plating bath. Copper will plate only at those regions 34 of substrate surface 28 to which colloidal palladium catalyst had been applied. Electrochemical metal plating can be carried out as well. The chemically active agent of the invention can be any agent that can find use in chemical reaction, attraction, or other interaction proximate a substrate surface. Those of ordinary skill in the art will recognize a variety of agents that can be used in accordance with the invention, including, but not limited to solutions or suspensions of a very small species such as catalytic colloids, monomers, dissolved or suspended salts or ceramics or their precursors or other species.

According to yet another embodiment of the invention a suspension of particulate species in a fluid carrier 36 can be introduced into channels 32, followed by removal of the fluid carrier via dissipation, as discussed. The particulate species can be organic, inorganic, or polymeric material as described above, for example finely-ground polymeric, ceramic, or crystalline material, or can be in the form of microspheres. The application of microspheres in a predetermined pattern to a substrate surface can serve a variety of purposes that will be apparent to those of ordinary skill in the art upon reading the present disclosure, in light of the state of the art as set forth in several publications. An article by Lenzmann, et al., entitled "Thin-Film Micropatterning Using Polymer Microspheres", *Chem. Mater.*, 6, 156–159 (1994), incorporated herein by reference, describes formation of densely-packed monolayers of monodisperse polystyrene microspheres deposited on a glass substrate. The spheres serve as a mask for zinc sulfide deposition on the substrate as a thin film by thermal evaporation in vacuum. The mask (microspheres) are removed from the substrate surface after evaporative deposition leaving behind a surface with zinc sulfide features located in the interstitial spaces of the densely-packed spheres. For 2-micron diameter spheres, the lattice spacing of the resulting pattern is approximately 900 nanometers with individual trigonal pyramidal peaks. According to the present invention, a particular concentration of polymeric microspheres in a fluid carrier can be selected without undue experimentation that, when introduced into channels 32, followed by evaporation of the fluid carrier, would result in a monolayer of microspheres selectively patterned at regions 34 of substrate surface 28. Removal of micromold 20, followed by chemical vapor deposition, results in a well-ordered pattern of isolated, nano-scale regions of deposited material within the confines of region 34 of substrate surface 28.

An article by Dushkin, et al. entitled "Colored Multilayers From Transparent Submicrometer Spheres", *Langmuir*, 9, 3695–3701 (1993), incorporated herein by reference, discusses optical phenomena associated with polymeric beads at surfaces. Ordered multilayers are formed by evaporating the water carrier from polystyrene latex suspensions of diameter smaller than the wavelength of visible light. The spheres exhibit color when illuminated with polychromatic light. Accordingly, arrangement of a pattern of microspheres at regions 34 of substrate surface 28 in accordance with the invention can result in various radiative and colorimetric phenomena. An article by Hayashi, et al. entitled "Imaging by Polystyrene Latex Particles", *Journal of Colloid and Interface Science*, 144, 2, 538–547 (July, 1991), incorporated herein by reference, describes microarrays of identical images produced by polydispersed polystyrene particles at a surface. Microparticles and microbeads, especially polymeric particles and beads such as latex or polystyrene beads, find use in the field of biochemistry as solid supports for biochemical interaction. For example, a chemically or biochemically active agent can be coupled to a microbead or microparticle and optionally used in turn to immobilize a second agent that reacts with the immobilized agent, thereby immobilizing the second agent at a region at which the microbead is immobilized. That is, microbeads carrying a particular agent can be immobilized at a surface in a pattern using techniques of the invention and the patterned, immobilized beads can serve as locations for chemical reaction or biochemical interaction on the micro scale, for example as microreactors. Those of ordinary skill will recognize a variety of uses for patterned microparticles or microbeads carrying chemical or biochemical agents such as, for example, biochemical assays.

Figure 17:
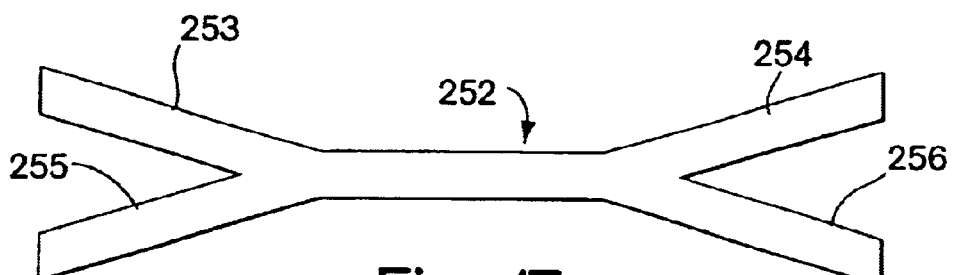
FIG. 17 is a schematic illustration of one type of prior art waveguide coupler.
Figure 18:
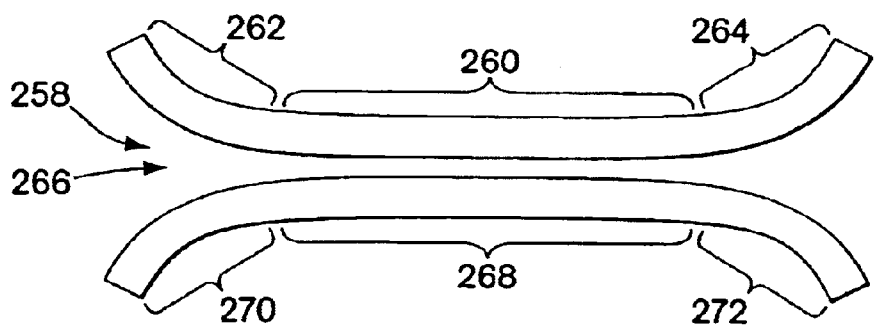
FIG. 18 is a schematic illustration of another type of prior art waveguide coupler, namely an evanescent coupler.

The pattern of parallel indentations 24 formed in surface 22 of micromold or applicator 20 is for illustrative purposes only. Any pattern, for example a pattern defined by a single indentation or many indentations, one or more of the indentations defining a non-linear pathway of uniform or non-uniform depth is intended to fall within the scope of the invention. Various patterns are illustrated in subsequent figures. The indentation pattern can be of a variety of dimensions and, according to one aspect of the invention, includes a region having a lateral dimension of less than 1 millimeter. "Lateral dimension" is meant to define a dimension parallel to application surface 22. According to preferred embodiments, the indentation pattern includes a portion having a lateral dimension of less than about 500 microns or less than about 100 microns, in one set of embodiments more preferably less than about 50, 20, or 10 microns, and more preferably still less than about 5 microns. According to a particularly preferred embodiment, an indentation pattern having a portion including a lateral dimension on the order of 1 micron is provided. The dimension of the indentations can be altered, as described in international patent publication number WO 96/29629, published Jun. 26, 1996 of Whitesides, et al., entitled "Microcontact Printing on Surfaces and Derivative Articles", incorporated herein by reference, by deforming article 20. Where waveguides are fabricated in accordance with the invention, it is an advantage that, for example, branched sections and/or evanescent coupling sections, as shown in FIGS. 17 and 18 can be included in the pattern. Those of ordinary skill in the art can select suitable dimensions, depending upon the frequency of electromagnetic radiation being guided. Typically, the waveguide will have a width on the order of microns. The technique can be carried out where micromold 20 includes an indentation pattern where the indentations have depths and widths on the order of 100 microns to less than 1 micron, controllably.

Where micromold 20 is placed adjacent a substrate surface and a fluid precursor fills channels 32, article or articles 38 resulting from the technique can have lateral dimensional features that correspond to the lateral dimensional features of indentations 32 of the micromold.

According to another embodiment, the fluid precursor need not completely fill channels 32, and this is preferred according to embodiments in which the lateral dimension of article 38 formed from the fluid precursor is to be minimized. According to this embodiment, fluid precursor 36 is introduced into channels 32 in an amount small enough that the fluid precursor wets only the corners of the channels. When a fluid precursor, substrate, and micromold are selected such that the fluid precursor will wet the micromold efficiently via capillary action, when a small amount of fluid precursor is supplied to the mold channel or channels, the precursor will selectively wet portions of the channels having an interior angle relatively low relative to the rest of the channel (such as corners 40 defined by the abutment of contact surface 26 against substrate surface 28 at the edge of region 34 of the substrate surface). When the fluid precursor wets the corners selectively and the fluid is hardened, evaporated, or adsorbed, a resulting structure can define a pattern having a dimension smaller than that of the lateral dimension of indentation 24. According to this embodiment the lateral dimension of structure 38, at its narrowest, is narrower than the narrowest lateral dimension of channel 24 of the micromold, and can have a height significantly less than the height of the channel. The lateral dimension of article 38 according to this embodiment can be on the order of less than or equal to about 100 microns or 50 microns, or preferably less than about 20 or 10 microns, more preferably less than about 5 microns or 1 micron, and according to a particularly preferred embodiment less than approximately 0.2 micron. According to this aspect, any of the species described herein that can be patterned proximate a substrate surface can be patterned so as to have lateral dimensions as described above. This aspect of the invention is illustrated in FIG. 6c, and discussed below.

In an alternate technique, any of the species described herein that can be used to form patterned articles and the like on a substrate surface (such as fluid precursor 36) can be made to coat substrate surface 28, and then article 20 can be pressed against substrate surface 28 to displace precursor 36 at regions in register with contact surface 26. Precursor 36 will be formed in channels 32 as illustrated in FIG. 1, and procedures described above carried out.

Any suitable material can define substrate 30 of the invention. Substrate surface 28 can be of the same material as the bulk material of substrate 30, or a different material. Substrates exposing a variety of functional surfaces such as hydrophobic, hydrophilic, and biologically compatible or non-compatible surfaces are known, and are suitable for use with the invention.

Substrates that are somewhat fluid are known as well, and are acceptable for use in the invention to the extent that a useful pattern can be formed thereupon. Article 20 similarly can be formed of essentially any material. For example, ceramic, polymeric, elastomeric, and other materials can be used. According to a preferred embodiment, substrate surface 28 and/or contact surface 26 of article 20 is an elastomer or other conformable material. Preferably, contact surface 26 and more preferably, for ease of fabrication, the entire article 20, is formed of an elastomer. When an elastomer defines substrate surface 28 or contact surface 26, or preferably micromold 20, an optimal seal is created between contact surface 26 and portions of substrate surface 28 adjacent and contiguous with portions 34 that with indentations 24 define channels 32. This results in optimal confinement of fluid precursor 36 to channels 32. According to the invention pressure can be applied to micromold 20 against substrate 30 during micromolding, but according to embodiments in which an elastomer is used as described, pressure need not be applied as the elastomer conforms well to the surface against which it mates thus sealing channels 32. The micromold 20 can be fabricated of an elastomer in a manner analogous to the fabrication of a stamp from an elastomer as described in co-pending, commonly-owned U.S. Pat. No. 5,512,131, issued Apr. 30, 1996 by Kumar, et al, entitled "Formation of Microstamped Patterns on Surfaces and Derivative Articles", and as described in International Patent Publication No. WO 96/29629 of Whitesides, et al., entitled "Microcontact Printing on Surfaces and Derivative Articles", published Jun. 26, 1996, both of which are incorporated herein by reference.

Figure 2:
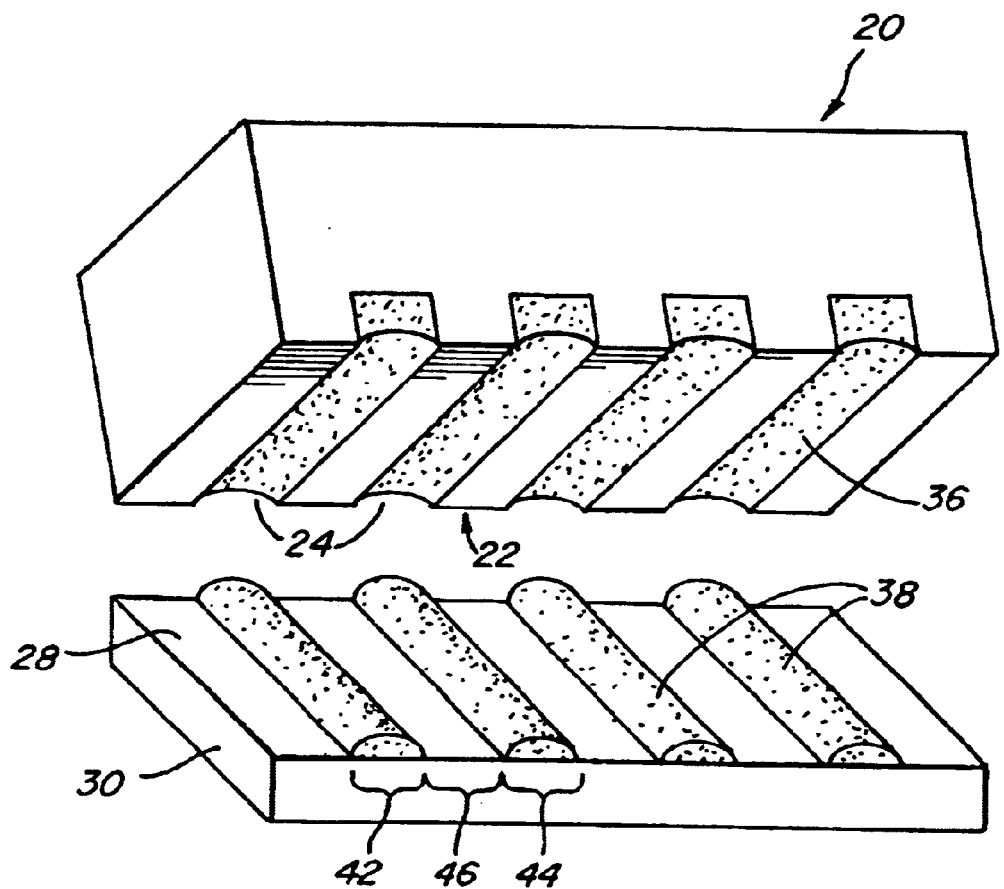
Figure 15:
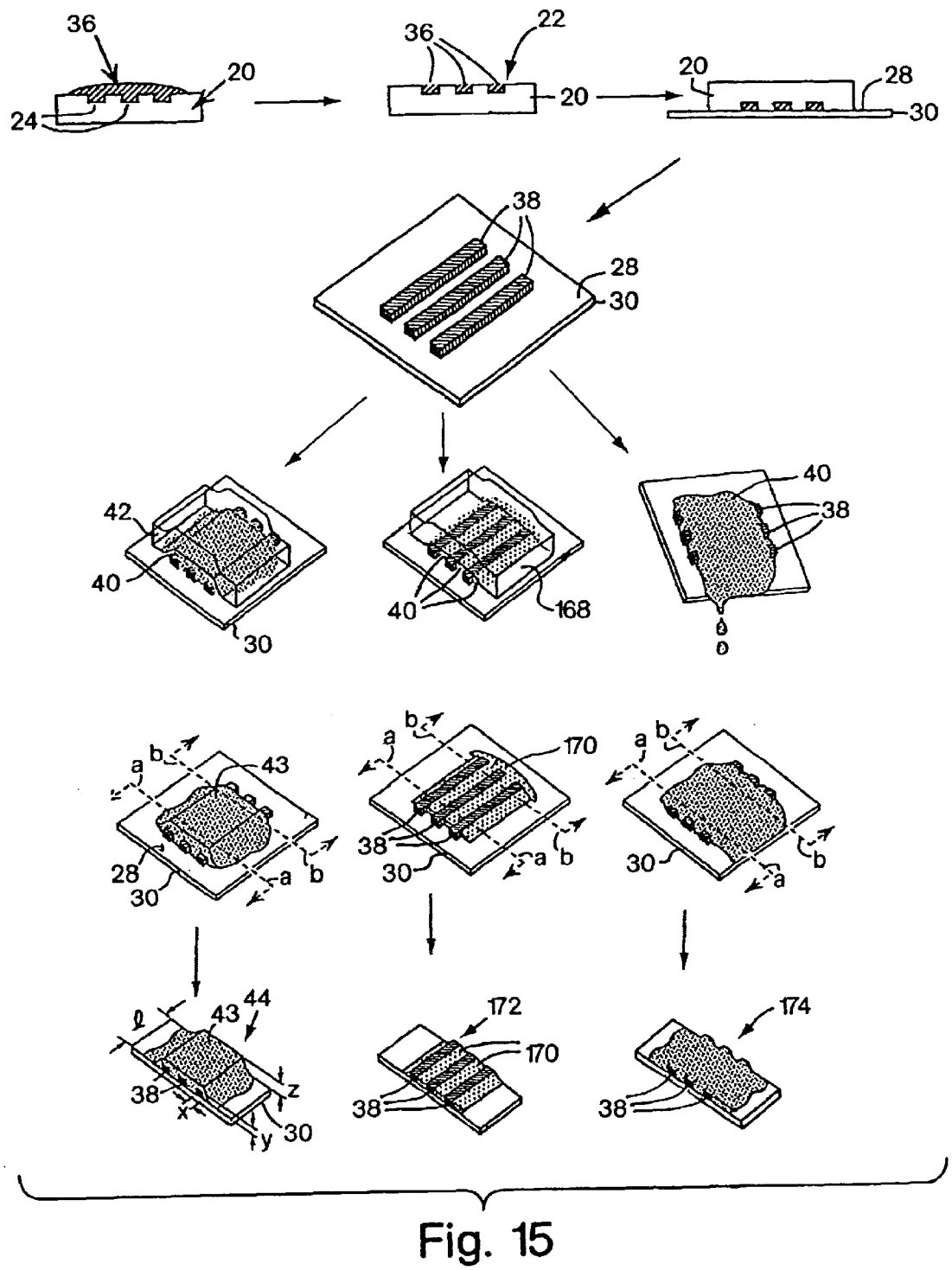
FIG. 15 illustrates schematically several techniques of the invention for forming a waveguide array or other structure, from a fluid precursor, on a substrate surface followed by formation of a cladding layer over the waveguide array.

FIG. 2 illustrates another embodiment of the invention in which, rather than applying article 20 to substrate surface 28 followed by introduction of fluid precursor 36 into channels 32 so defined, article 20 is used as an applicator to transfer a chemically or biochemically active agent (optionally in a fluid carrier), fluid precursor of an article such as microparticles or microbeads in suspension, catalytic colloid, prepolymer fluid, or the like to substrate surface 28. Described below with reference to FIG. 15 is a set of transfer molding techniques particularly preferred in the fabrication of waveguides and other articles where the final shape of the formed article is essentially identical to the shape of the interior of the mold. In FIG. 2 and subsequent figures, components common to the various figures are given common numerical designation. In FIG. 2, fluid precursor 36 is first applied to indentations 24 of micromold 20, and then application surface 22 is brought into proximity of substrate surface 28 to allow fluid precursor 36 to be transferred to substrate surface 28. The fluid precursor can be applied to the indentations by bringing the indentations into contact with the fluid precursor and allowing capillary action to cause the indentations to be filled, or the precursor can be applied via micropipetting or the like to the indentations. In this way, separate fluid species can be applied to separate indentations if desired. In can be advantageous, with these techniques, to select a material exposed by the contoured application surface and the fluid species applied thereto such that the fluid species rapidly is positioned within the indentations, rather than spreading over the entire surface. Those of skill in the art can carry out such selection, using contact angle measurements or the like.

Where fluid precursor 36 protrudes from indentations 24 prior to transfer, application surface 22 need not contact substrate surface 28 for transfer to take place. Typically, however, application surface 22 will be brought into contact with substrate surface 28 to transfer a pattern of the fluid precursor 38 to regions proximate the substrate surface in a pattern corresponding to the indentation pattern 24. As illustrated, some fluid precursor remains in indentations 24, and the fluid precursor transferred to substrate surface 28 has been converted into hardened article 38. However, according to several embodiments discussed above, the fluid precursor will not result in a hardened article, but will serve to transfer a biochemical agent or chemical agent to a surface. According to the embodiment illustrated in FIG. 2, the chemical or biochemical agent, prepolymer, fluid carrier containing a suspension of particulate matter, microbeads, or the like serves to transfer essentially instantaneously the desired species to the surface. As with all embodiments of the invention, the pattern of species so transferred can include a single indentation that is of any shape including a non-linear or linear pathway, a plurality of linear indentations as illustrated in FIG. 2, or a plurality of indentations of any shape, one or more indentations having dimensions as described above. Where a plurality of indentations are formed in application surface 22, each indentation can be made to carry a different chemical or biological agent or precursor. According to that embodiment, when application surface 22 of the micromold is brought into contact with substrate surface 28, distinct first and second species such as distinct first and second chemically or biochemically active agents, precursors, particulate species, or the like can be transferred essentially instantaneously to distinct first and second regions 42 and 44 proximate the substrate surface, in a pattern corresponding to the indentation pattern, and separated from each other by intervening region 46 of the substrate surface that remains free of the agent or precursor.

Figure 3A:
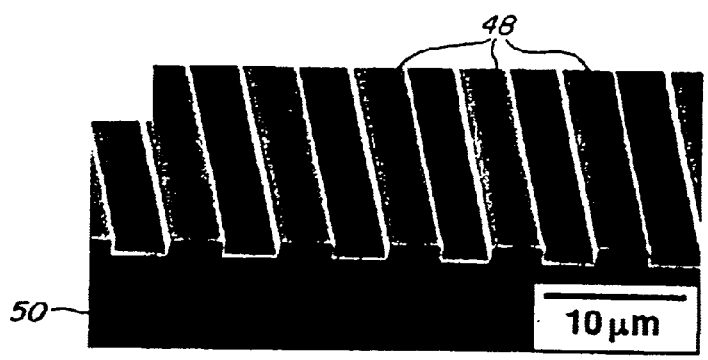
Figure 3B:
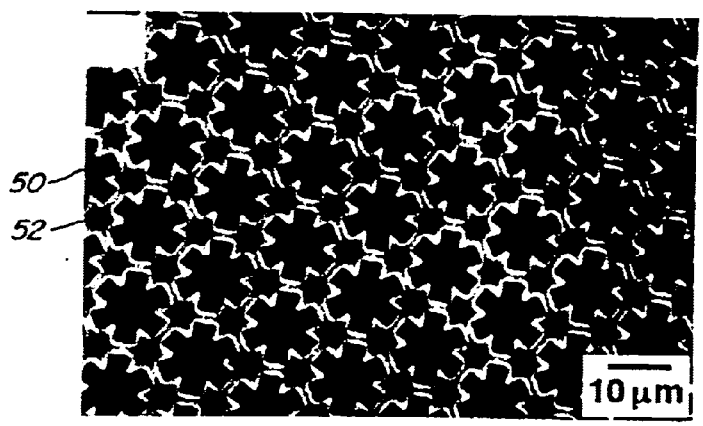
Figure 3C:
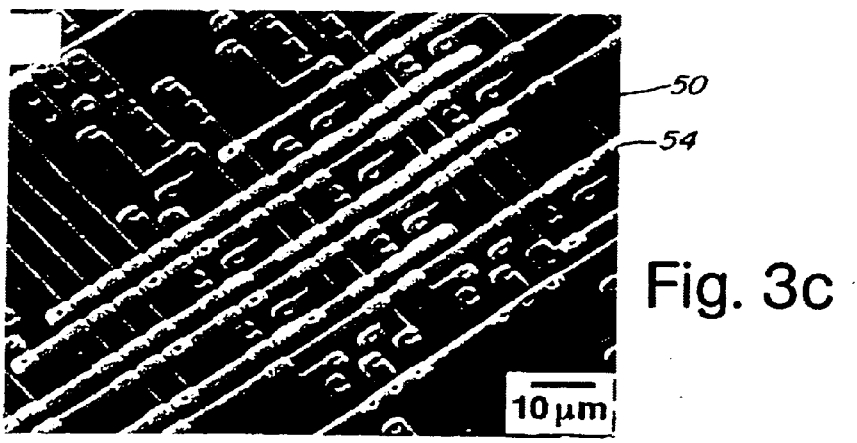
Figure 3D:
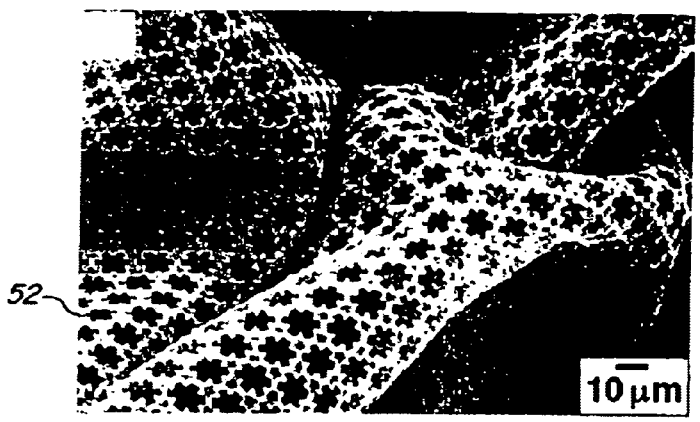

FIGS. 3a–d are photocopies of SEM images of polymeric structures formed on substrates according to the method described above and illustrated in FIG. 1, in which a fluid polymeric precursor was allowed to fill channels formed by indentations in micromold 20 and regions of the substrate. FIG. 3a shows polyurethane articles 48 formed on Si/SiO$_2$ substrate 50 by capillary filling of a micromold having a surface with indentations placed adjacent substrate 50. The indentations correspond to the pattern of articles 48. A liquid polyurethane prepolymer was placed adjacent openings of channels formed between the micromold and the substrate surface and filled the channels via capillary action. The micromold was made of polydimethylsiloxane (PDMS). FIG. 3b is a top view of a polyurethane article 52 having a complex, interconnected pattern formed on Si/SiO$_2$ substrate 50. A PDMS micromold having an indentation pattern corresponding to the pattern of article 52 was used, and a liquid polyurethane prepolymer was allowed to fill the mold channels via capillary action. FIG. 3c shows a quasi three-dimensional array of microstructures interconnected through channels. Again, a polyurethane liquid prepolymer was allowed to fill channels formed by a micromold having an indentation pattern corresponding to the pattern of polyurethane article 54. Polyurethane article 54 is formed on a Si/SiO$_2$ substrate 50. FIG. 3d shows a free-standing patterned polyurethane article 52 formed by removal of the article from the substrate (FIG. 3b).

Figure 4A:
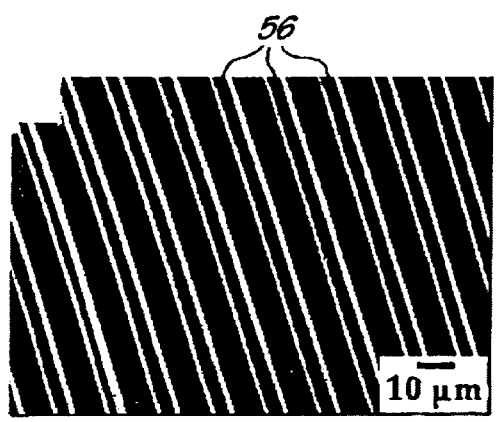
Figure 4B:
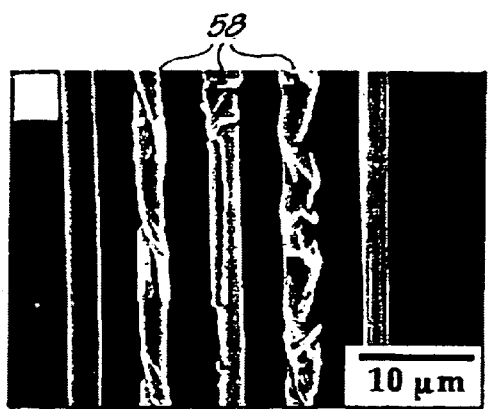
Figure 4C:
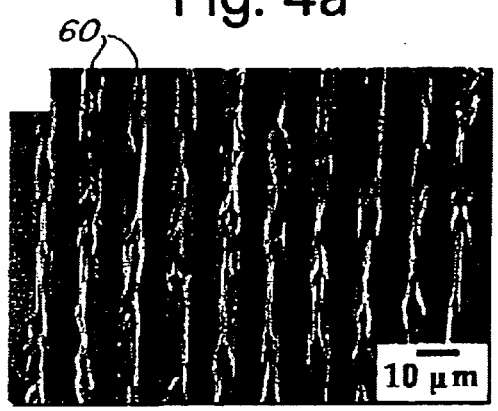
Figure 4D:
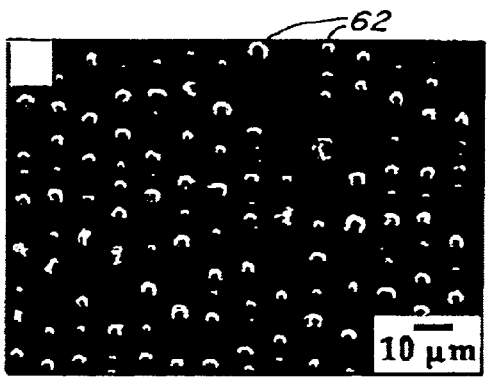
Figure 4E:
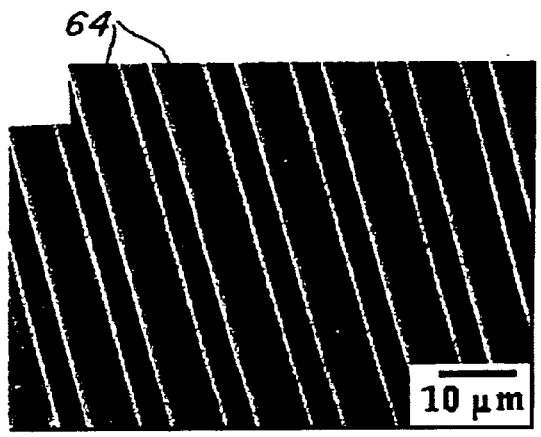
Figure 4F:
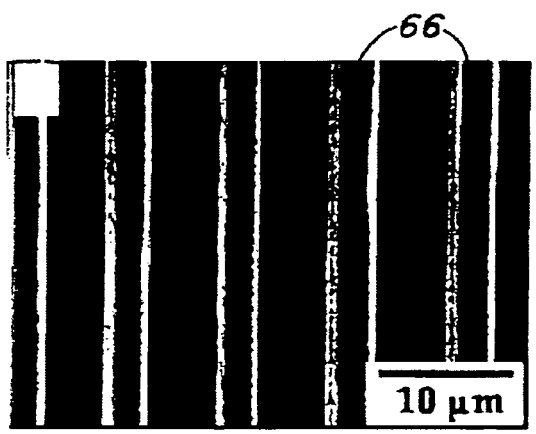
Figure 4G:
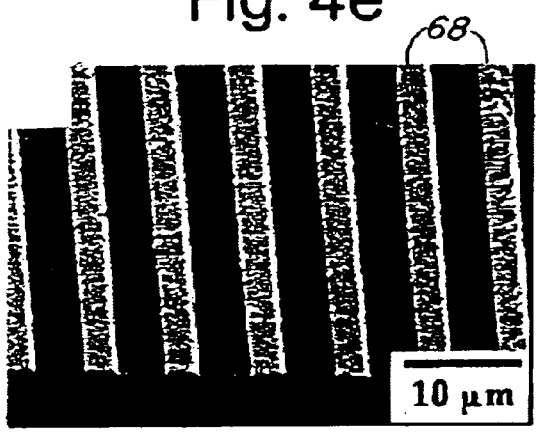
Figure 4H:
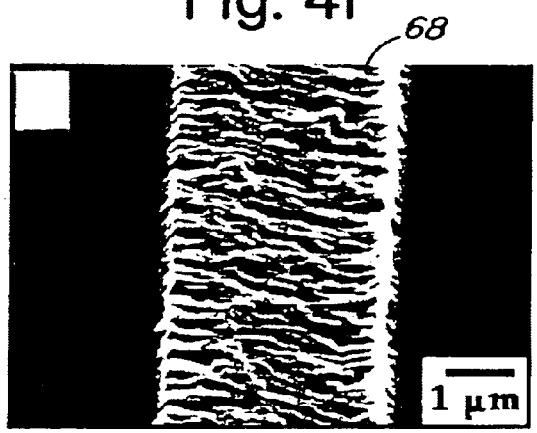

FIGS. 4a–h illustrate structures formed on substrates using the micromolding technique illustrated in FIG. 1 in which liquid precursor 36 is a precursor of inorganic materials. Photocopies of SEM images are shown. In FIG. 4a, KH$_2$PO$_4$ structures precipitated from aqueous solution on Si/SiO$_2$ are shown. FIG. 4b shows KH$_2$PO$_4$ structures as well, crystallized more rapidly. FIG. 4c shows Cu(NO$_3$)$_2$ on the same substrate crystallized from aqueous solution. FIG. 4d shows structures formed of the same material on the same substrate, but crystallized from a much more dilute solution. FIG. 4d illustrates the derivatization in a pattern that is formed within the boundaries of a region of the substrate surface corresponding to the indentation pattern of the micromold, but that does not fill that region. A series of isolated regions of product on the order of 4 microns in lateral dimension are shown. FIG. 4e shows CuSO$_4$ structure on glass. FIG. 4f shows K$_3$Fe(CN)$_6$ structures on Si/SiO$_2$. FIG. 4g shows a fractured view of amaranth on glass. The structures are approximately 0.4 micron in height. FIG. 4h is a section of FIG. 4g at higher magnification.

Ceramic structures formed in accordance with the invention can find use, for example, as mechanical ceramics such as abrasion tools. Current methodologies involve, typically, chemical vapor deposition to form ceramic patterns having small dimensions for such uses.

Figure 5:
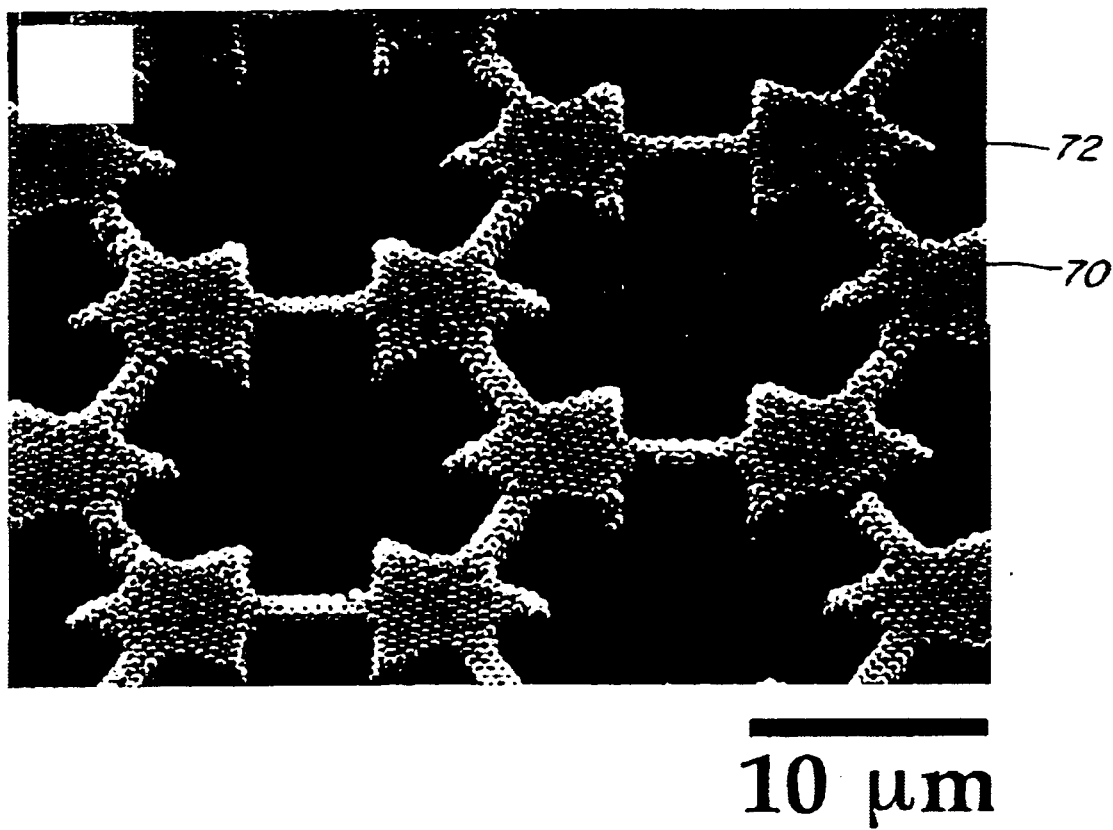

FIG. 5 is a photocopy of an electron micrograph showing a packed, ordered array of polystyrene microspheres 70 on a Si/SiO$_2$ substrate 72. The ordered array of microspheres was formed by allowing a latex solution containing polystyrene microspheres to fill, via capillary action, channels formed between a micromold and the substrate surface in a pattern corresponding to the pattern of microbeads shown. The PDMS micromold was removed following crystallization of the microspheres via dissipation of the fluid carrier.

Figure 6A:
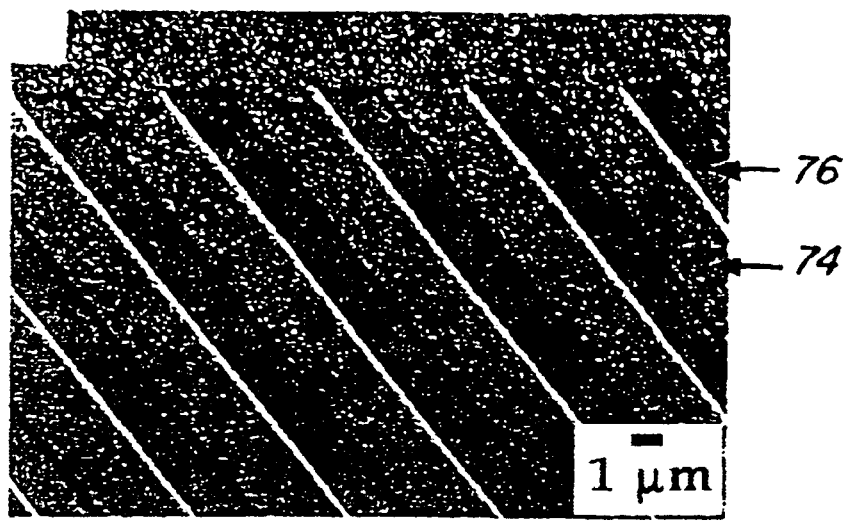
Figure 6B:
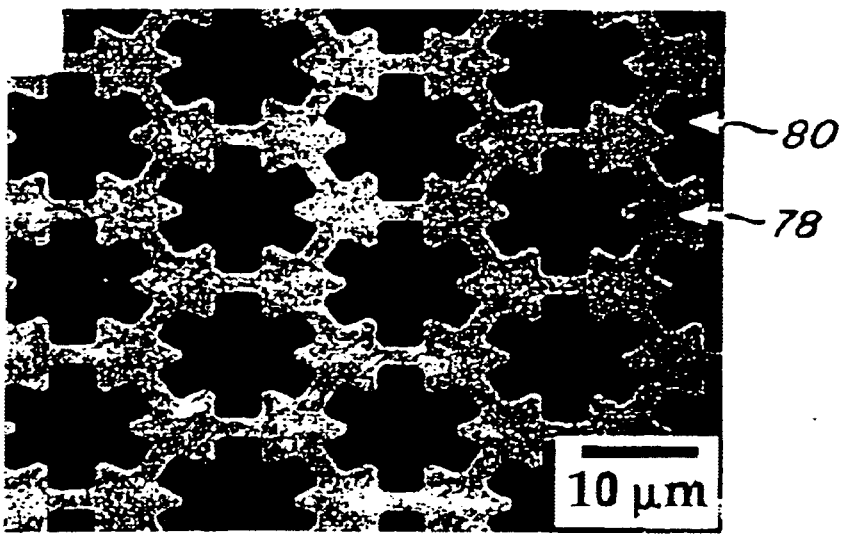
Figure 6C:
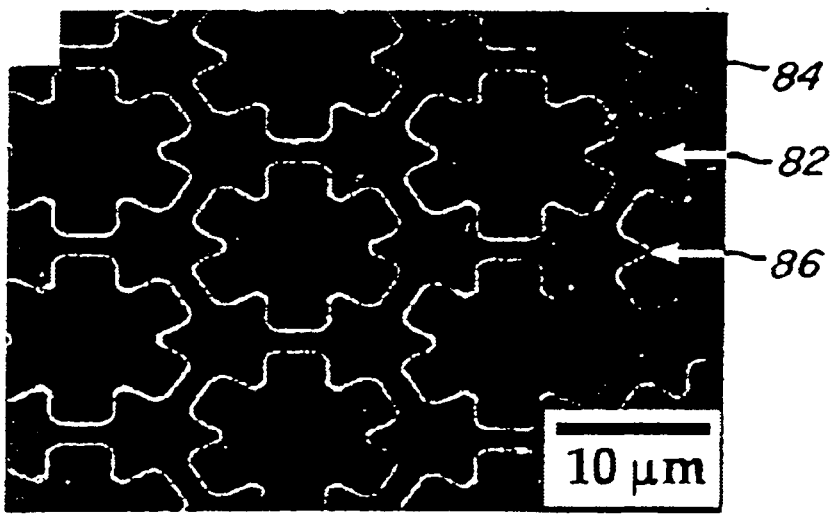
Figure 7A:
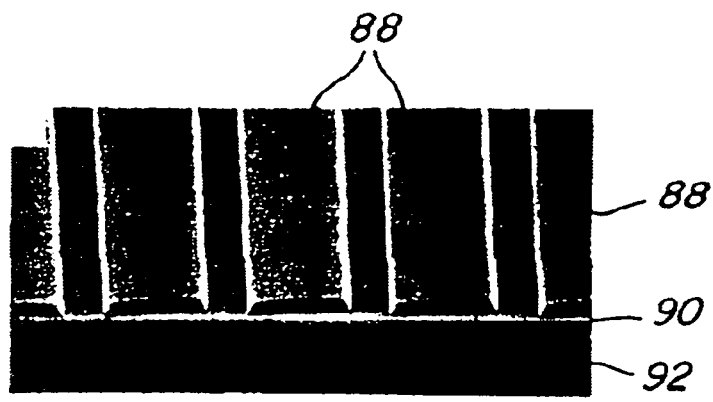
Figure 7B:
Figure 7C:

FIGS. 6a–c are photocopies of SEM images of copper structures formed via electroless deposition on Si/SiO$_2$ substrates. For the structure in FIG. 6a, a gold surface was provided. A PDMS micromold having an indentation pattern corresponding to the pattern of copper structures illustrated was placed adjacent the gold substrate (as illustrated schematically in FIG. 1) and the channels 32 were filled with a plating bath for electroless deposition of copper, defining a fluid precursor of copper according to one aspect, and a chemically active agent according to another aspect. The copper electroless plating solution was allowed to remain in contact with the surface for a period of time sufficient to plate copper structures 74 in a pattern corresponding to the indentation pattern of the micromold, while portions of gold surface 76 corresponding to contact surface 26 of the micromold remained free of copper deposition. For the structure illustrated in FIGS. 6b–c, a PDMS micromold having an indentation pattern corresponding to the pattern of copper structures illustrated was placed adjacent the substrate and the channels 32 were filled with a precursor solution 36 containing catalytic colloids. The solvent in which the catalytic colloids dissipated, resulting in formation of the catalytic colloids as a chemically active agent formed on regions of the substrate surface corresponding to the indentation pattern of the micromold. The micromold was removed, and the surface exposed to an electroless copper plating bath. Specifically, in FIG. 6b, copper structures 78 were formed on a Si/SiO$_2$ substrate 80 coated with a self-assembled monolayer of siloxane on the Si/SiO$_2$ substrate. CH$_3$CH$_2$O)$_3$Si(CH$_2$)$_3$NH$_2$ defined the self-assembled monolayer. A micromold having an indentation pattern corresponding to the ultimate copper pattern 78 was placed on the self-assembled monolayer-derivatized silicon substrate. A DMF solution containing palladium colloids as a fluid precursor 36 was allowed to fill the channels. Dissipation of DMF resulted in the chemically active agent (specifically, palladium colloid) forming structures in a pattern corresponding to pattern 78. The substrate was exposed to an electroless copper plating bath to plate copper at patterned region 78. FIG. 6c illustrates an aspect of the invention in which articles of very small lateral dimension can be formed by allowing a small volume of fluid precursor 36 to enter channels 32 defined by the micromold indentations and the substrate surface. The substrate was prepared as described in connection with FIG. 6b. A region 82 of the substrate surface corresponds to the indentation pattern of the micromold. The fluid precursor 36 wetted only the corners defined between the substrate surface 84 and the micromold channels thus, when the fluid carrier dissipated, the catalytic colloid was solidified only in those portions of the indentation pattern that were wetted, namely, the corners. When the surface was exposed to an electroless copper plating bath, copper was plated at the regions 86 to which the catalytic colloid had been deposited. A copper pattern of very small lateral dimension resulted. FIGS. 7a–c illustrate the application of a patterned structure to a surface from a fluid precursor using micromolding as illustrated in FIG. 1, followed by use of the structure as a resist in a chemical etch. A polymeric structure 88 (polyurethane) was formed from a fluid prepolymer in a pattern corresponding to an indentation pattern on a 200 nm, thermally grown oxide layer 90 of a silicon substrate 92 (FIG. 7a). Following exposure of the substrate to a solution (aqueous HF/NH$_4$F for about 2 minutes) that etches silicon dioxide, but to which the polymeric structure 88 was resistant, the silicon dioxide layer was removed at regions of the substrate intervening the regions covered by the patterned structure 88, that is, regions that had been contacted by contact surface 26 of the micromold (FIG. 7b). Subsequently, the substrate surface was exposed to a solution (400 ml H$_2$O, 92g KOH, 132 ml 2-propanol for about 15 minutes at 65° C.) that etches silicon, but to which silicon dioxide is resistant. FIG. 7c shows resultant channels 94 anisotropically etched in the silicon substrate between patterned regions of silicon dioxide 90 that correspond to the pattern of polymeric structure 88 formed on the substrate surface via the micromolding technique.

Figure 8:
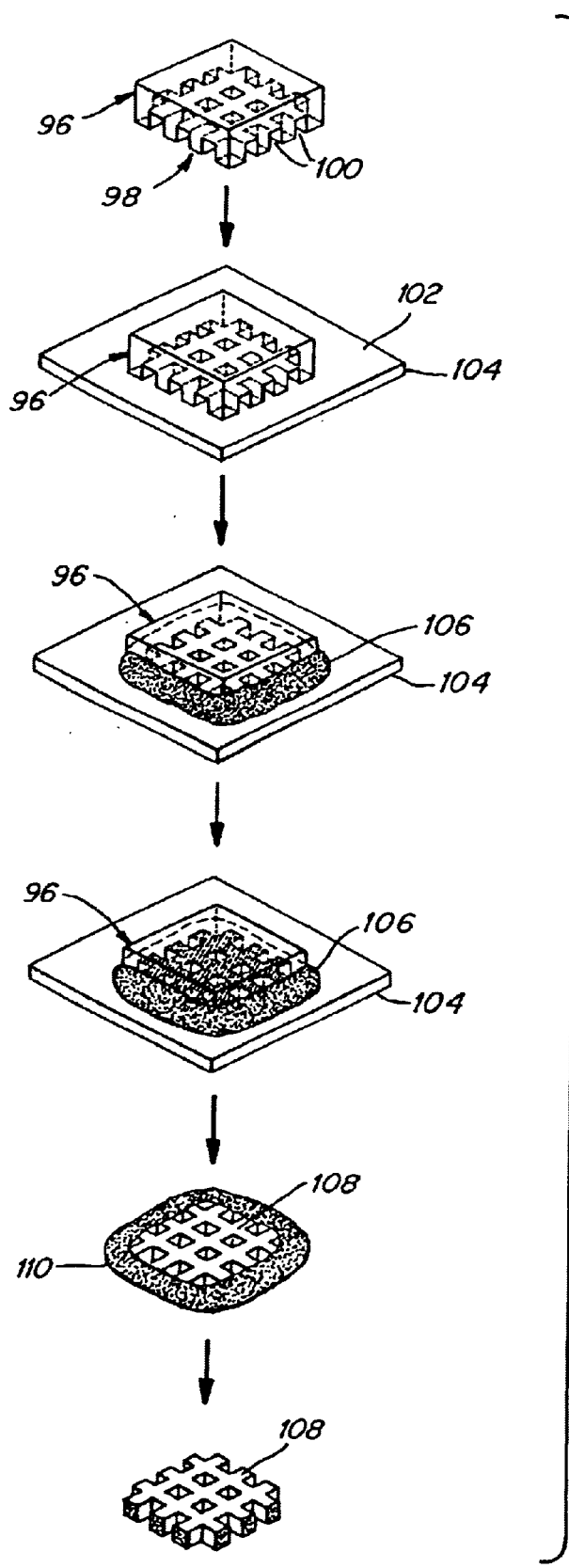

FIG. 8 illustrates schematically a technique for forming a mask, for use in lithography or the like, via the micromolding technique of the invention. A micromold 96 having a molding surface 98 including a plurality of indentations 100 in a grid-like pattern is applied to a surface 102 of a substrate 104. A fluid polymeric precursor 106 is placed adjacent openings of channels formed between the substrate surface and the indentations of the micromold, and allowed to flow, via capillary action, into the channels. Where a PDMS micromold was used, the polymeric precursor could be placed so as to cover all channel openings, and flowed into and made to fill. the channels completely. Gas escaped presumably via diffusion through the micromold. Once the polymeric precursor was hardened, via thermal or photolytic polymerization or the like, the micromold was removed. The substrate then was separated from the resultant patterned article 108. The patterned article had a "frame" 110 completely surrounding it which could be used for ease of manipulation. The frame could be removed as well, to form the article 108 in a pattern corresponding to the indentation pattern of the micromold free of the frame.

Figure 9A:
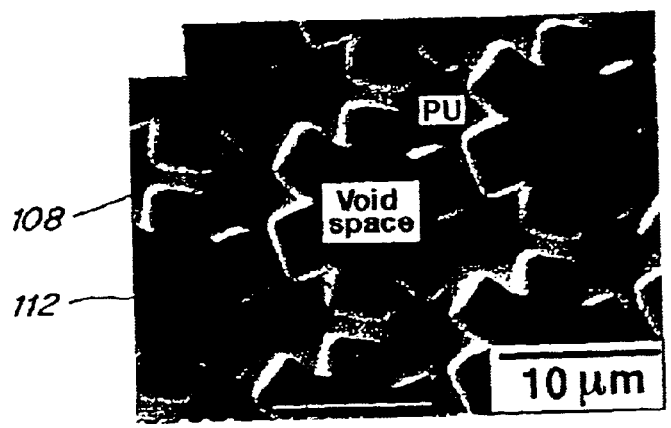
Figure 9B:
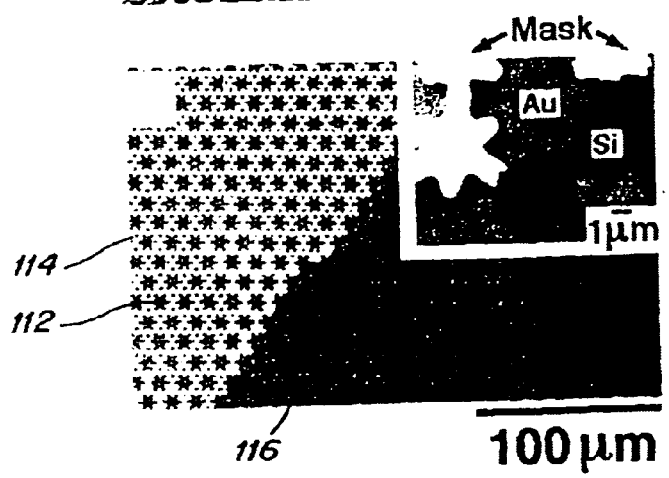
Figure 9C:
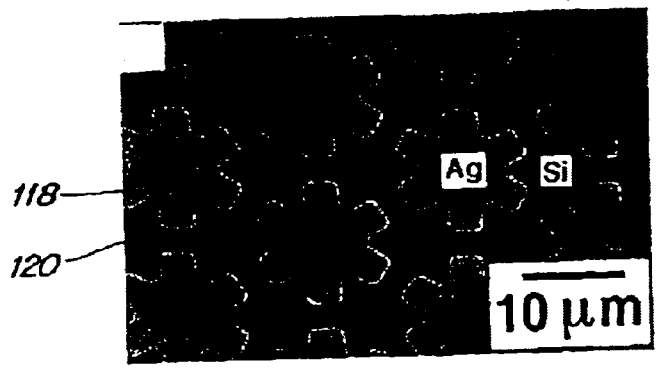
Figure 9D:
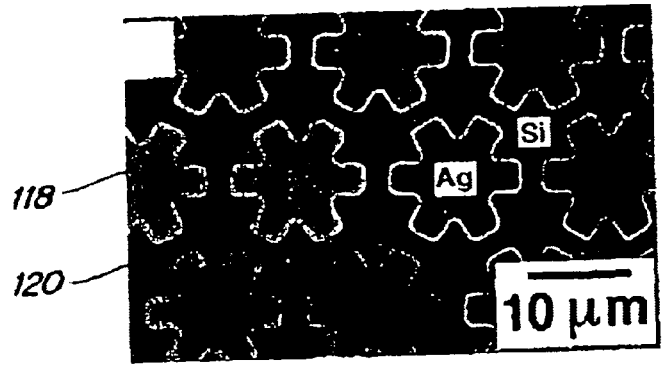

The article 108 could be used as a mask, for example as illustrated in FIGS. 9a–d, which are photocopies of SEM images. FIG. 9a shows a polyurethane mask 108 formed as illustrated in FIG. 8, and following formation placed on a Si/SiO$_2$ substrate 112. FIG. 9b shows the mask 108 on the substrate 112 following evaporation of gold onto the substrate. A portion of the mask was removed and mask 114 and portions 112 of the substrate not covered by the mask are shown covered with gold. Portions 116 of the substrate that had been covered by mask 108 remain free of gold. FIG. 9c shows a surface having a pattern of isolated regions 118 of gold on a silicon substrate (regions 120 of the silicon substrate not covered by regions 118 of gold can be seen) formed as follows. A mask fabricated as described above was placed (with reference to FIG. 8) on a silicon substrate carrying a thin film of gold. A self-assembled monolayer-forming species (hexadecanethiol) was exposed to the surface and formed a self-assembled monolayer selectively at regions 118 not covered by the mask. The mask then was removed from regions 120, and the surface exposed to a solution that etched gold, but to which the self-assembled monolayer was resistant. The self-assembled monolayer then was removed, resulting in the regions 118 of gold that had been protected by the secondary, self-assembled monolayer resist, isolated by regions 120 of the silicon substrate. FIG. 9d shows a surface derivatized as described with respect to FIG. 9c, but the self-assembled monolayer was transferred to regions 118 of the surface by placing a flat PDMS article that had been coated with a self-assembled monolayer-forming species on top of the mask 108 for one minute.

Mask 108 also could be applied to nonplanar surfaces followed by plating, etching, or the like. It can be advantageous, when transferring mask 108 to a surface having very fine features, such as a surface etched as illustrated in FIG. 7c, to transfer mask 108 to such a surface by floating it in a fluid that is supported by the surface and allowing the fluid to dissipate or run off.

As described in international patent publication number WO 96/29629, published Jun. 26, 1996 of Whitesides, et al., referenced above, etching or plating at a surface can be made to take place selectively at predetermined regions, and this technique can be exploited using the techniques of the present invention as described herein. Additionally, where a self-assembled monolayer is patterned, a "protecting species" that is resistant to (for example, incompatible with) a chemical etch can be placed on top of a self-assembled monolayer, followed by etching at regions not covered by the self-assembled monolayer, as described in publication no. WO 96/29629. Of course, a self-assembled monolayer can be incompatible with an etch and etching can take place without the use of a protecting species. The protecting species, according to this embodiment, is compatible with the self-assembled monolayer. According to another embodiment, a protecting species is less compatible with the self-assembled monolayer than with the substrate surface that is exposed at regions intervening the self-assembled monolayer. According to this embodiment, after patterning of a self-assembled monolayer a protecting species is exposed to the surface and when the surface is exposed to an etchant, the surface is etched at regions that had been covered by the self-assembled monolayer.

Figure 10A:
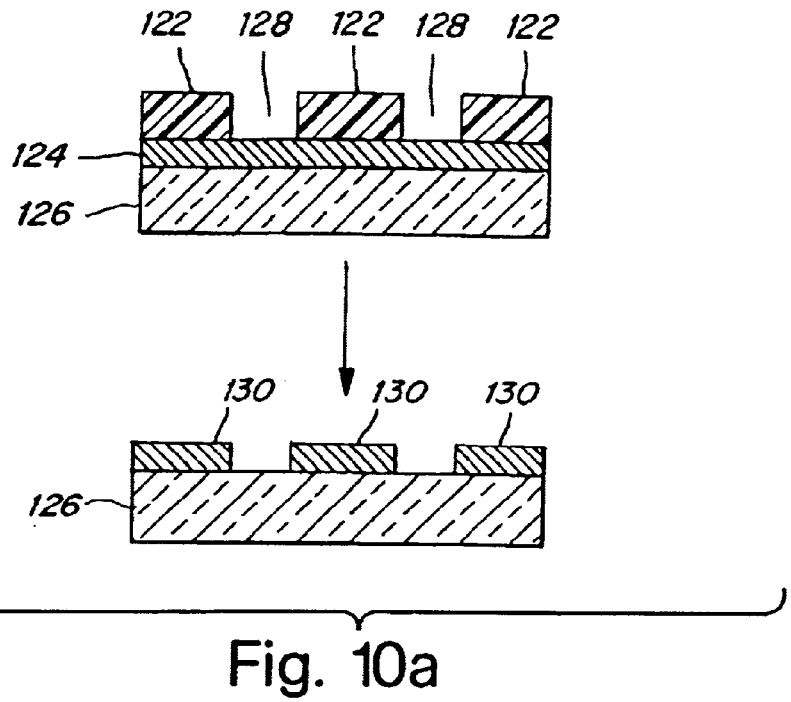
Figure 10B:
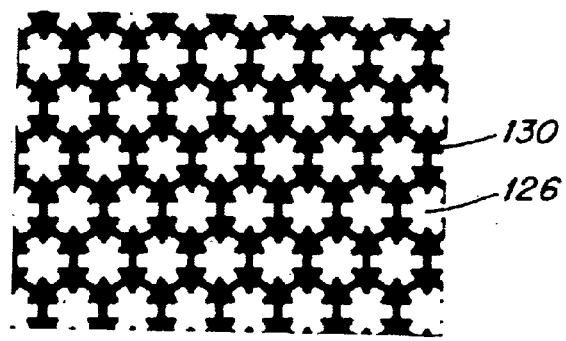
Figure 10C:
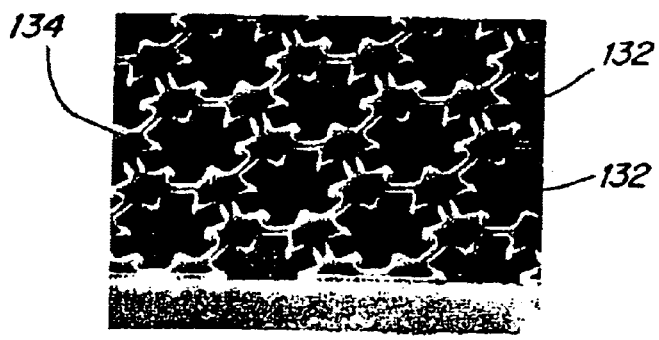

FIGS. 10a–c illustrate formation of a mask 122 on a thin layer 124 of chromium on a glass substrate 126 using the micromolding procedure as illustrated in FIG.1, followed by etching of chromium at regions 128 not covered by the mask. In FIG. 10a, the molding technique described above is used to form a pattern of polyurethane article 122 on chromium 124 leaving region 128 of chromium uncovered. The surface was exposed to an etchant (400 ml H$_2$O, 24 ml of 63% HNO$_3$, 62 g NH$_4$NO$_3$.Ce(NO$_3$)$_3$ for about 1 minute) that removes chromium but to which the polymeric article 122 is resistant. The result was a glass substrate 126 having thereon a patterned mask 130 defined by chromium protected from the etch by mask 122 in the pattern corresponding to mask 122 (and the pattern corresponding to the indentation pattern of the micromold). FIG. 10b is an optical micrograph of the chrome mask 130, top view. The chrome mask 130 was removed from the substrate 126 and placed on a photoresist article. FIG. 10c is a photocopy of an SEM image of a pattern that was generated in the photoresist film at regions 132 not protected by the mask. Raised portions 134, in a pattern corresponding to the pattern of the chromium mask, and corresponding to the original indentation pattern of the micromold from which the mask 122 was formed, were not ablated in the photolithography process.

According to another embodiment a substrate surface such as a silicon wafer can be spin-coated with photoresist. A micromold can be placed adjacent to a photoresist and channels defined thereby filled with a solvent that dissolves photoresist but not the micromold. A pattern of the silicon wafer not covered by photoresist, the pattern corresponding to the indentation pattern of the micromold, is thereby produced. Further processing familiar to those of ordinary skill in the art can be carried out.

Figure 11:
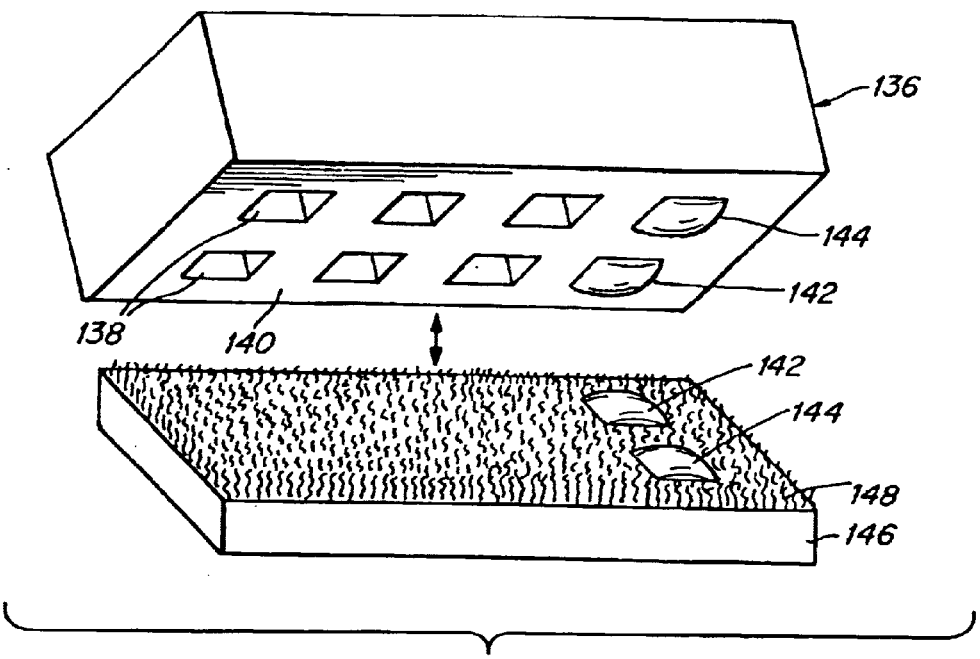

FIG. 11 illustrates schematically an applicator 136 that can be used for applying any of the above-described chemically or biochemically active agents, polymeric precursors, fluid precursors of solid structures, fluid carriers of particulate matter, and the like to a substrate surface. Applicator 36 includes a plurality of isolated indentations 138 separated from each other by intervening regions of a surface 140 in which the indentations are formed. As illustrated, two of the indentations contain fluid carrier 142 and fluid carrier 144, respectively. The fluid carriers 142 and 144 can be the same or different. A substrate 146 is shown that, for purposes of illustration, includes a self-assembled monolayer 148 formed thereon which can serve as an adhesion promoter. Fluid carriers 142 and 144 are transferred to isolated regions proximate the surface of substrate 146, in particular, regions of the exposed self-assembled monolayer 148 on the surface of substrate 146. The transfer typically takes place by bringing the surface 140 of the applicator into contact with the self-assembled monolayer 148 but, if the fluid carriers 142 and 144 protrude from the indentations, the surface 140 need only be placed in close proximity to the self-assembled monolayer 148.

Fluid carriers 142 and 144 can be any of the species described above and, according to a particularly useful embodiment, carry or define a chemically or biochemically active agent that can be used in a subsequent assay or the like. For example, a self-assembled monolayer 148 can be a monolayer of a species X—R—Ch as described in U.S. Pat. No. 5,620,850, issued Apr. 15, 1997 to Bamdad, et al., entitled "Molecular Recognition at Surfaces Derivatized with Self-Assembled Monolayers", incorporated herein by reference. These species have the general formula as above where X represents a functional group that adheres to a gold surface, R represents a spacer moiety that promotes formation of a self-assembled monolayer of a plurality of the molecules, and Ch represents a bidentate, tridentate, or quadradentate chelating agent that coordinates a metal ion. The chelating agent includes a chelating moiety and a non-chelating linker moiety, such that it can be covalently linked via its linker moiety to the spacer moiety while allowing the chelating moiety to coordinate a metal ion. According to a preferred aspect of the invention a metal ion is coordinated to the chelating agent, and a binding partner of a target molecule is coordinated to the metal ion. This arrangement is facilitated by selecting the chelating agent in conjunction with the metal ion such that the chelating agent coordinates the metal ion without completely filling the ion's coordination sites, allowing the binding partner to coordinate the metal ion via coordination sites not filled by the chelating agent. A non-limiting exemplary list of suitable chelating agents includes nitrilotriacetic acid, 2,2'-bis (salicylideneamino)-6,6'-demethyldiphenyl, and 1,8-bis(a-pyridyl)-3,6-dithiaoctane. The binding partner can be a biological species that includes a polyamino acid tag, such as a tag made up of at least two histidine residues, that coordinates the metal ion. In this context the term "adhere" means to chemisorb in the manner in which, for example, alkyl thiols chemisorb to gold.

In this case the fluid carriers 142 and 144 can be carriers of a nickel ion, resulting in a surface suitable for capture of a biological binding partner carrying a polyamino acid tag selectively at regions to which carriers 142 and 144 had been applied. According to this embodiment, immediately following application of carriers 142 and 144 to the substrate surface, it can be advantageous to expose the surface of substrate 146 to a chelating agent in solution to remove excess nickel ion from the surface. In this way, stray uncoordinated nickel ion does not coordinate to the self-assembled monolayer 148 at regions outside of those regions to which carrier 142 and 144 had been applied. The latter-applied chelating agent preferably less-strongly coordinates nickel ion than the chelating agent immobilized at the surface. Following this application step, a plurality of isolated regions of self-assembled monolayer 148 include nickel ion. Accordingly, when the surface is exposed to a polyamino acid-tagged biochemically active agent, the biochemically active agent will attach selectively at those regions to which nickel ion had been applied.

According to another embodiment, self-assembled monolayer 148 can be a species X—R—Ch—M as described in the above-referenced co-pending application Ser. No. 08/312,388, and the species 142 and 144 can be polyamino acid-tagged biological binding partners, optionally contained in a fluid carrier, that are attached to the surface selectively at those regions corresponding to the indentation pattern of the applicator, According to this embodiment the separate, isolated regions can include separate, distinct biochemically active agents. This can be accomplished, for example, by placing applicator 136 in register with a plurality of reservoirs of distinct (different) biochemically active agents to position distinct biochemically active agents in the respective indentations of the applicator, then placing the applicator adjacent the surface of substrate 146 to transfer distinct biochemically active agents to distinct, isolated regions of the surface. The procedure can be repeated using fresh substrate surfaces for each step, thus surfaces carrying distinct regions of distinct biochemically active agents can be mass produced. In addition to the species described above, cells can be immobilized at a substrate surface in this manner as well. Register between the applicator and the substrate surface can be controlled via mechanical, electronic, magnetic, and/or optical apparatus.

According to another embodiment, species 142 and 144 or species carried by fluid carriers 142 and 144 can be transferred to a surface carrying a self-assembled monolayer other than the monolayer of X—R—Ch—M as described above. For example, a self-assembled monolayer exposing a hydrophobic functionality such as an alkane functionality can be formed on a surface (e.g., hexadecanethiol on gold) and a biochemically or chemically active agent that adheres to a hydrophobic surface can then be applied to the surface in discrete regions or in a pattern as described above. Where the biochemically active agent is a cell or cells, it may be advantageous to coat the hydrophobic surface with a cytophilic species such as laminin. Reference can be made to U.S. patent application Ser. No. 08/131,838 of Sighvi, et al. referenced above, in connection with the immobilization of cells at surfaces.

Immobilization of cells and other biochemically active species can be carried out without a self-assembled monolayer as well. For example, a hydrophobic surface coated with laminin, and free of self-assembled monolayer, can serve as a substrate for immobilization of a pattern of cells in accordance with the invention.

According to this and other embodiments, the substrate surface can carry chelating agent immobilized via other than a self-assembled monolayer. For example, chelating agents coupled to dextran at a surface, as is known, can be employed. Although a self-assembled monolayer 148 is illustrated on the surface of substrate 146, a self-assembled monolayer is not needed according to all embodiments. For example, substrate 146 can be adhesive to a species transferred to it from applicator 136, for example a biochemically or chemically active agent and fluid carriers 142 or 144, or the like. Additionally, the applicator can be placed in contact with the substrate surface and allowed to remain in place while any species present in the fluid precursor is allowed to harden, the fluid carrier is allowed to dissipate, or the like.

In accordance with all embodiments of the invention, such as those illustrated in FIGS. 1, 2, and 11, the species formed proximate the substrate surface in a pattern corresponding to the indentation pattern of the article itself can be a self-assembled monolayer. Suitable self-assembled monolayer-forming species are described in U.S. Pat. No. 5,512,131 of Kumar, et al., referenced herein. Self assembled monolayers formed of species X—R—Ch, as described above, with or without metal ion and/or biological species coordinated thereto, can be used, as well as other self-assembled monolayer-forming species disclosed in application Ser. No. 08/312,388, by Bamdad, et al., referenced above.

Figure 12:
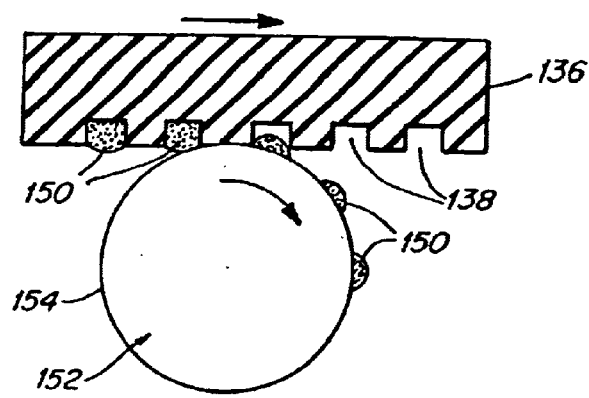

FIG. 12 illustrates schematically a process for applying a species from indentations in an applicator to a non-planar surface. An applicator 136 (shown in cross section) includes a plurality of indentations 138, each filled with a species 150. Each of the indentations can be filled with the same fluid or different fluids. Species 150 can be any of the above-described fluid precursors, chemically or biochemically active agents, or the like. An article 152 having a surface 154 is placed adjacent the application surface of applicator 136 and rolled against the applicator as described in commonly-owned, co-pending U.S. patent application Ser. No. 08/397,635 by Whitesides, et al., entitled "Microcontact Printing on Surfaces and Derivative Articles", and Internation Patent Application Publication No. WO 96/29629, both incorporated herein by reference. As the article 152 including nonplanar surface 154 is rolled against the applicator 136, species 150 is transferred to surface 154 in a pattern corresponding to the indentation pattern of the applicator. The indentation pattern can be any pattern as described above, for example individual, isolated regions or one or more continuous linear or non-linear indentations. The indentation or indentations can be of one or more depths. Application to nonplanar surfaces having various radii of curvature can be carried out according to the invention, for example, radii of curvature of less than about one centimeter, preferably less than about one millimeter, more preferably less than about 500 microns, more preferably less than about 100 microns, more preferably less than about 50 microns, and according to a particularly preferred embodiment printing can occur on substrates with radii of curvature on the order of about 25 microns or less.

Figure 13:
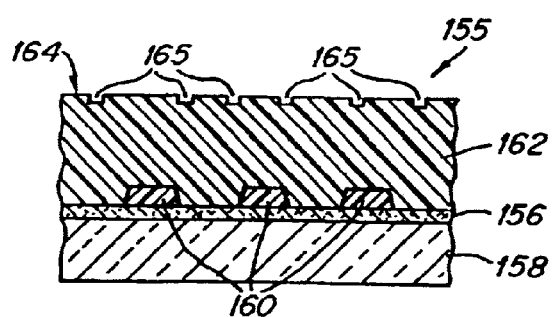

FIG. 13 illustrates an article 154 created by forming, on a silicon dioxide surface 156 of a silicon substrate 158, a patterned structure 160, for example a polymeric structure formed from a prepolymeric fluid using a micromold as illustrated in FIG. 1. Subsequently, a second fluid precursor is positioned so as to cover the patterned structure 160 and allowed to solidify. According to the embodiment illustrated, a fluid precursor was placed atop the patterned structure 160 and a micromold having a complex pattern was placed atop the fluid precursor. The fluid precursor was hardened to form a structure 162 covering and encompassing the patterned structure 160 on the substrate surface. The second structure 162 included an exposed surface 164 having a pattern of indentations 165 complementary to the indentation pattern of the second micromold. The overall structure, when structure 160 differs in refractive index from structure 162, can serve as a waveguide, the second structure 162 serving as a cladding. The contoured surface 164 of cladding 162 is lossy. The pattern of surface 164, in most instances, is not important to the waveguide function. Waveguides were fabricated from several classes of polymeric materials (epoxies, polyurethanes, and polyacrylates on $Si/SiO_2$ substrates. Waveguides clad with polymers having slightly lower refractive indices gave single-mode output in the visible and near infrared regions. A typical waveguide structure exhibiting single-mode behavior consisted of a trapezoidal waveguide ($n_{guide}$=1.545) clad in a polymeric slab with $n_{cladding}$1.52. The waveguide was 0.7 centimeters long and the wavelength of light was 0.85 micron. Photocurable polymers are preferred. Waveguides are described in greater detail below.

Referring now to FIGS. 14a–k, a schematic illustration of a surface derivatized so as to include discrete regions of differing chemical functionality is shown. The article schematically illustrated finds particular use as a combinatorial library. An article by Jacobs, et al., entitled "Combinatorial Chemistry-Applications of Light-Directed Chemical Synthesis", Trends in *Biotechnology*, volume 12, 19–26 (January, 1994; incorporated by reference above) describes a photolithographic process for forming a combinatorial library. Jacobs, et al. describe derivatizing a substrate with linker molecules that contain amines blocked by a photochemically cleavable protecting group. Specific sites on this synthesis surface are photo-deprotected by illumination through a photolithographic mask. Those regions exposed to light are deprotected, and may then be coupled to amino acids of interest using standard peptide-synthesis conditions. The process is repeated using new masks until an array of compounds of the desired length and composition are built up. The patterns of photolysis and order of addition of amino acids define the products and their locations on the solid support. The present invention can find application in combinatorial library synthesis with a minimum of expense and equipment. Those of ordinary skill in the art will recognize that any of a wide variety of chemically and biologically active agents can be used in accordance with the procedure discussed below and illustrated in FIGS. 14a–k. The criteria for selection of such agents is similar to selection criteria for those agents described above that can be positioned on a substrate surface using a forming article or micromold 20. In a manner analogous to the procedure of Jacobs, et al., wet chemical protecting groups can be utilized in accordance with the present invention rather than photochemically cleavable protecting groups. Orthogonal-stripe methods and binary synthesis of combinatorial libraries in accordance with the invention, with reference to FIGS. 14a–k, are described below in the prophetic example.

The following prophetic example involves the creation of a combinatorial library on a substrate surface using the micromold of the invention. With optional reference to Jacobs, et al., "Combinatorial Chemistry—Applications of Light-Directed Chemical Synthesis", *Trends in Biotechnology*, 12, 19–26 (January, 1994) and *Chemical & Engineering News*, 74, 7, 28–73 (Feb. 12, 1996), those of ordinary skill in the art can follow the teachings herein to form a combinatorial library inexpensively.

Figure 14A:
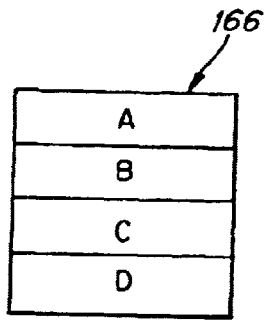
FIGS. 14a–14k illustrate schematically the creation of a combinatorial library in accordance with the invention.
Figure 14B:
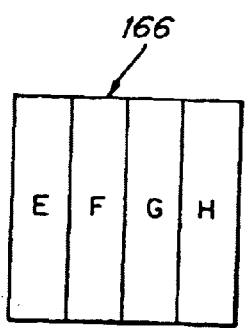
Figure 14C:
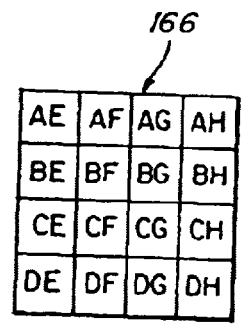

Reference will be made to FIGS. 14a–k, which illustrate schematically top views of a substrate surface. FIGS. 14a–c illustrate an "orthogonal-stripe" method. According to the technique, a plurality of micromolds are fabricated, each of which has a distinct channel pattern. Each micromold is fabricated so as to cover substrate surface 166, or at least enough of substrate surface 166 to define a channel or channels necessary for application of chemically or biochemically active agents to desired regions of the surface. For purposes of illustration, the description will assume use of a micromold that completely covers substrate surface 166, and includes indentations in register with certain portions of substrate surface 166. One micromold includes an indentation in register with a portion of the substrate surface designated "A" in FIG. 14a and includes a contact surface that contacts the remaining substrate surface at areas designated "B", "C", and "D". With reference to FIG. 14b, individual micromolds will be fabricated that include contact surfaces that cover all portions of the substrate except one of the portions "E", "F", "G", or "H". That is, each micromold forms a channel through which a chemically or biochemically active agent (reactant) can be delivered to the substrate surface at a portion in register with the channel, while remaining portions of the micromold block regions proximate the substrate surface from interaction with the particular chemically or biochemically active agent. Any combination of micromolds can be used to apply to the surface, in any combination, various chemically or biochemically active agents. For example, with reference to FIG. 14a, if a micromold having a channel in register with region "A" of the substrate surface is used to apply to the surface a chemically active agent "A" and then, with reference to FIG. 14b, a micromold is placed adjacent the substrate surface that has an indentation in register with region "E" and is used to apply to region "E" a chemically active agent "E", the substrate surface will include a region carrying chemically active agent "A" (the region designated "A" in FIG. 14a), a region carrying chemically active agent "E" (the region designated "E" in FIG. 14b), and at the region where the regions "A" and "E" intersect both chemically active agents will have been applied (upper left corner of the substrate surface as viewed in FIG. 14c). It can be seen that, if all combinations of micromolds and chemically active agents are employed, the result will be a grid on the substrate of each combinatorial permutation of the chemically active agents each confined to a separate region of the substrate surface (FIG. 14c). As is apparent to those of ordinary skill in the art, the order of application of active agent to the various regions of the substrate surface can be used to tailor the synthesis of the individual species at the various locations on the substrate surface.

Figure 14D:
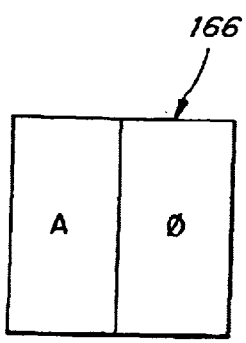
Figure 14E:
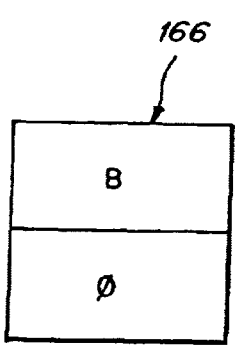
Figure 14F:
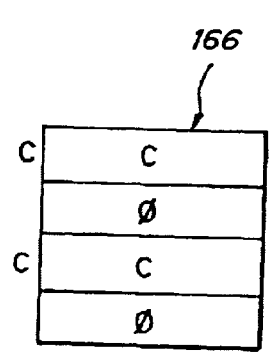
Figure 14G:
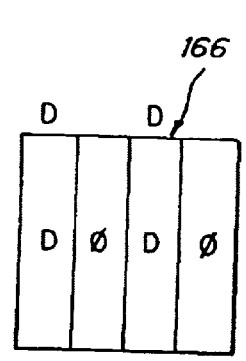

With reference to FIGS. 14d–k, a "binary" synthesis technique is described. In FIG. 14d, a first micromold having an indentation in register with region "A" and a contact surface in register with region "Ø" is used to apply to the substrate surface an active agent "A" selectively at region "A". FIG. 14b shows surface 166 including a region "B" in register with an indentation of a second micromold and a region "Ø" in register with a contact surface of the second micromold, via which an active agent "B" can be applied selectively to region "B" of the substrate surface. FIG. 14f shows surface 166 having portions "C" and "Ø" that are positionable in register with indentations and contact portions, respectively, of a third micromold to apply an active agent "C" to regions "C". In FIG. 14g the surface includes portions "D" and "Ø" that are positionable in register with indentations and contact portions, respectively, of a fourth micromold to transfer agent "D" selectively to regions "D". The binary technique is less labor intensive than the orthogonal-stripe method in that only four transfer or flow steps involving four micromolds are needed to create a grid of sixteen distinct chemically or biochemically functional regions on the substrate surface.

Figure 14H:
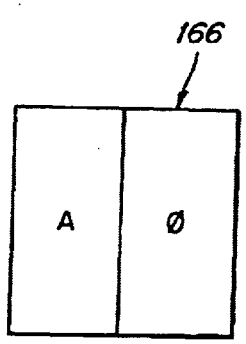
Figure 14I:
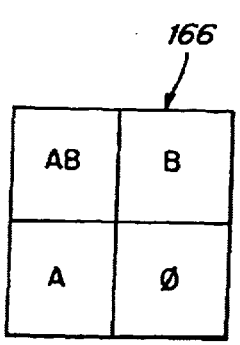
Figure 14J:
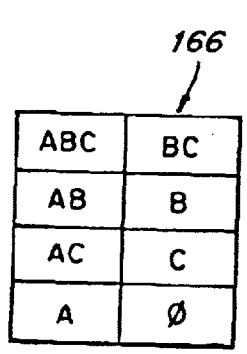
Figure 14K:
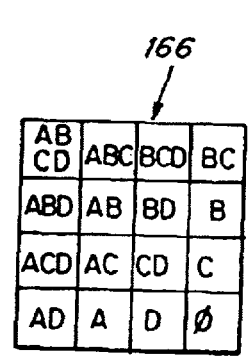

After application of the first micromold and formation of chemically or biochemically active agent "A" via the channel of the first micromold, agent "A" is applied to the left side of the substrate surface 166 and the right side of the substrate surface remains free of agent as illustrated in FIG. 14h. After application of agent "B" to the upper portion of substrate surface using the second micromold, four quadrants of the substrate surface carry agent "A" plus agent "B", agent "B", agent "A", and no agent, respectively, as illustrated in FIG. 14i. After application of agent "C" via the channels of the third micromold, eight regions of distinct chemical or biochemical functionality exist on the surface as illustrated in FIG. 14j. After application of agent "D" via the indentations of the fourth micromold, sixteen distinct chemically or biochemically active regions are formed as illustrated in FIG. 14k, namely "ABCD", "ABC", "BCD", "BC", "AND", "AB", "BD", "B", "ACD", "AC", "CD", "4C", "AD", "A", "D", and "Ø". The register between each micromold and the substrate surface can be controlled by pins in the substrate that engage each micromold, pins in each micromold that engage the substrate surface, an X-Y table that positions the substrate surface identically relative to each micromold, optical, magnetic, or electronic aligning apparatus, or other equivalent apparatus that can align each micromold with the substrate surface. Accurate register at the micron scale is achieved.

Those of ordinary skill in the art have the ability to select, without experimentation or with only routine experimentation, chemically or biochemically active agents that can be used to create a myriad of chemically active or biochemically active combinatorial libraries according to the technique of the invention. It can be useful to first coat substrate surface 166 with a common chemical linker functionality coupled to a chemical protecting group, apply a first micromold to the substrate surface, first deprotect at the region in register with the channel, then carry out a synthesis step at that region and reprotect, then remove the first micromold and apply a second, different micromold, again deprotect at the portion of the substrate surface in register with the channel of the second micromold, carry out a second synthesis step, and reprotect, etc. Libraries of peptides, synthetic molecules such as new drugs, naturally-occurring chemical and biochemical species, oligonucleotides and the like can be created. Indeed, any of the chemically or biochemically active agents, fluid precursors, prepolymeric fluids, or the like as described above that are transferable from a microapplicator or that can be applied, for example via capillary action, to a surface using a micromold as described above, can find use in the combinatorial arrangement described. Any combination of various agents can be used.

As an alternative embodiment to that described above, an article 20 as illustrated in FIG. 2, having a contoured surface 22 including a plurality of protrusions separated by intervening indentations 24 can be used as a stamp for forming a combinatorial library. Stamping as described in U.S. Pat. No. 5,512,131 (issued Apr. 30, 1996 to Kumar, et al., referenced above) can be employed. The stamp includes a stamping surface defined by the outer surfaces of the protrusions. The process is described with reference to FIGS. 14d–k. A surface 166 carries a protecting group, for example, a self-assembled monolayer exposing outwardly an azide functionality. A stamp having a surface including a protrusion in register with area A of surface 166 (FIG. 14d) is prepared by applying to the protrusion a deprotecting species such as a reducing agent for reduction of the azide to a deprotected, reactive amine. Application of the stamp to surface 166 deprotects the self-assembled monolayer at region A, but leaves the remainder of surface 166 (Ø) protected. Then, chemical reactivity at region A can take place, followed by reprotection of the entire surface. Then the stamp can be re-oriented, or a second stamp chosen, so that region B is deprotected by contact with a stamping surface (protrusion) of a stamp. Chemical reaction then is carried out a region B, and the surface re-protected. With reference to FIG. 14f, a stamp having protrusions corresponding to regions C is used to deprotect at regions C, followed by chemical reaction at regions C and re-protection, and the process carried out similarly at regions D (FIG. 14g). According to a preferred embodiment, the stamping surface itself, without any auxiliary agent carried thereon, can deprotect at regions of surface 166 in register with the stamping surface. For example, a stamp having an acidic stamping surface such as a hydrogel loaded with a component of low pH can be used. For example, Dextran™ carrying polyphosphoric acid can be grafted to a surface of a rigid or elastomeric stamp and used to deprotect surface 166 at regions corresponding to the protrusions or stamping surface. Other protecting/deprotecting chemistries such as hydrolysis chemistry can be carried out.

According to another embodiment, rather than building a combinatorial library through step-by-step synthesis of various species at various distinct regions proximate a substrate surface, distinct species can be synthesized and applied to the substrate surface after synthesis. A combination of these approaches can be used as well, involving synthesis of building blocks that are assembled according to the prophetic example.

FIG. 15 illustrates a set of particularly preferred fabrication techniques of the invention in which, rather than applying article 20 to substrate surface 28 followed by introduction of fluid precursor 36 into channels 32 so defined, article 20 is used as an applicator to transfer the fluid precursor to substrate surface 28. The following description will be made with reference to fabrication of a structure 38 and other structures that are waveguides, from a precursor 36 that will be referred to as a waveguide precursor, although the following description defines one aspect of the invention that is applicable to creation of any of a wide variety of structures described herein and is not limited to waveguides. In FIG. 15, fluid precursor 36 is first applied to indentations 24 of applicator 20. Excess fluid precursor then can be removed, by scraping, from application surface 22. For example, a block of material similar or identical in composition to that of article 20 can be used to scrape off excess prepolymer. Alternatively, with appropriate structures, the excess precursor can be blown off with a brisk stream of gas such as nitrogen. A brisk stream of gas also can be used to remove remaining drops of precursor after the bulk excess of precursor has been scraped away. Applicator surface 22, the indentations of which are filled with fluid waveguide precursor 36, then is placed in contact with surface 28 of substrate 30. Applicator 20 then can be removed, leaving some or all of precursor 36 in contact with surface 28 where it is subsequently made dimensionally stable or, according to preferred embodiments, fluid precursor 36 is hardened to the point that it is dimensionally stable while article 20 remains in place upon substrate surface 28. Where fluid precursor 36 is a fluid prepolymer, and is heat-curable, the precursor can be heated, for example, by heating substrate 30, article 20, both substrate 30 and article 20, or applying radiative heat. Where precursor 36 is a photopolymerizable fluid, it can be exposed to electromagnetic radiation that causes polymerization. A fluid precursor 36 can be partially or fully polymerized prior to removal of article 20, so long as it is polymerized to the extent that it is dimensionally stable and self-supporting. In preferred embodiments, as described below, it is often advantageous to only partially polymerize a fluid prepolymeric precursor 36.

Where fluid precursor 36 is a fluid carrier of a suspension, the fluid carrier can be selected in conjunction with the material of article 20 to allow the fluid to be absorbed into article 20 and thereby dissipated, resulting in deposition of solid material from the suspension as the patterned material on substrate surface 28. Where fluid precursor 36 is a solution of a dissolved precipitating species, conditions such as temperature, pH, or the like can be altered to cause precipitation. One advantage of the technique of FIG. 15 is that the fluid precursor is in contact with article 20 for only a very brief period of time, thus if article 20 adsorbs or absorbs any components of fluid precursor 36 disadvantageously, such as adsorption of dyes, this is minimized. Another advantage is that with a thermally-curable precursor the technique is made much easier since the time required for the process is very fast relative to typically curing times.

Following solidification of fluid precursor 36 to form an array of waveguides 38, solidification taking place to the extent that waveguide 38 is dimensionally stable, article 20 is removed from substrate 30. Following this step, or other steps for forming an array of waveguides 38 on substrate surface 28 (e.g. as described with reference to FIG. 1), a cladding can be provided upon the waveguide array to form a waveguide assembly 44 by adding a hardenable cladding precursor fluid 40 on top of the array, optionally forming fluid 40 into a desired shape with a desired thickness above and beside the waveguide array by, for example, positioning a cladding mold 42 above the precursor to form the precursor, allowing the cladding precursor to harden (for example, via polymerization) and removing cladding mold 42 to form a cladding 43 that includes a layer of cladding above waveguides 38. In another embodiment a cladding mold 168 can be used which molds cladding precursor 40 between waveguides 38 and laterally of waveguides 38, but does not allow formation of cladding above the waveguides to form an assembly 172. This can be accomplished where the cladding mold 168 is a flexible elastomeric mold that conforms to form a mold resting atop waveguide 38. The cladding precursor is allowed to harden, and removal of the mold results in a cladding 170 that fills spaces between waveguide 38, and extends laterally beyond the lateral-most waveguides such that each side of each waveguide is contacted by cladding, but the top of each waveguide is exposed. In another embodiment a waveguide assembly 174 can be formed by applying cladding precursor 40 to waveguides 38, allowing the cladding precursor to drip off of the waveguides, and hardening the cladding precursor.

In each case, subsequently, the substrate/waveguide/cladding assembly can be cleaved along lines a—a and b—b to define a waveguide assembly 44, 172 or 174 having a typical waveguide width x on the order of less than about 100 microns, typically on the order of from about 1 to about 10 microns, more typically from about 2 to about 4 microns, a waveguide height y on the order similar to that of dimension x, more typically slightly less than x, for example about 1 micron, and, in the case of waveguide assembly 44, an overall assembly height including cladding of a dimension z on the order of dimension y to about 10 times dimension y, for example from about 1 to about 10 microns and a length 1 of any of a wide variety of lengths on the order of 100 microns to centimeters. Larger waveguides can be made as well, for example waveguides having width or height on the order of 200 or 250 microns, with spacing of similar order. In the case of waveguide assembly 172 the cladding height equals the waveguide height, and in the case of 174 the cladding height typically is very slightly greater than the waveguide height.

Another technique for fabricating a waveguide assembly 172, including waveguides 38 and cladding 170 which contacts the sides, but not the tops of waveguides 38 is as follows. Following fabrication of waveguides 38, and prior to application of any cladding, a microcontact printing technique as described in international patent publication no. WO 97/07429, of international patent application no. PCT/US96/13223 entitled "Patterned Materials Deposition Effected with Microcontact Printing" is carried out to apply a hydrophobic component selectively to the tops, but not the sides of waveguides 38, followed by addition of a hydrophilic cladding prepolymeric precursor which assembles within and between waveguides 38, but not atop waveguides 38, followed by curing of the cladding precursor. The particular microcontact printing technique involves coating a flat applicator with a self-assembled monolayer forming molecular species and applying the flat applicator to waveguides 38 such that the applicator contacts only the tops of waveguides 38. Any molecular species transferable in this manner can be used to create a hydrophobic functionality atop waveguides 38 such that a hydrophilic prepolymer will assemble between waveguides 38 and laterally on either side, or the opposite can be carried out in which a hydrophilic material is applied to the tops of waveguides 38 and a hydrophobic cladding precursor used to fill spaces between and laterally of the waveguides where the waveguides and surface 28 of substrate 30 is sufficiently hydrophobic. In one technique, surface 28 and waveguides 38 were subjected to oxidizing treatment, and microcontact printing was used to transfer a self-assembled monolayer of a fluorine-terminating molecule to the surface. Specifically, tridecafluoro-1,1,2,2-tetrahydro(o-octyl)-1-trichlorosilane was applied to the tops, but not sides, of waveguides 38 and formed a hydrophobic self-assembled monolayer thereon. A hydrophilic cladding precursor, in particular a liquid polyurethane prepolymer, was added and assembled between and laterally of waveguides 38. Curing of the polyurethane cladding precursor, followed by cleaving of the waveguide ends, resulted in a waveguide assembly similar to assembly 172.

In typical embodiments, cladding is added to waveguides 38 to lower the refractive index difference between waveguides 38 and their surrounding environments. Without cladding, waveguides 38 typically are very good performers, but support too many modes. Addition of cladding, which reduces the refractive index difference at the boundaries of waveguides 38, reduces higher order modes.

FIG. 13 (discussed above) is essentially identical to a cross-section through line a—a of waveguide assembly 44 of FIG. 15, showing a typical substrate 30, optional film 31 of an adhesion promoter, native oxide layer, or the like on substrate 30 (the top surface of film 31 defining substrate surface 28 according to this embodiment), array of waveguides 38, and cladding 43. The waveguide of FIG. 13 differs from waveguides fabricated in accordance with the technique of FIG. 15 in that it includes a contoured cladding surface corresponding to a contoured cladding mold. Precursor 36 is a material as described above which can serve as a waveguide. Selection of such materials is within the level of ordinary skill in the art.

In embodiments of the invention involving waveguide fabrication, substrate 30 can be essentially any material including those materials described above, but should be optically smooth. Substrate surface 28 can be of the same material as the bulk material of substrate 30, or a different material. A non-limiting, exemplary list of substrate materials includes silver, gold, glass, silicon/silicon dioxide, and the like. The waveguide pattern can be formed on contoured surfaces, and flexible surfaces. Where substrate 30 is flexible (for example, a polyvinylchloride film) the waveguide can be deformed while guiding light. The utility of this technique will be described more fully below. In embodiments of the invention involving waveguide fabrication, article 20 can be as described above, and preferably is elastomeric.

Selection of materials for waveguide 38, cladding 43, and substrate 30 (and optional film 31) can be selected by those of ordinary skill in the art to form a structure that can guide electromagnetic radiation of a desired frequency. As is known, total internal reflection of electromagnetic radiation will occur within waveguide 38 where the electromagnetic radiation propagating within the waveguide strikes an interior boundary of the waveguide to form an angle θ, with a line normal to the interior boundary, where sin θ is≧ (refractive index of the cladding)/(refractive index of the waveguide). Those of ordinary skill in the art can select materials to form the overall system 44 that will serve as a waveguide. In one set of embodiments cladding 43 can be non-existent. That is, the cladding can be the environment surrounding the waveguide, such as air. In some embodiments it is useful to have a cladding defined by a material filling the indentations between and defined by waveguides 38, where the top surfaces of waveguides 38 are exposed to ambient conditions. The difference in index of refraction between waveguide and cladding, and waveguide and the substrate, typically is from about 0.01 to about 0.001. These and other embodiments can be useful as sensors, etc., and are described more fully below.

It is one feature of the invention that waveguides 38 and cladding 43 can be formed from an identical, or nearly identical fluid prepolymer, the degree of polymerization of which can be controlled by the amount of exposure to polymerization conditions such as heat or radiation. For purposes of the invention, "polymerization" is meant to encompass cross-linking. This technique is facilitated by the fact that the refractive index of a solid typically is greater than the refractive index of a liquid of similar composition in that the density of a solid typically is greater than of a liquid. The difference in index of refraction typically decreases with curing time for a polymer. Thus, the difference in refractive index can readily be tailored. This technique provides several advantages that will become apparent from the discussion below. One advantage is simplicity, since in this embodiment only a single prepolymer fluid need be used, first as prepolymer fluid 36 (with reference to FIG. 15) that is positioned with article 20 against substrate surface 28 and polymerized, for example photopolymerized, followed by addition of a common prepolymer (the same prepolymer) cladding precursor 40 which then can be photopolymerized. During polymerization (curing) of cladding prepolymer 40, waveguide 38 is cured to a greater extent, and the refractive index difference between cladding 40 and waveguide 38 decreases during curing of cladding 40. One advantage of using identical, or nearly identical fluid prepolymers both for waveguides 38 and cladding 43, the difference in refractive index being due to different curing times, is that any batch-to-batch difference between polymers is unimportant as the amount of exposure to polymerization conditions is the only important feature. That is, the relative refractive index change in material, during curing, is what is important, and conditions do not need to be adjusted because of slight variation in material composition.

One advantage of the transfer technique of FIG. 15 is that it is exceptionally simple experimentally, and very inexpensive. It can readily be used to produce multiple copies of complex microstructures. Another advantage of the technique is that many waveguides can be fabricated essentially simultaneously. Tens or hundreds of applicators 20 can be fabricated from a single master which is, in turn, fabricated from a photolithographically-created surface or the like, and each applicator can be used to fabricate hundreds or thousands of waveguides. For example, where an applicator 20 having a dimension perpendicular to the linear dimension of indentations 24 of approximately 3 centimeters is used, and indentations 24 each are of approximately 2 microns in width and spaced approximately 2 microns from each other, one molding process as illustrated in FIG. 15 can result in more than 4,000 waveguides.

Figure 16:
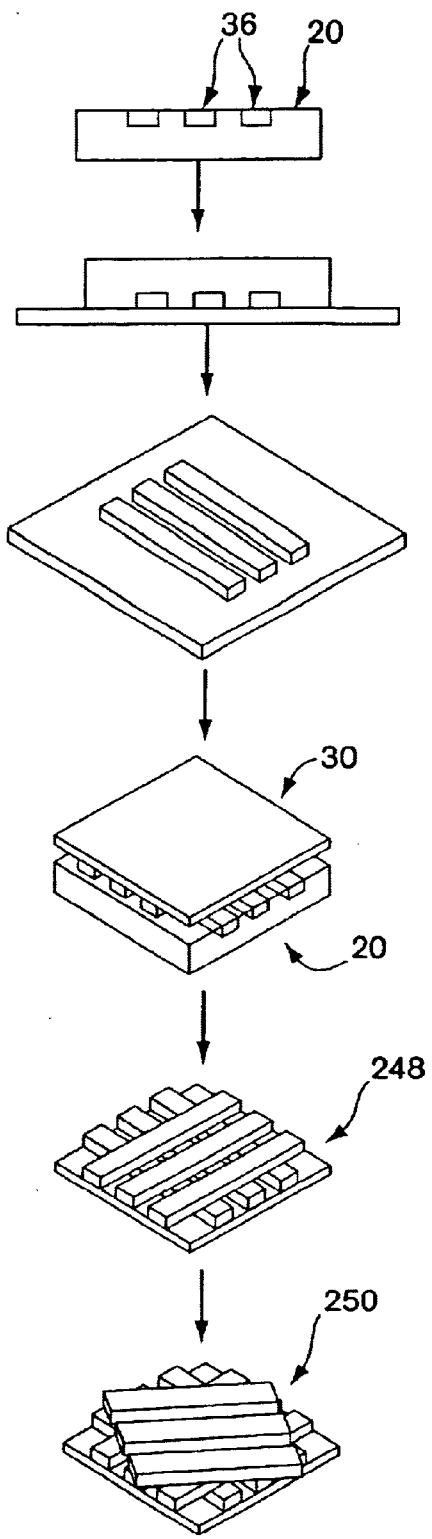
FIG. 16 illustrates a technique for forming a multi-layer waveguide structure.

Another advantage of the transfer molding technique of FIG. 15 is that multiple layers of waveguides can be fabricated readily. With reference to FIG. 16, applicator 20 first can be used to transfer fluid waveguide precursor 36 to substrate surface 28 where it is hardened to form waveguide array 38, as illustrated also in FIG. 15, and then waveguide array 38 on substrate 30 can be placed upside down upon another applicator 20 including indentations filled with fluid waveguide precursor 36, precursor 36 can be cured, and applicator 20 removed to form a two-layer stacked array 248. The process can be repeated any number of times to form any number of layers of waveguide arrays, as exemplified by stacked waveguide array 250, with the waveguides arranged in any orientation relative to each other in which support for each layer is provided.

Yet another advantage is that periodicity in the cladding structure 43 (FIG. 15) can be readily formed, via a cladding mold 42 including a periodically contoured inner surface, or via irradiation of cladding 43 through a mask to cure alternating portions of the cladding to a greater extent relative to intervening portions. In this manner, a grating can be fabricated in the cladding, such as a Bragg grating. Gratings also can be fabricated directly in or onto waveguides 38 by using a mold 20 in which the indentations that in part define the mold for the waveguides includes a contoured interior surface. Chirped waveguides and other periodic structures can be fabricated in the cladding, or in the waveguide core itself, in this technique. Attenuation can be achieved in this way, and resident cavities can be created.

Another feature of the present invention is the ability to fabricate waveguide couplers, easily and conveniently, regardless of the local geometry of the waveguide. FIG. 17 is a schematic illustration of a prior at "Y" coupler including branched portions as shown, for example, in U.S. Pat. No. 5,313,545 (Kuo, et al.), including a coupling region 252 and branching input/output regions 253, 254, 255, and 256. Radiation input from regions 253 and 255 will couple at region 252 and will branch and travel along both branching portions 254 and 256. Alteratively, radiation input from branches 254 and 256 can be made to couple at region 252 and branch into regions 253 and 255, optionally constructively or destructively interfering to some extent in region 252.

FIG. 18 is an illustration of a prior art "evanescent" coupler, the principle of which is used to provide coupling between guides of U.S. Pat. No. 5,481,633 (Mayer). This coupler operates on the principle that, depending upon the refractive index between waveguide and surrounding environment (e.g., cladding) the waveguide dimensions (size and shape), the wavelength of light, and separation between waveguides, an "evanescent tail" extends from each waveguide, the energy of the tail decreasing with distance from the guide. Where waveguides are close enough to each other, and the evanescent tail passes into the adjacent waveguide, radiation can leak into the adjacent waveguide and the waveguides couple. In the prior art array of FIG. 18, waveguide 258 includes a coupling portion 260 and non-coupling portions 262 and 264 and waveguide 266 includes a coupling portion 268 and non-coupling portions 270 and 272. In the array illustrated, based upon the selection of materials and dimensions and wavelength of light, coupling portions 260 and 268 are close enough such that the evanescent tail of radiation in each guide passes into the adjacent guide and coupling occurs in these regions. However, non-coupling portions 262, 264, 260, and 272 each are separated from the adjacent waveguide by a distance that does not allow coupling. Coupling thus controllably occurs only at regions 260 and 268, which thereby defines a coupling junction. The prior art arrays of FIGS. 17 and 18 are suitable for many purposes, but, as can be seen, requires significant control and geometry of construction.

The particular shape of the waveguide required for either of the couplers of FIGS. 17 and 18 is limited also by the fact that curves or corners that form part of the shape of a waveguide should not exceed a maximum amount of sharpness, or the critical angle of total internal reflection will be exceeded and loss of electromagnetic radiation will occur.

Figure 19:
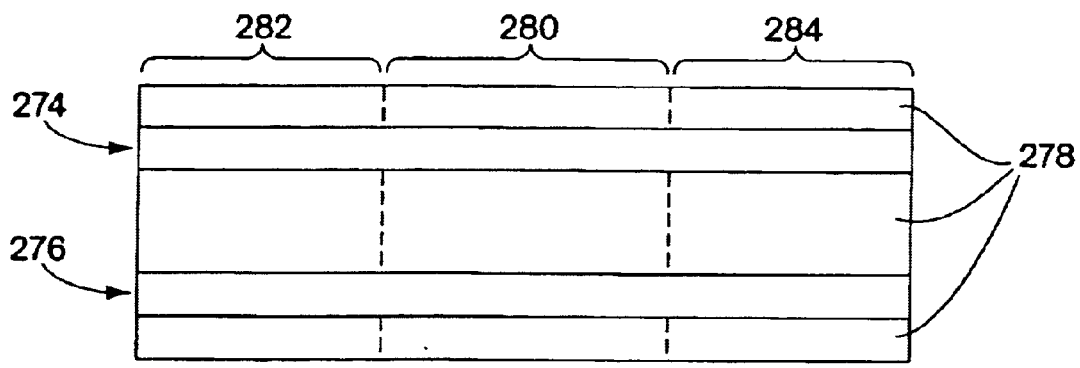
FIG. 19 is a schematic illustration of a coupling region, switch, or sensor using a waveguide array of the present invention.

The invention provides a solution to this problem, as illustrated in FIG. 19 which illustrates an array including essentially parallel waveguides 274 and 276 and cladding 278 which can completely envelope and cover waveguides 274 and 276, or the like. Each of waveguides 274 and 276 and cladding 278 can be formed from an identical prepolymeric precursor with differences in refractive index controlled by different curing times. The array of waveguides 274 and 276 and cladding 278 includes central portion 280 and lateral portions 282 and 284. Curing times are controlled such that the refractive index ratio between waveguides 274 and 276, and cladding 278, within central portion 280 is relatively small, while the refractive index ratio between the waveguides and the cladding in lateral portions 282 and 284 is relatively high, such that coupling occurs between waveguides 274 and 276 within portion 280, but does not occur in lateral portions 282 and 284. Thus, region 280 defines a coupled region of the waveguides that is functionally similar to the coupled portions 260 and 268 of waveguides 258 and 266 of FIG. 18, and coupled portion 252 of the branched structure of FIG. 17. This can be achieved, for example, as follows. Waveguides 274 and 276 are fabricated from fluid polymeric precursors as illustrated in FIG. 15, and only partially cured to the extent that they are dimensionally stable. Then, the same polymeric precursor, as a cladding precursor, is placed over waveguides 274 and 276 and cured until dimensionally stable. Where the refractive index difference at this point in the process is great, coupling cannot occur through all of portions 282, 280, and 284 of the array. Subsequently, only portion 280 is subjected to additional photopolymerization conditions, resulting in significantly decreased refractive index differences between waveguides 274 and 276 and cladding 278 in that region (280). The result is that, in regions 282 and 284, coupling does not occur, but in region 280 coupling occurs. One advantage of the technique is that coupling can be tailored at any region of the waveguide array where waveguides designed to carry UV or visible light, of the type produced by a red He—Ne laser, are separated more than about 2 microns, for example up to 6 microns, 8 microns, or even 10 microns in region 280, allowing much simpler fabrication that does not require as much precision. In contrast, the coupling regions of FIG. 18 are defined by their separation distance, which typically must be much smaller than the separation distance allowable for the system of FIG. 19, requiring significantly greater precision and related expense.

In another embodiment of the invention the locations of the regions of coupling between waveguides are tailorable, and the amount of coupling at those locations is controllable. This can be accomplished when waveguides 274 and 276 and cladding 278 are selected such that the refractive index ratio between waveguide and cladding can be changed, reversibly, after fabrication. For example, where the refractive index of cladding 278 can be changed reversibly based upon exposure to specific electromagnetic radiation (where, for example, cladding 278 is reversibly photosensitive; such materials are known to those of ordinary skill in the art) the array can be fabricated and region 280 irradiated with the specific radiation to cause coupling where no coupling occurs in regions 282 and 284. Then, the specific radiation can be discontinued, terminating coupling in region 280, and region 282 can be exposed to the specific radiation resulting in coupling within region 282 where no coupling occurs in regions 280 and 284. As can be seen a coupling pattern in a large array can be readily changed, reversibly, depending upon the pattern of the specific radiation. In another arrangement, cladding 278 can be one or more fluids contained in separate chambers that define regions 280, 282, and 284, and the content of the fluid chambers can be controlled to control the refractive index ratio between waveguide and cladding.

The above technique facilitates a waveguide coupler that can be used at different wavelengths of light. That is, where the refractive index difference at the boundaries of waveguides can be adjusted during use, or between uses, by exposure to different electromagnetic radiation, electric fields, or the like, the waveguide can be adjusted for use with different wavelengths of light. This also can be used to adjust the degree of coupling that occurs during use. For example, coupling could be adjusted from ten percent to fifty percent by exposure to electromagnetic radiation according to this technique.

The geometrical tailorability of refraction index ratio between cladding and waveguide facilitates the creation of a variety of switches and sensors. With reference to FIG. 19, where cladding 278 is an electro-optical material or other material that can reversibly change refractive index upon exposure to certain electric fields, or is a non-linear optical material (e.g., dye) that changes in refractive index in response to electromagnetic radiation, the array can be a sensor of that electric field or electromagnetic radiation since exposure to the field or radiation will cause a detectable change in coupling between waveguide 274 and waveguide 276. In one arrangement, region 280 can be defined by a cladding that is reversibly electric field sensitive, while sections 282 and 284 are not, thus sensitivity to the specific electric field exists at region 280 only, and coupling at region 280 is indicative of the existence and strength of the field.

As an example of a sensor of a chemical or biological species in accordance with the invention, the cladding of region 280 can include, on its exposed surface, a material that is sensitive to a particular analyte such that when the analyte is present, the refractive index of the cladding changes in an amount sufficient to detectably change the coupling characteristic between waveguides 274 and 276 in region 280. As one example, region 280 can define a flow chamber about waveguides 274 and 276 such that a desired fluid can be reversibly placed in contact with waveguides 274 and 276 in region 280. The change in the existence of, or concentration of, a particular analyte in the fluid (such as a salt or other refractive index-altering substance) can cause quantitative, or qualitative changes in coupling between guides 274 and 276 at region 280, resulting in quantitative or qualitative sensing. For example, a cation or anion exchange material can be provided that a surface, such as a sulfonic, phenolic, phosphoric, or carboxylic acid group, for capture of ions from solution. Chelating agents, kryptands, crown ethers, and the like can be used.

As another example, the array of FIG. 19 can be constructed where, at region 280 (or other or all regions) cladding 278 includes an exposed surface that carries an immobilized biological binding partner of a biological molecule or exposed surfaces of waveguides 274 or 276 carry an immobilized biological binding partner. Referring to FIG. 15, where a technique for forming a very thin cladding on the waveguides is used, the biological molecule can be provided on the cladding. A more sensitive sensor can result from a waveguide fabricated, with reference to FIG. 15, including exposed top surfaces. In a method for sensing the biological molecule, a medium suspected of containing the biological molecule is exposed to the surface of cladding 278, waveguide 274 and/or 276 (at region 280) if region 280 carries the biological binding partner exclusively and, if present, the biological molecule binds to its immobilized binding partner, changing the refractive index of cladding 278 (e.g. at region 280) and thereby changing the refractive index ratio between the waveguides and cladding in that region, detectably altering coupling. As mentioned, where a cladding completely covers waveguides 274 and 276 in this particular embodiment, it is generally desirable that cladding 278 form only a very thin layer above waveguides 274 and 276, such that biological binding at the outermost surface of the cladding produces a greater relative effect in change of refractive index ratio between waveguide and cladding.

Alternatively, the cladding may be non-existent and the biological molecule can be immobilized directly upon a surface of the waveguide, or the cladding can partially cover the waveguide surface with remaining portions of the waveguide surface carrying the immobilized binding partner. In specific embodiment, any of a variety of biological binding pairs can be used, one member of the pair immobilized at cladding 278 or waveguides 274 and 276 and the other member being the analyte. In this context, the term "biological binding pairs" is as defined above, referring to a corresponding pair of molecules that exhibit mutual affinity or binding capacity, typically specific or non-specific binding or interaction, including biochemical, physiological, and/or pharmaceutical interactions.

As mentioned above, substrate 30 can be flexible. This facilitates a method involving guiding electromagnetic radiation through a waveguide array of at least two waveguides, simultaneously, while altering the conformation of the waveguides. That is, the substrate carrying a plurality of waveguides can be bent or otherwise deformed during electromagnetic radiation propagation. This can be useful for a variety of purposes, one of which is increased sensitivity in a sensor. Where a sensor is sensitive to changes in a surface of a waveguide or cladding that occur upon exposure to an analyte, as described above, sensitivity can be increased as follows. The waveguide can be bent to its limit of maintaining total internal reflection, which is readily determined by bending the waveguide too far and then returning the waveguide to a conformation allowing total internal reflection. Where the interaction of an analyte with the waveguide decreases the difference in refractive index between waveguide and cladding, loss of electromagnetic radiation passing through the waveguide can be indicative of interaction with an analyte, and is made much more sensitive where the waveguide is almost at the limit of maintaining total internal reflection prior to exposure to the analyte. In another example, where coupling between waveguides is highly dependent upon the conformation of the waveguides, altering the conformation of the waveguides (facilitated with a flexible substrate) can result in operation very near the limits of coupling where exposure to an analyte will relatively more greatly affect coupling.

Figure 20:
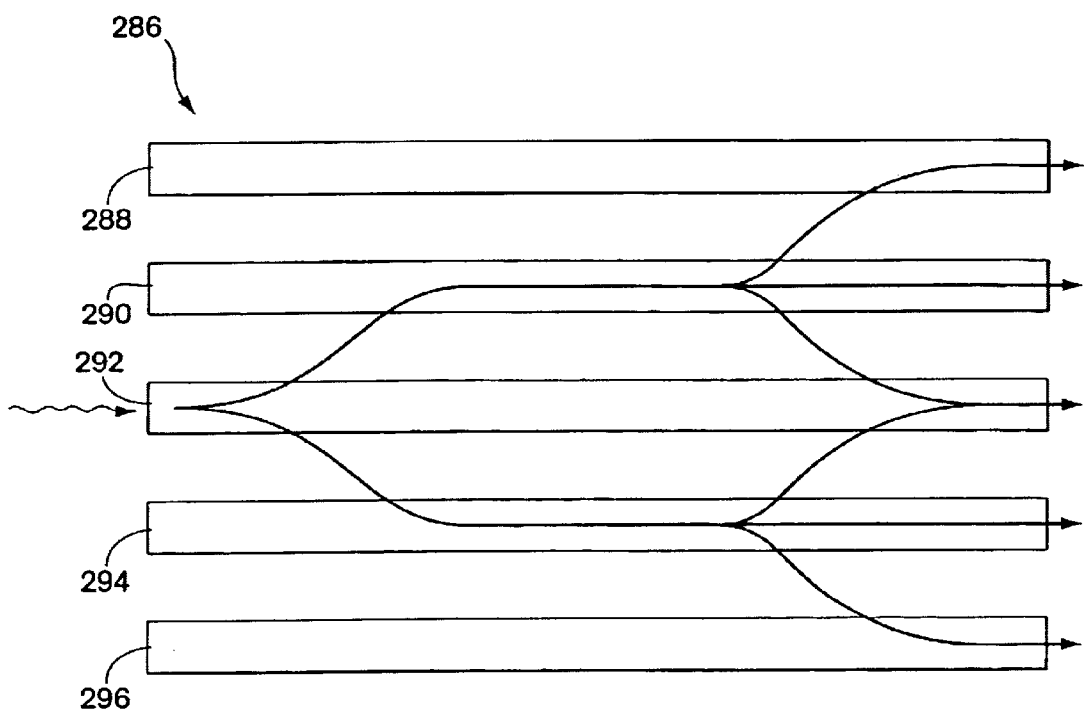
FIG. 20 illustrates formation of an interference pattern via coupling among a five-waveguide array in accordance with the invention.

Referring now to FIG. 20, an array 286 of waveguides 288, 290, 292, 294 and 296, which are essentially linear and parallel, is illustrated. Where the array is fabricated such that conditions allow coupling between waveguides, as described above, light introduced into waveguide 292 can couple into waveguides 290 and 294, and from waveguide 290 can couple back into waveguide 292 and into waveguide 288, and from waveguide 294 can couple back into waveguide 292 and into waveguide 296. The result is that an interferometer is created and an interference pattern defined by radiation emerging from each of waveguides 288–296 is created and is distinctive based upon spacing of the waveguides, refractive index difference between waveguide and cladding, waveguide dimensions, wavelength of radiation, and propagation length. The system of FIG. 20 can serve as a sensor since any change in refractive index differs at the boundaries of one or more waveguides, for example a difference in refractive index of the cladding surrounding waveguides 288–296 such as via exposure to an electric field or electromagnetic radiation, exposure to a fluid, or exposure to another analyte as described above will alter the interference pattern emerging from waveguides 288–296.

A series of working examples were conducted relating to waveguides. With the exception of cross-linking of the polymer, synthesis was conducted in a class-100 clean room.

A poly(dimethylsiloxane) (PDMS) elastomeric mold, or applicator, 20 (sylgard 184, Dow Corning, Silicone Elastomer: curing agent=15:1) was cast from a photoresist pattern made in a standard photolithographic process (Kumar, et al., *Langmuir*, 10, 1498 (1994)). With reference to FIG. 15, an array of waveguides 38 was formed by filling the relief structure (indentations 24) in applicator surface 22 of applicator 20 with a liquid prepolymer (polyurethane, NOA-73, Norland Products New Brunswick, N.J.) and then placing the applicator surface of the filled applicator 20 on substrate surface 28 of a Si(100) wafer 30 supporting a 2 micron-thick layer of $SiO_2$. The prepolymer was cross-linked in situ by irradiating the system for 1 hour at a distance of 1 centimeter with a 450 W medium-pressure Hg vapor lamp (type 7825-34, Ace Glass, Vineland, N.J.). After UV exposure, the elastomeric mold (applicator 20) was peeled away, leaving an array of waveguide structures 38 on substrate 30. The technique was pattern used to generate waveguides with a variety of widths of 2.0, 2.6, 3.0, and 4.0 microns, and spacings of 2.0, 4.0, and 8.0 microns. All waveguides had the same height of approximately 1 micron. The length of the waveguides was determined by the points at which the wafer was fractured. In one set of embodiments the waveguide array was left unclad. In embodiments in which cladding was applied, cladding was made by providing a thick layer of the same liquid prepolymer and applying it to the waveguides, the surfaces of which had been slightly oxidized by exposure for about 10 minutes in a UV-ozone cleaner (models 13550 and 13550-2, Boekel Industries) to render them hydrophilic and improve adhesion. The system was heated to 85° C. on a hot plate to decrease the viscosity of the prepolymer, and the excess prepolymer was allowed to drain to one edge. The thin layer of prepolymer left on the surface was loosely cross-linked by brief (1 minute) exposure to UV light (365 nm) from a 4 W hand-held lamp (Blak-Ray UV lamp model UVL-21, UVP, San Gabrielle, Calif.). The ends of the clad waveguides were squared by cleaving the substrate. After cleaving, the cladding was cured completely (30 seconds) with the 450 W medium-pressure Hg vapor lamp. This procedure allowed the ends of the waveguides to be cleaved when the cladding layer was in the liquid phase, preventing the cladding from de-adhering from the guides.

Figure 21:
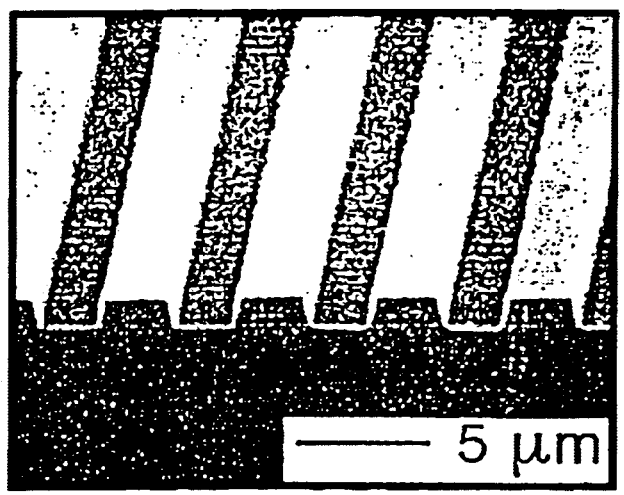
FIG. 21 is a photocopy of a scanning electron micrograph (SEM) image of an unclad array fabricated in accordance with the invention.
Figure 22:
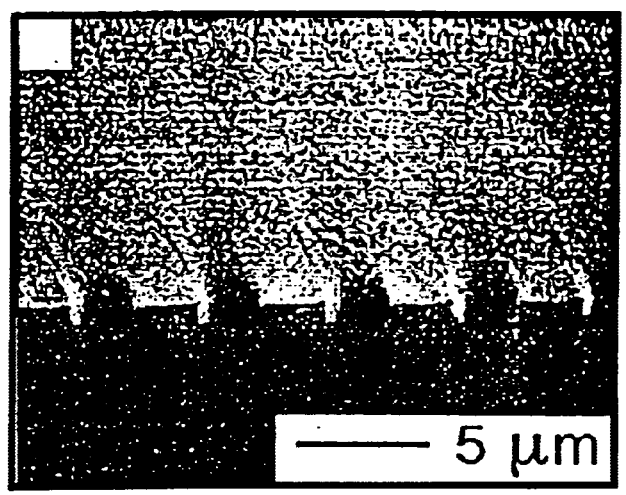
FIG. 22 is a photocopy of an SEM image of a clad array fabricated in accordance with the invention.

FIG. 21 is a photocopy of an SEM image of an unclad waveguide array, and FIG. 22 is a photocopy of an SEM image of a clad array, each fabricated according to this technique. In each case waveguide width was about 2.6 microns, waveguide spacing was about 2.0 microns, and waveguide height was about 1.0 microns.

Figure 23:
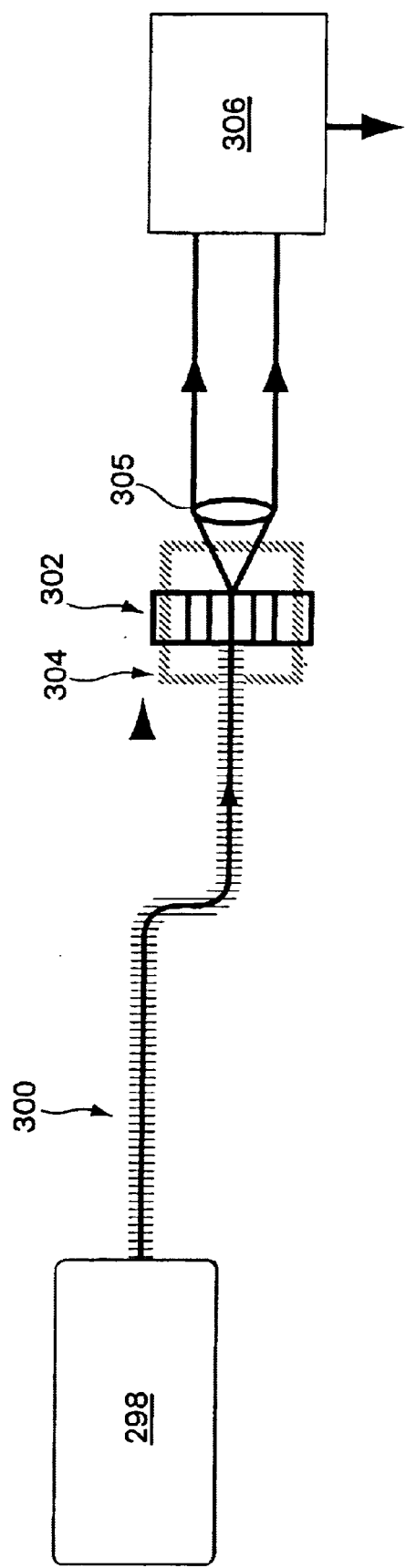
FIG. 23 is a schematic illustration of an optical system used to couple light into waveguide arrays of the invention and to determine interference patterns formed via coupling among the waveguides of the arrays.

FIG. 23 is a schematic diagram of apparatus used to couple light into and out of waveguide arrays fabricated as described immediately above. Light from a He—Ne laser 298 (633 run) was first coupled into a single-mode optical fiber 300 which was butt-coupled to the end of waveguides of array 302 (representative of a variety of waveguide arrays fabricated as described immediately above, and tested in accordance with this example) using a precision 3-dimensional translation stage 304. Light also could be coupled into the waveguide array using focusing apparatus. That is, light from a laser could be focused, through a lens arrangement, to the end of waveguides of the array 302. Using this apparatus, light was selectively coupled into individual waveguides in the array, or into the cladding between or above the waveguides. The output light from the waveguides was imaged with a microscope objective 305 and recorded on a CCD camera 306. The shapes and intensities of the outputs of the individual waveguides could easily be observed (in the absence of the objective 305 the far field patterns from adjacent waveguides overlapped).

Figure 24A:
FIGS. 24a–24g show a variety of waveguide arrays and interference patterns of light emerging from various waveguide arrays and created via coupling between waveguides of the arrays.
Figure 24B:
Figure 24C:

FIGS. 24*a–g* show the results of a variety of different waveguide arrays and inputs, and demonstrate tailorable coupling, using the apparatus of FIG. 23 and waveguide arrays fabricated as described above. In FIG. 24*a*, trapezoidal waveguides 38 indicate the positions, in cross-section, of 3 micron-wide waveguides with neighboring waveguides separated by 8 microns. The height of each waveguide was 1 micron. Optical fiber 300 was positioned as indicated, in alignment with the central of the 5 waveguides. FIG. 24*b* is a photocopy of a CCD camera frame grab of the output of the system of FIG. 24*a*. A single-mode output occurred, with no evanescent coupling between adjacent waveguides. FIG. 24*c* is representative of a second waveguide structure fabricated in accordance with the technique described above, with waveguides separated by 4 microns, rather than 8 microns. The UV exposure time for the array of FIG. 24*c* was the same as for the array of FIG. 24*a*. However, the 4 micron spacing was small enough to allow evanescent coupling between guides and light was observed in 5 adjacent waveguides (FIG. 24*d*: photocopy of a CCD camera frame grab of result). Additionally, as the input optical fiber was moved to adjacent waveguides, this output pattern moved in register. The reproducibility and symmetry of the pattern established the uniformity of the coupling between the waveguides in the array. The low level of light at the exit of the central waveguide was caused by efficient coupling of light from the central waveguide into adjacent waveguides.

Figure 24D:
Figure 24E:

FIG. 24*e* demonstrates the ability to modify the coupling between adjacent waveguides by controlling the difference in refractive indices between the guides and their cladding by manipulating exposure time during UV curing. FIG. 24*e* is a photocopy of a CCD camera frame grab of output of the waveguide of FIG. 24*c* (which produced the pattern of FIG. 24*d*) after additional exposure of the array (waveguides plus cladding) under the 450 W medium-pressure Hg vapor lamp. This exposure reduced the index difference between waveguide core and cladding, and increased the coupling between the waveguides. The change is most easily seen in the change in brightness of the center waveguide between FIG. 24*d* and FIG. 24*e*. In FIG. 24*d*, the light coupled out of the center waveguide into the adjacent waveguides. In FIG. 24*e*, the light coupled from the adjacent waveguides back into the center waveguide. Thus, the center waveguides formed an interferometer. Light from the single waveguide directly addressed by optic fiber 300 was evanescently coupled into nine waveguides and many closed-path interferometers were formed.

Figure 24F:
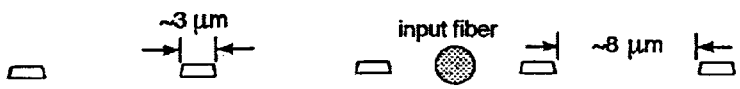
Figure 24G:

FIG. 24*g* shows the output of the array when light was coupled into cladding between the waveguides as shown in FIG. 24*f*. No waveguide output was observed and very little light was observed from the output of the cladding. This demonstrated that the excitation of multiple waveguides as shown in FIGS. 12*d–e* was the result of coupling from propagating waveguide mode to propagating waveguide mode, not from cladding modes to waveguide modes. This interpretation was supported by numerical simulations.

Two-micron-high clad waveguides of width 2.0, 2.6, 3.0, and 4.0 microns and spacing of 2, 4, and 8 microns were fabricated. These taller waveguides had cross-sections approximately equal to the 3.3 micron mode diameter of the optical fiber 300, and gave a coupling efficiency of approximately 35% for a 6 millimeter-long waveguide. Propagation loss was measured in these waveguides to be less than 0.6 dB/cm, which is the limit of measurement uncertainty in the system used.

To demonstrate essentially instantaneous formation of plural waveguide arrays, a waveguide fabrication technique was carried out as described above. An array of about 1,000 3-centimeter-long, two-micron-wide, one-micron-high waveguides were formed over a 0.8 by 3 square centimeter area in a single step taking only five minutes. The parallelism of this procedure makes it a tremendously useful technique for the fabrication of complex but low-cost integrated optical devices.

FIG. 25 illustrates another embodiment of the invention for formation of a structure on a substrate surface using a forming article. In the technique illustrated, fluid precursor 36 is first placed on substrate surface 28, then forming article 20 is brought into contact with fluid precursor 36 and pressed against substrate surface 28 such that the contact surface 26 of the article seals portions of surface 28 that it contacts, thereby forming channels, defined by indentations and portions of substrate surface 28 not contacted by contact surface 26 of the forming article. This is another embodiment in which a micromold is created, defined by article 20 and substrate surface 28. In FIG. 25, following hardening of fluid precursor 36 to the point that it is essentially self-supporting (if it is not so hardened prior to forming with article 20), the applicator is removed resulting in structure 38 which, depending upon the material selected, can be further cured or sintered and which may shrink in the process.

In the working examples described below, a drop of fluid precursor 36 (referring to FIG. 25), was placed on a freshly cleaned substrate and then article 28 was placed face down upon the substrate. A pressure of roughly 10 psi was applied. The area of the patterned surface was typically 1–5 cm² with feature sizes in the micron range. Liquid dewetting of the surface upon application of the applicator was carried out to allow contact of the contact surface 26 of article 20 and the substrate in regions where no fluid precursor derived material was desired. Dewetting is driven by both applied pressure and difference of interfacial tension between fluid precursor 36 and contact surface 26 of article 20. More precisely, the dewetting speed is proportional to S where $S=\gamma_{LS}+\gamma_{LE}-\gamma_{SE}$; $\gamma_{LS}$ is the liquid-substrate interfacial tension, $\gamma_{LE}$ is the liquid-elastomer interfacial tension and $\gamma_{SE}$ is the substrate-elastomer interfacial tension. (F. Brochard-Wyart, P.-G. de Gennes, *J. Phys.: Condens. Matter*, 1994, 6, A9). Since $\gamma_{SE}$ is fixed, the interfacial tension of the fluid precursor solution was increased in order to accelerate dewetting. Although pressure improves the definition of features, it cannot be increased too much because of the deformations induced in the mold if deformation is not required. Diluting fluid precursor with a suitable solvent (in the working examples, acetonitrile, a polar solvent with low viscosity and high surface tension that does not swell the mold) allowed satisfactory dewetting for all patterns used.

Gelation occurred within about an hour, although the mold and structure were allowed to remain undisturbed for about 12 h to allow reasonable consolidation. Gelling time can, however, be decreased by raising pH of the precursor to about 4–5 before casting, and some structures were produced in less than 30 minutes using this technique.

Working examples of molding of sol-gel fluid precursors using a forming article of the invention were carried out. In this set of examples, silicon wafers (Silicon Sense, Massachusetts) were cleaned briefly in an oxygen plasma cleaner before use. Tetramethyl-orthosilicate and di-sec-butoxyaluminoxytriethoxysilane (United Chemicals), titanium isopropoxide and boron triethoxide (Aldrich), oxalic acid and acetonitrile (Fisher) were used as received. Patterned Solid: A silica sol-gel precursor was molded against a silicon wafer that had been patterned by anisotropic etching with square pyramidal pits. A 50-nm thick gold film was prepared on a <100> silicon wafer primed with 2 nm of titanium by e-beam evaporation. A monolayer of hexadecanethiolate was patterned on the wafer using microcontact printing so that the resulting pattern presented uncovered 2-$\mu$m squares, and the unprotected gold was removed with a cyanide etch. (A. Kumar, G. M. Whitesides, *Applied Physics Letters* 1993, 63, 2002). The native silica oxide layer was then removed by etching in 2% HF for 30 sec. The silicon was etched in a 40% by weight solution of KOH in water and isopropanol; this anisotropic etch generated pyramidal pits. The remaining gold was removed with aqua regia. The surface of the resulting textured solid was treated by putting the wafer under static vacuum with a drop of (tridecafluoro-1,1,2,2-tetrahydro-octyl)-1-trichlorosilane for 30 min. This compound polymerized on the surface and made a layer that reduced adhesion to the surface.

A mixture of 6.5 g TMOS and 1.5 g of water acidified to pH=1 by adding oxalic acid was stirred for 1 min and left at room temperature for 1 h (sol A). The mold was prepared by putting a 1 cm² piece of the textured wafer in a plastic petri dish. Just before casting in the mold, 5 drops of aqueous ammonia (pH=11) were added to 3 g of sol A. The wafer was covered with 0.5 ml of this solution. The preparation was then placed in a closed 100 cm³ container for 24 h. The solid structure was not adhering to the mold at this point and was carefully removed. It was then dried slowly at room temperature for a week, then at 60° C. for 2 days. It was finally annealed at 1100° C. for 10 h.

The resulting array of silica pyramids prepared by this technique was analyzed via SEM. The radius of curvature at the tips of the pyramids was less than 50 nm and the angle of the side of the pyramid was 54–58°. This value is compatible with that obtained with this type of silicon etching. (Barycka, et al., *Sensors and Actuators*, 1995, A48, 229). This demonstrates that shrinkage taking place during annealing is essentially isotropic. The sol-gel precursor was molded against a Si/SiO₂ wafer whose surface had been passivated by silanization. The structure was annealed at 1100° C. It measured 5×5×0.3 mm.

Optical waveguides of doped silica on Si/SiO₂ were formed. The silica was doped with aluminum oxide in order to increase its refractive index. Low scattering by the edges of the waveguides can be achieved by an annealing step at a temperature where the viscosity is low enough to allow relaxation of the roughness. In the second working example described below, this temperature was reduced by adding boron oxide to the silica.

Specifically, 0.5 g of di-sec-butoxyaluminoxytriethoxysilane was added to 3 g of sol A. After stirring for 6 h, 3 g of acetonitrile were added to the clear solution (sol B). A solution of 0.8 g of trimethylborate in 3 g of acetonitrile was added to 3 g of sol A and left at room temperature for 1 h (sol C).

One drop of the solution (sol B or C) was placed on a freshly cleaned silicon wafer bearing a 2-$\mu$m thick thermal oxide layer. A 1-cm² elastomeric forming article having a protrusion pattern complementary to the final pattern of the waveguide (illustrated schematically in FIG. 25) was immediately pressed against the surface. The whole structure was placed in a closed 100-cm³ container with one drop of aqueous ammonia (30%). After 18 h, the mold was removed and the structure was consolidated by annealing for 3 h at 1100° C. (for sol B) and 15 min at 800° C. or 900° C. (for sol C).

Figure 26:
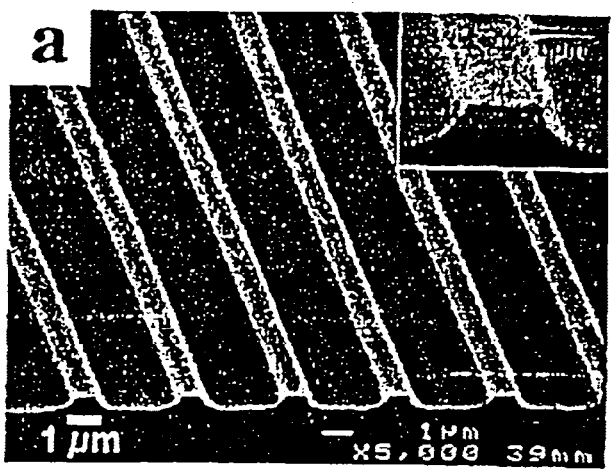
FIG. 26 is a photocopy of a SEM image of an alumino-silicate structure that can serve as a waveguide.
Figure 27:
FIG. 27 is a photocopy of a SEM image of a borosilicate structure that can serve as a waveguide.
Figure 28:
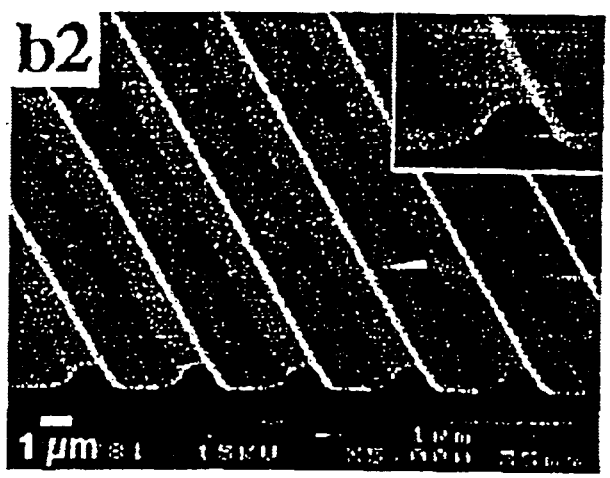
FIG. 28 is a photocopy of a SEM image of the structure of FIG. 27 at a different stage of annealing.

FIGS. 26–29 are photocopies of SEM images of waveguides produced in accordance with this aspect of the invention. FIG. 26 is a photocopy of an SEM image of an aluminosilicate waveguide. FIGS. 27 and 29 are photocopies of SEM images of borosilicate waveguides. FIGS. 27 and 28 show borosilicate lines at different stages of sintering: FIG. 27 shows borosilicate lines after annealing at 800° C. for 10 minutes. FIG. 28 shows the lines after annealing at 900° C. for 10 minutes. Whereas pure sintering seemed to occur at 800° C., the cross section of the lines changed dramatically after annealing at 900° C., due to the melting of the glass, resulting in smoother edges. The composition of the glass was found by XPS to be 9% $B_2O_3$ and 91% $SiO_2$. The waveguiding behavior of the aluminosilicate lines was characterized by coupling a 633-nanometer light beam into one end of a 5 mm long line and imaging the other end. The lines appeared to be single mode waveguides with slight coupling between adjacent lines.

Described above are a variety of sensors of biological or chemical molecules, or the like, that can be made using waveguides fabricated in accordance with the invention. In another set of embodiments, sensors of displacement can be provided. For example, with reference to FIG. 24, where the waveguide array is subjected to compression or tensile forces in a direction perpendicular to the waveguides, causing the waveguides to move closer to or farther apart from each other, coupling between waveguides will change detectably. This can serve as a displacement sensor, pressure sensor, tension sensor, or the like. The waveguide array can be arranged to sense a force by being bent, for example to sense a force applied to an edge of the waveguide, and when the waveguide is bent spacing between waveguides will change and the coupling pattern will change. Waveguides made of glass as described above may also serve as active devices for integrated optics. For instance, aluminosilicate waveguides can be doped with rare earth, like neodymium or erbium. Doped waveguides can be used as integrated light-amplifiers or lasers when placed in a suitably geometry. A regular array of doped waveguides fabricated by this method, when put in a resonant cavity, could exhibit a very interesting behavior where all the lasers would be in phase, leading to a much higher intensity light beam.

What is claimed is:

1. A method of creating a pattern of a species at a defined region proximate a substrate surface, comprising:

providing an article having a contoured surface including at least one indentation defining a pattern;

forming at a first region proximate a substrate surface, in a pattern corresponding to the indentation pattern, a fluid precursor of the species;

allowing the fluid precursor to harden at the first region of the substrate surface, in a pattern corresponding to the indentation pattern; and positioning a second fluid precursor in contact with the hardened first fluid precursor and allowing the second fluid precursor to harden to form a component having a refractive index different from the refractive index of the hardened first precursor.

2. A method as in claim 1, wherein the fluid precursor is a solution or suspension of an inorganic compound and the allowing step comprises allowing the inorganic compound to harden at the first region of the substrate surface.

3. A method as in claim 1, wherein the fluid precursor comprises a suspension of particles in a fluid carrier and the allowing step comprises allowing the fluid carrier to dissipate thereby depositing the particles at the first region of the substrate surface.

4. A method as in claim 1, wherein the forming step comprises transferring the fluid precursor essentially instantaneously from the contoured surface of the article to the first region of the substrate surface.

5. A method as in claim 1, wherein the pattern includes distinct, isolated first and second indentation regions, the forming step comprising transferring at least one fluid precursor from the contoured surface of the article to distinct first and second portions of the substrate surface while leaving an intervening portion of the substrate surface free of the at least one precursor.

6. A method as in claim 5, wherein the transferring step involves transferring the at least one fluid precursor to the first and second portions of the substrate surface simultaneously.

7. A method as in claim 1, wherein the fluid precursor is a prepolymeric species.

8. A method as in claim 1, involving transferring the fluid precursor essentially instantaneously from the article to the substrate surface.

9. A method as in claim 1, comprising allowing the fluid precursor to harden in a pattern including a portion having a lateral dimension of less than about 100 microns.

10. A method as in claim 1, wherein the substrate surface is planar.

11. A method as in claim 1, wherein the substrate surface is non-planar.

12. A method as in claim 1, wherein the substrate is essentially rigid.

13. A method as in claim 1, in which the substrate is essentially flexible.

14. A method as in claim 1, wherein the substrate is silicon.

15. A method as in claim 1, wherein the article having the contoured surface is polymeric.

16. A method as in claim 15, wherein the article is elastomeric.

17. A method as in claim 1, comprising forming the fluid precursor in the pattern on the surface by providing an amount of the fluid precursor on the substrate surface and pressing the contoured surface of the article into the precursor against the substrate surface.

18. A method as in claim 1, involving allowing the precursor to harden, then removing the article from the substrate surface.

19. A method as in claim 1, wherein the precursor is hardened by exposure to electromagnetic radiation.

* * * * *

UNITED STATES PATENT AND TRADEMARK OFFICE
CERTIFICATE OF CORRECTION

PATENT NO. : 6,660,192 B1
DATED : December 9, 2003
INVENTOR(S) : Ehoch Kim et al.

It is certified that error appears in the above-identified patent and that said Letters Patent is hereby corrected as shown below:

<u>Title page,</u>
Add Item:

-- [73] Assignee: President and Fellows of Harvard College
Cambridge, Massachusetts --

Signed and Sealed this

Twenty-seventh Day of April, 2004

JON W. DUDAS
*Acting Director of the United States Patent and Trademark Office*